US006372887B1

(12) United States Patent
Silver et al.

(10) Patent No.: US 6,372,887 B1
(45) Date of Patent: Apr. 16, 2002

(54) FLEA SERINE PROTEASE INHIBITOR PROTEINS

(75) Inventors: Gary M. Silver; Nancy Wisnewski, both of Fort Collins, CO (US)

(73) Assignee: Heska Corporation, Fort Collins, CO (US)

(*) Notice: Subject to any disclaimer, the term of this patent is extended or adjusted under 35 U.S.C. 154(b) by 0 days.

(21) Appl. No.: 08/745,995

(22) Filed: Nov. 7, 1996

(51) Int. Cl.$^7$ .................. C07K 14/81; C07K 14/00; C07K 14/435
(52) U.S. Cl. .................. 530/350; 514/2; 435/69.2; 424/184.1
(58) Field of Search .................. 530/350, 300, 530/858; 536/23.5; 424/184.1, 94.1, 94.64; 435/69.2; 514/2

(56) References Cited

U.S. PATENT DOCUMENTS

| | | | | |
|---|---|---|---|---|
| 4,879,213 A | * | 11/1989 | Fox et al. | |
| 5,011,909 A | * | 4/1991 | Borowsky et al. | |
| 5,196,304 A | | 3/1993 | Kanost et al. | ............... 435/6 |
| 5,436,392 A | | 7/1995 | Thomas et al. | ............. 800/205 |
| 5,439,924 A | * | 8/1995 | Miller | |
| 5,712,143 A | * | 1/1998 | Grieve et al. | |

FOREIGN PATENT DOCUMENTS

| WO | 9417813 | * | 8/1994 |
|---|---|---|---|
| WO | 9614089 | * | 5/1996 |

OTHER PUBLICATIONS

Burgess et al: J. Cell. Biol.(1991) vol. 111, 2129–2138.*
Lazar et al Mol. Cell. Biol. (1988) vol. 8, No. 3, 1247–1252.*
Rieger et al. (1991) Glossary of Genetics, pp. 16–17, 1991.*
Casu, et al., "Isolation of a trysin–like serine protease gene family from the sheep blowfly *Lucilia cuprina*," 1994, pp. 159–170, *Insect Molecular Biology* 3(3).
Fox, et al., "Degradation of Adipokinetic Hormone Family Peptides by a Circulating Endopeptidase in the Insect *Manduca sexta*," 1991, pp. 937–944, *Peptides 12*.
Jiang, et al., "Expression and Characterization of Recombinant *Manduca sexta* Serpin–1B and Site–directed Mutants that Change its Inhibitory Selectivity," 1995, pp. 1093–1100, *Insect Biochem. Molec. Biol.* 25:10.
Jiang, et al., "Mutually Exculusive Exon Use and Reactive Center Diversity in Insect Serpins," 1994, pp. 55–58, *The Journal of Biological Chemical* 269:1.
Kanost, et al., "Primary Structure of a Member of the Serpin Superfamily of Proteinase Inhibitors from an Insect, *Manduca sexta*," 1989, pp. 965–972, *The Journal of Biological Chemistry* 264:2.
Kanost, et al., "Molecular Analysis of Hemolymph Proteins: Serpin Genes," 1995, p. 193, *J. Cell. Biochem., Suppl 21A*.
Kellenberger, et al., "Serine Protease Inhibition by Insect Peptides Containing a Cyst Knot and a Triple–stranded β–Sheet," 1995, pp. 25514–25519, *The Journal of Biological Chemistry* 270:43.
Narumi, et al., "Molecular cloning of silkworm (Bombyx mori) antichymotrypsin," 1993, pp. 181–187, *Eur. J. Biochem. 214*.
Sasaki, "Patchwork–structure serpins form silkworm (Bombyx mori) larval hemolymph," 1991, pp. 255–261, *Eur. J. Biochem. 202*.
Takagi, et al., "Amino Acid Sequence of Silkworm (Bombyx mori) Hemolymph Antitrypsin Deduced from Its cDNA Nucleotide Sequence: Confirmation of Its Homology with Serpins," 1990, pp. 372–378, *J. Biochem. 108*.
Valaitis, "Gypsy Moth Midgut Proteinases: Purification and Characterization of Luminal Trypsin, Elastase and the Brush Border Membrane Leucine Aminopeptidase," 1995, pp. 139–149, *Insect Biochem. Molec. Biol.* 25:1.
Locht, et al., "Two heads are better than one: crystal structure of the insect derived double domain Kazal inhibitor rhodniin in complex with thrombin," 1995, pp. 5149–5157, *The EMBO Journal* 14:21.

* cited by examiner

Primary Examiner—Michael Pak
(74) Attorney, Agent, or Firm—Heska Corporation

(57) ABSTRACT

The present invention relates to flea serine protease inhibitor proteins; to flea serine protease inhibitor nucleic acid molecules, including those that encode such serine protease inhibitor proteins; to antibodies raised against such serine protease inhibitor proteins; and to compounds that inhibit flea serine protease inhibitor activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from hematophagous ectoparasite infestation.

4 Claims, No Drawings

FLEA SERINE PROTEASE INHIBITOR PROTEINS

FIELD OF THE INVENTION

The present invention relates to flea serine protease inhibitor nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from flea infestation.

BACKGROUND OF THE INVENTION

Hematophagous ectoparasite infestation of animals is a health and economic concern because hematophagous ectoparasites are known to cause and/or transmit a variety of diseases. Hematophagous ectoparasites directly cause a variety of diseases, including allergies, and also carry a variety of infectious agents including, but not limited to, endoparasites (e.g., nematodes, cestodes, trematodes and protozoa), bacteria and viruses. In particular, the bites of hematophagous ectoparasites are a problem for animals maintained as pets because the infestation becomes a source of annoyance not only for the pet but also for the pet owner who may find his or her home generally contaminated with insects. As such, hematophagous ectoparasites are a problem not only when they are on an animal but also when they are in the general environment of the animal.

Bites from hematophagous ectoparasites are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of hematophagous ectoparasite infestation has prompted the development of reagents capable of controlling hematophagous ectoparasite infestation. Commonly encountered methods to control hematophagous ectoparasite infestation are generally focused on use of insecticides. While some of these products are efficacious, most offer protection of a very limited duration at best. Furthermore, many of the methods are often not successful in reducing hematophagous ectoparasite populations. In particular, insecticides have been used to prevent hematophagous ectoparasite infestation of animals by adding such insecticides to shampoos, powders, sprays, foggers, collars and liquid bath treatments (i.e., dips). Reduction of hematophagous ectoparasite infestation on the pet has been unsuccessful for one or more of the following reasons: (1) failure of owner compliance (frequent administration is required); (2) behavioral or physiological intolerance of the pet to the pesticide product or means of administration; and (3) the emergence of hematophagous ectoparasite populations resistant to the prescribed dose of pesticide.

Prior investigators have described sequences of a few insect serine protease inhibitors: *Bombyx mori* nucleic acid and amino acid sequences have been disclosed by Narumi et al., *Eur. J. Biochem.*, 214:181–187, 1993; Takagi et al., *J. Biochem.*, 108:372–378, 1990; and amino acid sequence has been disclosed by Sasaki, *Eur. J Biochem*, 202:255–261, 1991. *Manduca sexta* nucleic acid and amino acid sequences have been disclosed by Kanost et al., *J. Biol. Chem*, 264:965–972, 1989; U.S. Pat. No. 5,436,392, to Thomas et al., issued Jul. 25, 1990, 2085; U.S. Pat. No. 5,196,304, to Kanost et al., issued Mar. 23, 1993; Jiang et al., *J. Biol. Chem.*, 269:55–58, 1994; *and Manduca sexta* peptide sequences have been disclosed by Fox et al., Peptides, 12:937–944, 1991. *Locusta migratoria* peptide sequences have been disclosed by Kellenberger et al., *J. Biol. Chem*, 270:25514–25519, 1995. *Rhodnius prolixus* peptide sequences have been disclosed by Van De Locht, EMBO, 14:5149–5157, 1995. *Lymantria dispar* peptide sequences have been disclosed by Valaitis, *Insect Biochem Molec Biol*, 25:139–149, 1995. *Lucilia cuprina* nucleic acid and amino acid sequences have been disclosed by Casu et al., *Insect Molecular Biology*, 3:159–170, 1994. Identification of a serine protease inhibitor of the present invention is unexpected because the most identical amino acid or nucleic acid sequence identified by previous investigators could not be used to identify a flea serine protease inhibitor of the present invention.

In summary, there remains a need to develop a reagent and a method to protect animals from hematophagous ectoparasite infestation.

SUMMARY OF THE INVENTION

The present invention relates to a novel product and process for protection of animals from hematophagous ectoparasite infestation. According to the present invention there are provided flea serine protease inhibitor proteins and mimetopes thereof; flea nucleic acid molecules, including those that encode such proteins; antibodies raised against such serine protease inhibitor proteins (i.e., anti-flea serine protease inhibitor antibodies); and other compounds that inhibit flea serine protease inhibitor activity (i.e, inhibitory compounds or inhibitors).

The present invention also includes methods to obtain such proteins, mimetopes, nucleic acid molecules, antibodies and inhibitory compounds. Also included in the present invention are therapeutic compositions comprising such proteins, mimetopes, nucleic acid molecules, antibodies, and/or inhibitory compounds, as well as use of such therapeutic compositions to protect animals from hematophagous ectoparasite infestation.

Identification of a serine protease inhibitor protein of the present invention is unexpected because the most identical amino acid or nucleic acid sequence identified by previous investigators could not be used to identify a flea serine protease inhibitor protein of the present invention. In addition, identification of a flea serine protease inhibitor protein of the present invention is unexpected because a protein fraction from flea prepupal larvae that was obtained by monitoring for carboxylesterase activity surprisingly also contained flea serine protease inhibitor molecular epitopes of the present invention.

One embodiment of the present invention is an isolated flea serine protease nucleic acid molecule that hybridizes under stringent hybridization conditions with a *Ctenocephalides felis* serine protease inhibitor gene, including, but not limited to, nucleic acid molecules that hybridize under stringent conditions with a nucleic acid molecule having at least one of the following nucleic acid sequences: SEQ ID NO:1, SEQ ID NO:3, SEQ ID NO:4, SEQ ID NO:5, SEQ ID NO:7, SEQ ID NO:9, SEQ ID NO: 10, SEQ ID NO:11, SEQ ID NO:13, SEQ ID NO:15, SEQ ID NO:16, SEQ ID NO: 17, SEQ ID NO:19, SEQ ID NO:21, SEQ ID NO:22, SEQ ID NO:23, SEQ ID NO:25, SEQ ID NO:27, SEQ ID NO:28, SEQ ID NO:29, SEQ ID NO:31, SEQ ID NO:33, SEQ ID NO:34, and SEQ ID 35. Particularly preferred flea serine protease inhibitor nucleic acid molecules include nucleic acid sequences SEQ ID NO:1, SEQ ID NO:3, SEQ ID NO:4, SEQ ID NO:5, SEQ ID NO:7, SEQ ID NO:9, SEQ ID NO: 10, SEQ ID NO:1 1, SEQ ID NO:13, SEQ ID NO:15, SEQ ID NO:16, SEQ ID NO:17, SEQ ID NO:19, SEQ ID NO:21, SEQ ID NO:22, SEQ ID NO:23, SEQ ID NO:25, SEQ ID NO:27, SEQ ID NO:28, SEQ ID NO:29, SEQ ID NO:31, SEQ ID NO:33, SEQ ID NO:34, and SEQ ID 35, and/or nucleic acid sequences encoding proteins having amino acid sequences SEQ ID NO:2, SEQ ID N:6, SEQ ID NO:8, SEQ ID NO:12, SEQ ID NO: 14, SEQ ID NO:18, SEQ ID NO:20, SEQ ID NO:24, SEQ ID NO:26, SEQ ID NO:32, and SEQ ID NO:36, as well as allelic variants of any of the listed nucleic acid sequences or complements of any of the listed nucleic acid sequences.

The present invention also includes an isolated nucleic acid molecule that hybridizes under stringent hybridization conditions with a nucleic acid sequence encoding a protein comprising an amino acid sequence including SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO:30, SEQ ID NO:32 and SEQ ID NO:36.

The present invention also relates to recombinant molecules, recombinant viruses and recombinant cells that include flea serine protease inhibitor nucleic acid molecules of the present invention. Also included are methods to produce such nucleic acid molecules, recombinant molecules, recombinant viruses and recombinant cells.

Another embodiment of the present invention includes an isolated flea serine protease inhibitor protein. A preferred flea serine protease inhibitor protein is capable of eliciting an immune response when administered to an animal and/or of having serine protease inhibitor activity. A preferred flea serine protease inhibitor protein is encoded by a nucleic acid molecule that hybridizes under stringent hybridization conditions to a nucleic acid sequence including SEQ ID NO:3, SEQ ID NO:9, SEQ ID NO:15, SEQ ID NO:21, SEQ ID NO:27 and SEQ ID NO:33. Particularly preferred flea serine protease inhibitor proteins include at least one of the following amino acid sequences: SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO:30, SEQ ID NO:32, or SEQ ID NO:36.

Yet another embodiment of the present invention is a therapeutic composition that is capable of reducing hematophagous ectoparasite infestation. Such a therapeutic composition includes one or more of the following protective compounds: an isolated flea serine protease inhibitor protein or a mimetope thereof; an isolated nucleic acid molecule that hybridizes under stringent hybridization conditions with a *Ctenocephalides felis* serine protease inhibitor gene; an isolated antibody that selectively binds to a flea *Ctenocephalides felis* serine protease inhibitor protein; and an inhibitor of serine protease inhibitor protein activity identified by its ability to inhibit flea serine protease inhibitor activity, such as, but not limited to, a substrate analog of a flea serine protease inhibitor protein. A preferred therapeutic composition of the present invention also includes an excipient, an adjuvant and/or a carrier. Also included in the present invention is a method to reduce flea infestation. The method includes the step of administering to the animal a therapeutic composition of the present invention.

The present invention also includes an inhibitor of serine protease inhibitor protein activity identified by its ability to inhibit the activity of a flea serine protease inhibitor protein. An example of such an inhibitor is a substrate analog of a flea serine protease inhibitor protein. Also included in the present invention are mimetopes of flea serine protease inhibitor proteins of the present invention identified by their ability to inhibit flea serine protease activity.

Yet another embodiment of the present invention is a method to identify a compound capable of inhibiting flea serine protease inhibitor activity. The method includes the steps of: (a) contacting an isolated flea serine protease inhibitor protein with a putative inhibitory compound under conditions in which, in the absence of the compound, the protein has serine protease inhibitor activity; and (b) determining if the putative inhibitory compound inhibits the activity. Also included in the present invention is a test kit to identify a compound capable of inhibiting flea serine protease inhibitor activity. Such a kit includes an isolated flea serine protease inhibitor protein having serine protease inhibitor activity and a means for determining the extent of inhibition of the activity in the presence of a putative inhibitory compound.

Yet another embodiment of the present invention is a method to produce a flea serine protease inhibitor protein, the method comprising culturing a cell transformed with a nucleic acid molecule that hybridizes under stringent hybridization conditions with a *Ctenocephalides felis* serine protease inhibitor gene.

DETAILED DESCRIPTION OF THE INVENTION

The present invention provides for isolated flea serine protease inhibitor (SPI) proteins, isolated flea serine protease inhibitor nucleic acid molecules, antibodies directed against flea serine protease inhibitor proteins and other inhibitors of flea serine protease inhibitor activity. As used herein, the terms isolated flea serine protease inhibitor proteins and isolated flea serine protease inhibitor nucleic acid molecules refers to serine protease inhibitor proteins and serine protease inhibitor nucleic acid molecules derived from fleas and, as such, can be obtained from their natural source or can be produced using, for example, recombinant nucleic acid technology or chemical synthesis. A SPI protein can have the ability to inhibit the proteolytic activity of a serine protease protein. A protein denoted as a SPI protein can also possess cysteine protease activity, in addition to serine protease activity. Also included in the present invention is the use of these proteins, nucleic acid molecules, antibodies and other inhibitors as therapeutic compositions to protect animals from hematophagous ectoparasite infestation as well as in other applications, such as those disclosed below.

Flea serine protease inhibitor proteins and nucleic acid molecules of the present invention have utility because they represent novel targets for anti-hematophagous ectoparasite vaccines and drugs. The products and processes of the present invention are advantageous because they enable the inhibition of hematophagous ectoparasite serine protease activity necessary for hematophagous ectoparasite survival or the inhibition of serine protease inhibitors, thereby deregulating serine protease activity, leading to uncontrolled proteolysis of an hematophagous ectoparasite.

One embodiment of the present invention is an isolated protein comprising a flea SPI protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated flea SPI protein can be a full-length protein or any homolog of such a protein. An isolated protein of the present invention, including a homolog, can be identified in a straight-forward manner by the protein's ability to elicit an immune response against flea SPI proteins and/or ability to inhibit, or reduce, serine protease activity. Examples of serine protease inhibitor homologs include SPI proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/ or addition of glycerophosphatidyl inositol) such that the homolog includes at least one epitope capable of eliciting an immune response against a flea protein or has at least some serine protease inhibitor activity. For example, when the homolog is administered to an animal as an inununogen, using techniques known to those skilled in the art, the animal will produce an immune response against at least one epitope of a natural flea SPI protein. The ability of a protein to effect an immune response, can be measured using techniques known to those skilled in the art. Techniques to measure serine protease inhibitor activity are also known to those skilled in the art; see, for example, Jiang et al., 1995, *Insect Biochem. Molec. Biol.* 25, 1093–1100.

Flea SPI protein homologs can be the result of natural allelic variation or natural mutation. SPI protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

Isolated SPI proteins of the present invention have the further characteristic of being encoded by nucleic acid molecules that hybridize under stringent hybridization conditions to a gene encoding a *Ctenocephalides felis* SPI protein (i.e., a *C. felis* SPI gene). As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual,* Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

As used herein, a *C. felis* SPI gene includes all nucleic acid sequences related to a natural *C. felis* SPI gene such as regulatory regions that control production of the *C. felis* SPI protein encoded by that gene (such as, but not limited to, transcription, translation or post-translation control regions) as well as the coding region itself. In one embodiment, a *C. felis* SPI gene of the present invention includes the nucleic acid sequence SEQ ID NO:1, SEQ ID NO:3, SEQ ID NO:7, SEQ ID NO:9, SEQ ID NO:13, SEQ ID NO:15, SEQ ID NO:19, SEQ ID NO:21, SEQ ID NO:25, SEQ ID NO:27, SEQ ID NO:31 and/or SEQ ID NO:33. Nucleic acid sequence SEQ ID NO:1 represents the deduced sequence of the coding strand of a complementary DNA (cDNA) nucleic acid molecule denoted herein as $nfSPI1_{1584}$, the production of which is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a complete double helix with) the strand for which the sequence is cited.

Nucleic acid sequence SEQ ID NO:7 represents the deduced sequence of the coding strand of a cDNA nucleic acid molecule denoted herein as $nfSPI2_{1358}$, the production of which is disclosed in the Examples. The complement of SEQ ID NO:7 is represented herein by SEQ ID NO:9.

Nucleic acid sequence SEQ ID NO:13 represents the deduced sequence of the coding strand of a cDNA nucleic acid molecule denoted herein as $nfSPI3_{1838}$, the production of which is disclosed in the Examples. The complement of SEQ ID NO:13 is represented herein by SEQ ID NO:15.

Nucleic acid sequence SEQ ID NO:19 represents the deduced sequence of the coding strand of a cDNA nucleic acid molecule denoted herein as $nfSPI4_{1414}$, the production of which is disclosed in the Examples. The complement of SEQ ID NO:19 is represented herein by SEQ ID NO:21.

Nucleic acid sequence SEQ ID NO:25 represents the deduced sequence of the coding strand of a cDNA nucleic acid molecule denoted herein as $nfSPI5_{1492}$, the production of which is disclosed in the Examples. The complement of SEQ ID NO:25 is represented herein by SEQ ID NO:27.

Nucleic acid sequence SEQ ID NO:31 represents the deduced sequence of the coding strand of a cDNA nucleic acid molecule denoted herein as $nfSPI6_{1454}$, the production of which is disclosed in the Examples. The complement of SEQ ID NO:31 is represented herein by SEQ ID NO:33.

It should be noted that since nucleic acid sequencing technology is not entirely error-free, SEQ ID NO:1, SEQ ID NO:7, SEQ ID NO:13, SEQ ID NO:19, SEQ ID NO:25 and SEQ ID NO:31, and complements thereof (as well as other nucleic acid and protein sequences presented herein), at best, represent apparent nucleic acid sequences of certain nucleic acid molecules encoding *C. felis* SPI proteins of the present invention.

In another embodiment, a *C. felis* SPI gene can be an allelic variant that includes a similar but not identical sequence to SEQ ID NO:1, SEQ ID NO:3, SEQ ID NO:4, SEQ ID NO:5, SEQ ID NO:7, SEQ ID NO:9, SEQ ID NO:10, SEQ ID NO:11, SEQ ID NO:13, SEQ ID NO:15, SEQ ID NO:16, SEQ ID NO:17, SEQ ID NO:19, SEQ ID NO:21, SEQ ID NO:22, SEQ ID NO:23, SEQ ID NO:25, SEQ ID NO:27, SEQ ID NO:28, SEQ ID NO:29, SEQ ID NO:31, SEQ ID NO:33, SEQ ID NO:34, and/or SEQ ED 35.

An allelic variant of a *C. felis* SPI gene is a gene that occurs at essentially the same locus (or loci) in the genome as the gene including SEQ ID NO:1, SEQ ID NO:3, SEQ ID NO:4, SEQ ID NO:5, SEQ ID NO:7, SEQ ID NO:9, SEQ ID NO:10, SEQ ID NO:11, SEQ ID NO:13, SEQ ID NO:15, SEQ ID NO:16, SEQ ID NO:17, SEQ ID NO:19, SEQ ID NO:21, SEQ ID NO:22, SEQ ID NO:23, SEQ ID NO:25, SEQ ID NO:27, SEQ ID NO:28, SEQ ID NO:29, SEQ ID NO:31, SEQ ID NO:33, SEQ ID NO:34 and SEQ ID NO:35, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given flea since the genome is diploid and/or among a group of two or more fleas.

The minimal size of a SPI protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a SPI protein homolog of the present invention is from about 12 to about 18 nucleotides in length. Thus, the minimal size of a SPI protein homolog of the present invention is from about 4 to about 6 amino acids in length. There is no limit, other than a practical limit, on the maximal size of such a nucleic acid molecule in that the nucleic acid molecule can include a portion of a gene, an entire gene, multiple genes, or portions thereof. The preferred size of a protein encoded by a nucleic acid molecule of the present invention depends on whether a full-length, fusion, multivalent, or functional portion of such a protein is desired.

Suitable fleas from which to isolate SPI proteins of the present invention (including isolation of the natural protein or production of the protein by recombinant or synthetic techniques) include Ctenocephalides, Ceratophyllus, Diamanus, Echidnophaga, Nosopsyllus, Pulex, Tunga, Oropsylla, Orchopeus and Xenopsylla. More preferred fleas from which to isolate SPI proteins include *Ctenocephalides felis, Ctenocephalides canis, Ceratophyllus pulicidae, Pulex irritans, Oropsylla (Thrassis) bacchi, Oropsylla (Diamanus) montana, Orchopeus howardi, Xenopsylla cheopis and Pulex simulans*, with *C. felis* being even more preferred.

Suitable flea tissues from which to isolate a SPI protein of the present invention includes tissues from unfed fleas or tissue from fleas that recently consumed a blood meal (i.e., blood-fed fleas). Such flea tissues are referred to herein as, respectively, unfed flea tissues and fed flea tissues. Preferred flea tissues from which to obtain a SPI protein of the present invention includes unfed or fed pre-pupal larval, $1^{st}$ instar larval, $2^{nd}$ instar larval, $3^{rd}$ instar larval, and/or adult flea tissues. More preferred flea tissue includes prepupal larval tissue. A SPI of the present invention is also preferably obtained from hemolymph.

A preferred flea SPI protein of the present invention is a compound that when administered to an animal in an effective manner, is capable of protecting that animal from a hematophagous ectoparasite infestation. In accordance with the present invention, the ability of a SPI protein of the present invention to protect an animal from a hematophagous ectoparasite infestation refers to the ability of that protein to, for example, treat, ameliorate and/or prevent infestation caused by a hematophagous ectoparasite. In particular, the phrase "to protect an animal from hematophagous ectoparasite infestation" refers to reducing the potential for hematophagous ectoparasite population expansion on and around the animal (i.e., reducing the hematophagous ectoparasite burden). Preferably, the hematophagous ectoparasite population size is decreased, optimally to an extent that the animal is no longer bothered by hematophagous ectoparasites. A host animal, as used herein, is an animal from which hematophagous ectoparasites can feed by attaching to and feeding through the skin of the animal. Hematophagous ectoparasites, and other ectoparasites, can live on a host animal for an extended period of time or can attach temporarily to an animal in order to feed. At any given time, a certain percentage of a hematophagous ectoparasite population can be on a host animal whereas the remainder can be in the environment of the animal. Such an environment can include not only adult hematophagous ectoparasites, but also hematophagous ectoparasite eggs and/or hematophagous ectoparasite larvae. The environment can be of any size such that hematophagous ectoparasite in the environment are able to jump onto and off of a host animal. For example, the environment of an animal can include plants, such as crops, from which hematophagous ectoparasites infest an animal. As such, it is desirable not only to reduce the hematophagous ectoparasite burden on an animal per se, but also to reduce the hematophagous ectoparasite burden in the environment of the animal. In one embodiment, a SPI protein of the present invention can elicit an immune response (including a humoral and/or cellular immune response) against a hematophagous ectoparasite.

Suitable hematophagous ectoparasites to target include any hematophagous ectoparasite that is essentially incapable of infesting an animal administered a SPI protein of the present invention. As such, a hematophagous ectoparasite to target includes any hematophagous ectoparasite that produces a protein having one or more epitopes that can be targeted by a humoral and/or cellular immune response against a SPI protein of the present invention, that can be targeted by a compound that otherwise inhibits SPI activity, and/or that can be targeted by a SPI protein (e.g., a peptide) or mimetope of a SPI protein of the present invention in such a manner as to inhibit serine protease activity, thereby resulting in the decreased ability of the hematophagous ectoparasite to infest an animal. Preferred hematophagous ectoparasite to target include insects and acarines. A SPI protein of the present invention preferably protects an animal from infestation by hematophagous ectoparasites including, but are not limited to, agricultural pests, stored product pests, forest pests, structural pests or animal health pests. Suitable agricultural pests of the present invention include, but are not limited to, Colorado potato beetles, corn earworms, fleahoppers, weevils, pink boll worms, cotton aphids, beet armyworms, lygus bugs, hessian flies, sod webworms, whites grubs, diamond back moths, white flies, planthoppers, leafhoppers, mealy bugs, mormon crickets and mole crickets. Suitable stored product pests of the present invention include, but are not limited to, dermestids, anobeids, saw toothed grain beetles, indian mealmoths, flour beetles, long-horn wood boring beetles and metallic wood boring beetles. Suitable forest pests of the present invention include, but are not limited to, southern pine bark beetles, gypsy moths, elm beetles, ambrosia bettles, bag worms, tent worms and tussock moths. Suitable structural pests of the present invention include, but are not limited to, bess beetles, termites, fire ants, carpenter ants, wasps, hornets, cockroaches, silverfish, *Musca domestica* and *Musca autumnalis*. Suitable animal health pests of the present invention include, but are not limited to, fleas, ticks, mosquitoes, black flies, lice, true bugs, sand flies, Psychodidae, tsetse flies, sheep blow flies, cattle grub, mites, horn flies, heel flies, deer flies, Culicoides and warble flies. A SPI protein of the present invention more preferably protects an animal from infestation by hematophagous ectoparasites including fleas, midges, mosquitos, sand flies, black flies, horse flies, snipe flies, louse flies, horn flies, deer flies, tsetse flies, buffalo flies, blow flies, stable flies, myiasis-causing flies, biting gnats, lice, mites, bee, wasps, ants, true bugs and ticks, even more preferably fleas and ticks, and even more preferably fleas. Preferred fleas from which to protect an animal from flea infestation include those disclosed herein for the isolation of a SPI of the present invention.

The present invention also includes mimetopes of SPI proteins of the present invention. As used herein, a mimetope of a SPI protein of the present invention refers to any compound that is able to mimic the activity of such a SPI protein (e.g., ability to elicit an immune response against a SPI protein of the present invention and/or ability to inhibit serine protease activity), often because the mimetope has a structure that mimics the SPI protein. It is to be noted, however, that the mimetope need not have a structure similar to an SPI protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of SPI proteins of the present invention. Mimetopes can also be obtained by generating random samples of molecules, such as oligonucleotides, peptides or other organic molecules, and screening such samples by affinity chromatography techniques using the corresponding binding partner, (e.g., a flea serine protease or anti-flea serine protease inhibitor antibody). A preferred mimetope is a peptidomimetic compound that is structurally and/or functionally similar to a SPI protein of the present invention, particularly to the active site of the SPI protein.

One embodiment of a flea SPI protein of the present invention is a fusion protein that includes a flea SPI protein-containing domain attached to one or more fusion segments. Suitable fusion segments for use with the present invention include, but are not limited to, segments that can: enhance a protein's stability; act as an immunopotentiator to enhance an immune response against a SPI protein; and/or assist purification of a SPI protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the SPI-containing domain of the protein and can be susceptible to cleavage in order to enable straightforward recovery of a SPI protein. Fusion proteins are preferably produced by culturing a recombinant cell transformed with a fusion nucleic acid molecule that encodes a protein including the fusion segment attached to either the carboxyl and/or amino terminal end of a SPI-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include PHis-PfSPI$2_{376}$, PHis-PfSPI$3_{390}$, PHis-PfSPI$4_{376}$, and PHis-PfSPI$6_{376}$, production of which are disclosed herein.

In another embodiment, a flea SPI protein of the present invention also includes at least one additional protein segment that is capable of protecting an animal from hematophagous ectoparasite infestations. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from hematophagous ectoparasite infestation by, for example, targeting two different flea proteins.

Examples of multivalent protective compounds include, but are not limited to, a SPI protein of the present invention attached to one or more compounds protective against one or more flea compounds. Preferred second compounds are proteinaceous compounds that effect active immunization (e.g., antigen vaccines), passive immunization (e.g., antibodies), or that otherwise inhibit a hematophagous ectoparasite activity that when inhibited can reduce hematophagous ectoparasite burden on and around an animal. Examples of second compounds include a compound that inhibits binding between a flea protein and its ligand (e.g., a compound that inhibits flea ATPase activity or a compound that inhibits binding of a peptide or steroid hormone to its receptor), a compound that inhibits hormone (including peptide or steroid hormone) synthesis, a compound that inhibits vitellogenesis (including production of vitellin and/or transport and maturation thereof into a major egg yolk protein), a compound that inhibits fat body function, a compound that inhibits muscle action, a compound that inhibits the nervous system, a compound that inhibits the immune system and/or a compound that inhibits flea feeding. Particular examples of second compounds include, but are not limited to, serine proteases, cysteine proteases, aminopeptidases, calreticulins and esterases, as well as antibodies and inhibitors of such proteins. In one embodiment, a flea SPI protein of the present invention is attached to one or more additional compounds protective against hematophagous ectoparasite infestation. In another embodiment, one or more protective compounds, such as those listed above, can be included in a multivalent vaccine comprising a flea SPI protein of the present invention and one or more other protective molecules as separate compounds.

A preferred flea SPI protein of the present invention is encoded by a nucleic acid molecule that hybridizes under stringent hybridization conditions with at least one of the following nucleic acid molecules: $nfSPI1_{1584}$, $nfSPI1_{1191}$, $nfSPI1_{376}$, $nfSPI2_{1358}$, $nfSPI2_{1197}$, $nfSPI2_{376}$, $nfSPI3_{1838}$, $nfSPI3_{1260}$, $nfSPI3_{391}$, $nfSPI4_{1414}$, $nfSPI4_{1179}$, $nfSPI4_{376}nfSPI5_{1492}$, $nfSPI5_{1194}$, $nfSPI5_{376}$, $nfSPI6_{1454}$, $nfSPI6_{1119}$ and $nfSPI6_{376}$. A further preferred isolated protein is encoded by a nucleic acid molecule that hybridizes under stringent hybridization conditions with a nucleic acid molecule having nucleic acid sequence SEQ ID NO:3, SEQ ID NO:5, SEQ ID NO:9, SEQ ID NO:11, SEQ ID NO:15, SEQ ID NO:17, SEQ ID NO:21, SEQ ID NO:23, SEQ ID NO:27 SEQ ID NO:29, SEQ ID NO:33 and SEQ ID NO:35.

Translation of SEQ ID NO:1 suggests that nucleic acid molecule $nfSPI1_{1584}$ encodes a full-length flea protein of about 397 amino acids, referred to herein as $PfSPI1_{397}$, represented by SEQ ID NO:2, assuming an open reading frame having an initiation (start) codon spanning from about nucleotide 136 through about nucleotide 138 of SEQ ID NO:1 and a termination (stop) codon spanning from about nucleotide 1327 through about nucleotide 1329 of SEQ ID NO:1. The coding region encoding $PfSPI1_{397}$ is represented by nucleic acid molecule $nfSPI1_{1191}$, having a coding strand with the nucleic acid sequence represented by SEQ ID NO:4 and a complementary strand with the nucleic acid sequence represented by SEQ ID NO:5. The deduced amino acid sequence SEQ ID NO:2 suggests a protein having a molecular weight of about 44.4 kilodaltons (kD) and an estimated pI of about 4.97. Analysis of SEQ ID NO:2 suggests the presence of a signal peptide encoded by a stretch of amino acids spanning from about amino acid 1 through about amino acid 21. The proposed mature protein, denoted herein as $PfSPI1_{376}$, contains about 376 amino acids which is represented herein as SEQ ID NO:6. The amino acid sequence of flea $PfSPI1_{376}$ (i.e. SEQ ID NO:6) predicts that $PfSPI1_{376}$ has an estimated molecular weight of about 42.1 kD, an estimated pI of about 4.90, and a predicted asparagine-linked glycosylation site extending from about amino acid 252 to about amino acid 254.

Comparison of amino acid sequence SEQ ID NO:2 (i.e., the amino acid sequence of $PfSPI1_{397}$) with amino acid sequences reported in GenBank indicates that SEQ ID NO:2 showed the most homology, i.e., about 36% identity, with GenBank accession number 1378131, a serpin protein from *Manduca sexta*.

Translation of SEQ ID NO:7 suggests that nucleic acid molecule $nfSPI2_{1358}$ encodes a non-full-length flea SPI protein of about 399 amino acids, referred to herein as $PfSPI2_{399}$, represented by SEQ ID NO:8, assuming an open reading frame having a first in-frame codon spanning from about nucleotide 2 through about nucleotide 4 of SEQ ID NO:7 and a termination codon spanning from about nucleotide 1199 through about nucleotide 1201 of SEQ ID NO:7. The coding region encoding $PfSPI2_{399}$ is represented by nucleic acid molecule $nfSPI2_{1197}$, having a coding strand with the nucleic acid sequence represented by SEQ ID NO:10 and a complementary strand with the nucleic acid sequence represented by SEQ ID NO:11. Analysis of SEQ ID NO:8 suggests the presence of a partial signal peptide encoded by a stretch of amino acids spanning from about amino acid 1 through about amino acid 23. The proposed mature protein, denoted herein as $PfSPI2_{376}$, contains about 376 amino acids which is represented herein as SEQ ID NO:12. The amino acid sequence of flea $PfSPI1_{376}$ (i.e. SEQ ID NO:12) predicts that $PfSPI2_{376}$ has an estimated molecular weight of about 42.1 kD, an estimated pI of about 4.87, and a predicted asparagine-linked glycosylation site extending from about amino acid 252 to about amino acid 254.

Comparison of amino acid sequence SEQ ID NO:8 (i.e., the amino acid sequence of $PfSPI2_{399}$) with amino acid sequences reported in GenBank indicates that SEQ ID NO:8, showed the most homology, i.e., about 36% identity, with GenBank accession number 1345616, a serpin protein from *Homo sapiens*.

Translation of SEQ ID NO:13 suggests that nucleic acid molecule $nfSPI3_{1838}$ encodes a full-length flea SPI protein of about 420 amino acids, referred to herein as $PfSPI3_{420}$, represented by SEQ ID NO:14, assuming an open reading frame having an initiation codon spanning from about nucleotide 306 through about nucleotide 308 of SEQ ID NO:13 and a termination codon spanning from about nucleotide 1566 through about nucleotide 1568 of SEQ ID NO:13. The coding region encoding $PfSPI3_{420}$ is represented by nucleic acid molecule $nfSPI3_{1260}$, having a coding strand with the nucleic acid sequence represented by SEQ ID NO:16 and a complementary strand with the nucleic acid sequence represented by SEQ ID NO:17. The deduced amino acid sequence SEQ ID NO:14 suggests a protein having a molecular weight of about 47.1 kilodaltons (kD) and an estimated pI of about 4.72. Analysis of SEQ ID NO:14 suggests the presence of a signal peptide encoded by a stretch of amino acids spanning from about amino acid 1 through about amino acid 30. The proposed mature protein, denoted herein as $PfSPI3_{390}$, contains about 390 amino acids which is represented herein as SEQ ID NO:18. The amino acid sequence of flea $PfSPI3_{390}$ (i.e. SEQ ID NO:18) predicts that $PfSPI3_{390}$ has an estimated molecular weight of about 43.7 kD, an estimated pI of about 4.63, and two predicted asparagine-linked glycosylation sites extending from about amino acid 252 to about amino acid 254 and from about amino acid 369 to about amino acid 371.

Comparison of amino acid sequence SEQ ID NO:14 (i.e., the amino acid sequence of $PfSPI3_{420}$) with amino acid sequences reported in GenBank indicates that SEQ ID NO:14, showed the most homology, i.e., about 35% identity, with GenBank accession number 1345616, a serpin protein from *Homo sapiens*.

Translation of SEQ ID NO:19 suggests that nucleic acid molecule $nfSPI4_{1414}$ encodes a non-full-length flea SPI protein of about 393 amino acids, referred to herein as $PfSPI4_{393}$, represented by SEQ ID NO:20, assuming an open reading frame having a first in-frame codon spanning from about nucleotide 2 through about nucleotide 4 of SEQ ID NO:19 and a termination codon spanning from about nucleotide 118 1 through about nucleotide 1183 of SEQ ID NO:19. The coding region encoding $PfSPI4_{393}$, is represented by nucleic acid molecule $nfSPI4_{1179}$, having a coding strand with the nucleic acid sequence represented by SEQ ID NO:22 and a complementary strand with the nucleic acid sequence represented by SEQ ID NO:23. Analysis of SEQ ID NO:20 suggests the presence of a partial signal peptide encoded by a stretch of amino acids spanning from about amino acid 1 through about amino acid 17. The proposed mature protein, denoted herein as $PfSPI4_{376}$, contains about 376 amino acids which is represented herein as SEQ ID NO:24. The amino acid sequence of flea $PfSPI4_{376}$ (i.e. SEQ ID NO:24) predicts that $PfSPI4_{376}$ has an estimated molecular weight of about 42.2 kD, an estimated pI of about 5.31, and a predicted asparagine-linked glycosylation site extending from about amino acid 252 to about amino acid 254.

Comparison of amino acid sequence SEQ ID NO:20 (i.e., the amino acid sequence of PfSPI4$_{393}$) with amino acid sequences reported in GenBank indicates that SEQ ID NO:20, showed the most homology, i.e., about 38% identity, with GenBank accession number 1345616, a serpin protein from *Homo sapiens*.

Translation of SEQ ID NO:25 suggests that nucleic acid molecule nfSPI5$_{1492}$ encodes a non-full-length flea SPI protein of about 398 amino acids, referred to herein as PfSPI5$_{398}$, represented by SEQ ID NO:26, assuming an open reading frame having a first in-frame codon spanning from about nucleotide 3 through about nucleotide 5 of SEQ ID NO:25 and a termination codon spanning from about nucleotide 1197 through about nucleotide 1199 of SEQ ID NO:25. The coding region encoding PfSPI5$_{398}$, is represented by nucleic acid molecule nfSPI5$_{1194}$, having a coding strand with the nucleic acid sequence represented by SEQ ID NO:28 and a complementary strand with the nucleic acid sequence represented by SEQ ID NO:29. Analysis of SEQ ID NO:26 suggests the presence of a partial signal peptide encoded by a stretch of amino acids spanning from about amino acid 1 through about amino acid 22. The proposed mature protein, denoted herein as PfSPI5$_{376}$, contains about 376 amino acids which is represented herein as SEQ ID NO:30. The amino acid sequence of flea PfSPI5$_{376}$ (i.e. SEQ ID NO:30) predicts that PfSPI5$_{376}$ has an estimated molecular weight of about 42.3 kD, an estimated pI of about 5.31 and a predicted asparagine-linked glycosylation site extending from about amino acid 252 to about amino acid 254.

Comparison of amino acid sequence SEQ ID NO:26 (i.e., the amino acid sequence of PfSPI5$_{398}$) with amino acid sequences reported in GenBank indicates that SEQ ID NO:26 showed the most homology, i.e., about 38% identity with GenBank accession number 1345616, a serpin protein from *Homo sapiens*.

Translation of SEQ ID NO:3 1 suggests that nucleic acid molecule nfSPI6$_{1454}$ encodes a full-length flea SPI protein of about 397 amino acids, referred to herein as PfSPI6$_{397}$, represented by SEQ ID NO:32, assuming an open reading frame having an initiation codon spanning from about nucleotide 20 through about nucleotide 22 of SEQ ID NO:31 and a termination codon spanning from about nucleotide 1211 through about nucleotide 1213 of SEQ ID NO:31. The coding region encoding PfSPI6$_{397}$ is represented by nucleic acid molecule nfSPI6$_{1191}$, having a coding strand with the nucleic acid sequence represented by SEQ ID NO:34 and a complementary strand with the nucleic acid sequence represented by SEQ ID NO:35. The deduced amino acid sequence SEQ ID NO:32 suggests a protein having a molecular weight of about 44.4 kilodaltons (kD) and an estimated pI of about 4.90. Analysis of SEQ ID NO:32 suggests the presence of a signal peptide encoded by a stretch of amino acids spanning from about amino acid 1 through about amino acid 21. The proposed mature protein, denoted herein as PfSPI6$_{376}$, contains about 376 amino acids which is represented herein as SEQ ID NO:36. The amino acid sequence of flea PfSPI6$_{376}$ (i.e. SEQ ID NO:36) predicts that PfSPI6$_{376}$ has an estimated molecular weight of about 42.1 kD, an estimated pI of about 4.84, and a predicted asparagine-linked glycosylation site extending from about amino acid 252 to about amino acid 254.

Comparison of amino acid sequence SEQ ID NO:32 (i.e., the amino acid sequence of PfSPI6$_{397}$) with amino acid sequences reported in GenBank indicates that SEQ ID NO:32 showed the most homology, i.e., about 36% identity with GenBank accession number 1378131, a serpin protein from *Manduca sexta*.

More preferred flea SPI proteins of the present invention include proteins comprising amino acid sequences that are at least about 40%, preferably at least about 50%, more preferably at least about 60%, more preferably at least about 70%, more preferably at least about 80%, and even more preferably at least about 90%, identical to amino acid sequence SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO:30, SEQ ID NO:32 and/or SEQ ID NO:36.

More preferred flea SPI proteins of the present invention include proteins encoded by a nucleic acid molecule comprising at least a portion of nfSPI1$_{1584}$, nfSPI2$_{1358}$, nfSPI3$_{1838}$, nfSPI4$_{1414}$, nfSPI5$_{1492}$, and nfSPI6$_{1454}$, or of allelic variants of such nucleic acid molecules. More preferred is a SPI protein encoded by nfSPI1$_{1584}$, nfSPI1$_{1191}$, nfSPI1$_{376}$, nfSPI2$_{1358}$, nfSPI2$_{1197}$, nfSPI2$_{376}$, nfSPI3$_{1838}$, nfSPI3$_{1260}$, nfSPI3$_{391}$, nfSPI4$_{1414}$, nfSPI4$_{1179}$, nfSPI4$_{376}$, nfSPI5$_{1492}$, nfSPI5$_{1194}$, nfSPI5$_{376}$, nfSPI6$_{1454}$, nfSPI6$_{1191}$, or nfSPI6$_{376}$, or by an allelic variant of such nucleic acid molecules. Particularly preferred flea SPI proteins are PfSPI1$_{397}$, PfSPI1$_{376}$, PfSPI2$_{399}$, PfSPI2$_{376}$, PfSPI3$_{420}$, PfSPI3$_{391}$, PfSPI4$_{393}$, PfSPI4$_{376}$, PfSPI5$_{398}$, PfSPI5$_{376}$, PfSPI6$_{397}$ and PfSPI6$_{376}$.

In one embodiment, a preferred SPI protein of the present invention is encoded by at least a portion of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31 and/or SEQ ID NO:34, and, as such, has an amino acid sequence that includes at least a portion of SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO30, SEQ ID NO:32 and SEQ ID NO:36, respectively.

Also preferred is a protein encoded by an allelic variant of a nucleic acid molecule comprising at least a portion of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31 and/or SEQ ID NO:34. Particularly preferred SPI proteins of the present invention include SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO30, SEQ ID NO:32 and SEQ ID NO:36 (including, but not limited to, the proteins consisting of such sequences, fusion proteins and multivalent proteins) and proteins encoded by allelic variants of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31 and/or SEQ ID NO:34.

Another embodiment of the present invention is an isolated nucleic acid molecule that hybridizes under stringent hybridization conditions with a *C. felis* SPI gene. The identifying characteristics of such a gene are heretofore described. A nucleic acid molecule of the present invention can include an isolated natural flea SPI gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with a *C. felis* SPI gene under stringent hybridization conditions.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated flea SPI nucleic acid molecule of the present invention can be isolated from its natural source or can be produced using recombinant DNA technology (e.g., polymerase chain reaction (PCR) amplification, cloning) or chemical synthesis. Isolated SPI nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a SPI protein of the present invention or to form stable hybrids under stringent conditions with natural gene isolates.

A flea SPI nucleic acid molecule homolog can be produced using a number of methods known to those skilled in the art (see, for example, Sambrook et al., ibid.). For example, nucleic acid molecules can be modified using a variety of techniques including, but not limited to, classic mutagenesis and recombinant DNA techniques (e.g., site-directed mutagenesis, chemical treatment, restriction enzyme cleavage, ligation of nucleic acid fragments and/or PCR amplification), synthesis of oligonucleotide mixtures and ligation of mixture groups to "build" a mixture of nucleic acid molecules and combinations thereof. Nucleic acid molecule homologs can be selected by hybridization with a C. felis SPI gene or by screening for function of a protein encoded by the nucleic acid molecule (e.g., ability to elicit an immune response against at least one epitope of a flea SPI protein or has at least some serine protease inhibitor activity).

An isolated nucleic acid molecule of the present invention can include a nucleic acid sequence that encodes at least one flea SPI protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea SPI protein.

A preferred nucleic acid molecule of the present invention, when administered to an animal, is capable of protecting that animal from infestation by a hematophagous ectoparasite. As will be disclosed in more detail below, such a nucleic acid molecule can be, or can encode, an antisense RNA, a molecule capable of triple helix formation, a ribozyme, or other nucleic acid-based drug compound. In additional embodiments, a nucleic acid molecule of the present invention can encode a protective protein (e.g., a SPI protein of the present invention), the nucleic acid molecule being delivered to the animal, for example, by direct injection (i.e, as a naked nucleic acid) or in a vehicle such as a recombinant virus vaccine or a recombinant cell vaccine.

One embodiment of the present invention is a SPI nucleic acid molecule that hybridizes under stringent hybridization conditions with nucleic acid molecule nfSPI1 $_{1584}$ and preferably with a nucleic acid molecule having nucleic acid sequence SEQ ID NO:1 and/or SEQ ID NO:3.

Another embodiment of the present invention is a SPI nucleic acid molecule that hybridizes under stringent hybridization conditions with nucleic acid molecule nfSPI2$_{1358}$, and preferably with a nucleic acid molecule having nucleic acid sequence SEQ ID NO:7 and/or SEQ ID NO:9.

Another embodiment of the present invention is a SPI nucleic acid molecule that hybridizes under stringent hybridization conditions with nucleic acid molecule nfSPI3$_{1838}$ and preferably with a nucleic acid molecule having nucleic acid sequence SEQ ID NO:13 and/or SEQ ID NO:15.

Another embodiment of the present invention is a SPI nucleic acid molecule that hybridizes under stringent hybridization conditions with nucleic acid molecule nfSPI4$_{1414}$ and preferably with a nucleic acid molecule having nucleic acid sequence SEQ ID NO:19 and/or SEQ ID NO:21.

Another embodiment of the present invention is a SPI nucleic acid molecule that hybridizes under stringent hybridization conditions with nucleic acid molecule nfSPI5$_{1492}$ and preferably with a nucleic acid molecule having nucleic acid sequence SEQ ID NO:25 and/or SEQ ID NO:27.

Another embodiment of the present invention is a SPI nucleic acid molecule that hybridizes under stringent hybridization conditions with nucleic acid molecule nfSPI6$_{1454}$ and preferably with a nucleic acid molecule having nucleic acid sequence SEQ ID NO:31 and/or SEQ ID NO:33.

Comparison of nucleic acid sequence SEQ ID NO:4 (i.e., the nucleic acid sequence of the coding strand of nfSPI1$_{1191}$) with nucleic acid sequences reported in GenBank indicates that SEQ ID NO:4 showed the most homology, i.e., about 55% identity, with accession number L20792, a putative serine proteinase inhibitor (serpin 1, exon 9 copy 2) gene of *Manduca sexta*.

Comparison of nucleic acid sequence SEQ ID NO:10 (i.e., the nucleic acid sequence of the coding strand of nfSPI2$_{1197}$) with nucleic acid sequences reported in GenBank indicates that SEQ ID NO:10 showed the most homology, i.e., about 43% identity, with accession number L20790, a putative serine proteinase inhibitor gene (serpin 1, exon 9 copy 1) of *Manduca sexta*.

Comparison of nucleic acid sequence SEQ ID NO:16 (i.e., the nucleic acid sequence of the coding strand of nfSPI3 1260) with nucleic acid sequences reported in GenBank indicates that SEQ ID NO:16 showed the most homology, i.e., about 52% identity, with accession number L20792, a putative serine proteinase inhibitor gene (serpin 1, exon 9 copy 2) of *Manduca sexta*.

Comparison of nucleic acid sequence SEQ ID NO:22 (i.e., the nucleic acid sequence of the coding strand of nfSPI4$_{1179}$) with nucleic acid sequences reported in GenBank indicates that SEQ ID NO:22 showed the most homology, i.e., about 55% identity, with accession number L20793, a putative serine proteinase inhibitor gene (serpin 1, exon 9 unknown copy number) of *Manduca sexta*.

Comparison of nucleic acid sequence SEQ ID NO:28 (i.e., the nucleic acid sequence of the coding strand of nfSPI5$_{1194}$) with nucleic acid sequences reported in GenBank indicates that SEQ ID NO:28 showed the most homology, i.e., about 45% identity, with accession number L20790, a putative serine proteinase inhibitor gene (serpin 1, exon 9 copy 1) of *Manduca sexta*.

Comparison of nucleic acid sequence SEQ ID NO:34 (i.e., the nucleic acid sequence of the coding strand of nfSPI6$_{1191}$) with nucleic acid sequences reported in GenBank indicates that SEQ ID NO:34 showed the most homology, i.e., about 55% identity, with accession number L20792, a putative serine proteinase inhibitor gene (serpin 1, exon 9 copy 2) of *Manduca sexta*.

Preferred flea SPI nucleic acid molecules include nucleic acid molecules having a nucleic acid sequence that is at least about 60%, preferably at least about 70%, more preferably at least about 80%, even more preferably at least about 90% and even more preferably at least about 95% identical to nucleic acid sequence SEQ ID NO:1, SEQ ID NO:3, SEQ ID NO:4, SEQ ID NO:5, SEQ ID NO:7, SEQ ID NO:9, SEQ ID NO:10, SEQ ID NO:11, SEQ ID NO:13, SEQ ID NO:15, SEQ ID NO:16, SEQ ID NO:17, SEQ ID NO:19, SEQ ID NO:21, SEQ ID NO:22, SEQ ID NO:23, SEQ ID NO:25, SEQ ID NO:27, SEQ ID NO:28, SEQ ID NO:29, SEQ ID NO:31, SEQ ID NO:33, SEQ ID NO:34, and/or SEQ ID 35.

Another preferred nucleic acid molecule of the present invention includes at least a portion of nucleic acid sequence SEQ ID NO:1, SEQ ID NO:3, SEQ ID NO:4, SEQ ID NO:5, SEQ ID NO:7, SEQ ID NO:9, SEQ ID NO:10, SEQ ID NO:11, SEQ ID NO:13, SEQ ID NO:15, SEQ ID NO:16, SEQ ID NO:17, SEQ ID NO:19, SEQ ID NO:21, SEQ ID NO:22, SEQ ID NO:23, SEQ ID NO:25, SEQ ID NO:27, SEQ ID NO:28, SEQ ID NO:29, SEQ ID NO:31, SEQ ID NO:33. SEQ ID NO:34 and/or SEQ ID 35, that is capable of hybridizing to a *C. felis* SPI gene of the present invention, as well as allelic variants thereof. A more preferred nucleic acid molecule includes the nucleic acid sequence SEQ ID NO:1, SEQ ID NO:3, SEQ ID NO:4, SEQ ID NO:5, SEQ ID NO:7, SEQ ID NO:9, SEQ ID NO:10, SEQ ID NO:11, SEQ ID NO:13, SEQ ID NO:15, SEQ ID NO:16, SEQ ID NO:17, SEQ ID NO:19, SEQ ID NO:21, SEQ ID NO:22, SEQ ID NO:23, SEQ ID NO:25, SEQ ID NO:27, SEQ ID NO:28, SEQ ID NO:29, SEQ ID NO:31, SEQ ID NO:33. SEQ ID NO:34 and/or SEQ ID 35, as well as allelic variants thereof. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include $nfSPI1_{1584}$, $nfSPI1_{1191}$, $nfSP1_{376}$, $nfSPI2_{1358}$, $nfSPI2_{1197}$, $nfSPI2_{376}$, $nfSPI3_{1838}$, $nfSPI3_{1260}$, $nfSPI3_{391}$, $nfSPI4_{1414}$, $nfSPI4_{1179}$, $nfSPI4_{376}$, $nfSPI5_{1492}$, $nfSPI5_{1194}$, $nfSPI5_{376}$, $nfSPI6_{1454}$, $nfSPI6_{1191}$ and $nfSPI6_{376}$.

The present invention also includes a nucleic acid molecule encoding a protein having at least a portion of SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO:30, SEQ ID NO:32 and SEQ ID NO:36, including nucleic acid molecules that have been modified to accommodate codon usage properties of the cells in which such nucleic acid molecules are to be expressed.

Knowing the nucleic acid sequences of certain flea SPI nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain SPI nucleic acid molecules from other hematophagous ectoparasites. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include flea hemocyte (i.e., cells found in flea hemolymph), pre-pupal, mixed instar (i.e., a combination of $1^{st}$ instar larval, $2^{nd}$ instar larval, $3^{rd}$ instar larval tissue), or fed or unfed adult cDNA libraries as well as genomic DNA libraries. Similarly, preferred DNA sources to screen or from which to amplify nucleic acid molecules include flea hemocyte, pre-pupal, mixed instar, or fed or unfed adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising flea SPI genes or other flea SPI nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit SPI protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of flea SPI nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, ompllpp, rrnB, bacteriophage lambda(such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as, *C. felis*.

Suitable and preferred nucleic acid molecules to include in recombinant vectors of the present invention are as disclosed herein. Preferred nucleic acid molecules to include in recombinant vectors, and particularly in recombinant molecules, include $nfSPI1_{1584}$, $nfSPI1_{1191}$, $nfSPI1_{376}$, $nfSPI2_{1358}$, $nfSPI2_{1197}$, $nfSPI2_{376}$, $nfSPI3_{1838}$, $nfSPI3_{1260}$, $nfSPI3_{391}$, $nfSPI4_{1414}$, $nfSPI4_{1179}$, $nfSPI4_{376}$, $nfSPI5_{1492}$, $nfSPI5_{1194}$, $nfSPI5_{376}$, $nfSPI6_{1454}$, $nfSPI6_{1191}$ and $nfSPI6_{376}$. Particularly preferred recombinant molecules of the present invention include $p\lambda P_R$-$nfSPI2_{1139}$, $p\lambda P_R$-$nfSPI3_{1179}$, $p\lambda P_R$-$nfSPI4_{1140}$, $p\lambda P_R$-$nfSPI5_{1492}$ and $p\lambda P_R$-$nfSPI6_{1136}$, the production of which are described in the Examples section.

Recombinant molecules of the present invention may also (a) contain secretory signals (i.e., signal segment nucleic acid sequences) to enable an expressed flea protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include flea SPI nucleic acid molecules disclosed herein. Particularly preferred nucleic acid molecules with which to transform a cell include $nfSPI1_{1584}$, $nfSPI1_{1191}$, $nfSPI1_{376}$, $nfSPI2_{1358}$, $nfSPI2_{1197}$, $nfSPI2_{376}$, $nfSPI3_{1838}$, $nfSPI3_{1260}$, $nfSPI3_{391}$, $nfSPI4_{1414}$, $nfSPI4_{1179}$, $nfSPI4_{376}$, $nfSPI5_{1492}$, $nfSPI5_{1194}$, $nfSPI5_{376}$, $nfSPI6_{1454}$, $nfSPI6_{1191}$ and $nfSPI6_{376}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing flea SPI proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacterial, yeast, parasite, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_x$3987 and SR-11 $_x$4072; *Spodopterafrugiperda; Trichoplusia ni;* BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK[31] cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include $p\lambda P_R$-nfSPI2$_{1139}$, $p\lambda P_R$-nSPI3$_{1179}$, $p\lambda P_R$-nfSPI4$_{1140}$, $p\lambda P_R$-nfSPI5$_{1492}$ and $p\lambda P_R$-nfSPI6$_{1136}$.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein. Particularly preferred recombinant cells include *E.coli*HB:$p\lambda P_R$-nfSPI2$_{1139}$, *E.coli*HB:$p\lambda P_R$-nfSPI3$_{1179}$, *E.coli*HB:$p\lambda P_R$-nfSPI4$_{1140}$, *E.coli*BM:$p\lambda P_R$-nfSPI5$_{1492}$ and *E.coli*BM:$p\lambda P_R$-nfSPI6$_{1136}$. Details regarding the production of these recombinant cells are disclosed herein.

Recombinant cells of the present invention can also be co-transformed with one or more recombinant molecules including flea SPI nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated SPI proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a flea SPI protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea SPI protein of the present invention or a mimetope thereof (i.e., anti-flea SPI antibodies). As used herein, the term "selectively binds to" a SPI protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-flea SPI antibody preferably selectively binds to a flea SPI protein in such a way as to reduce the activity of that protein.

Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce flea SPI proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from hematophagous ectoparasites susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to hematophagous ectoparasite such as those disclosed herein in order to directly kill such hematophagous ectoparasites. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from infestation by hematophagous ectoparasites. Therapeutic compositions of the present invention include at least one of the following protective compounds: an isolated flea SPI protein (including a peptide of a flea SPI protein capable of inhibiting serine protease activity), a mimetope of a flea SPI protein, an isolated SPI nucleic acid molecule that hybridizes under stringent hybridization conditions with a *Ctenocephalides felis* SPI gene, an isolated antibody that selectively binds to a flea SPI protein, and inhibitors of flea SPI activity (including flea SPI protein substrate analogs, such as serine proteases or serine protease analogs). Preferred hematophagous ectoparasites to target are heretofore disclosed. Examples of protective compounds (e.g., proteins, mimetopes, nucleic acid molecules, antibodies, and inhibitors) are disclosed herein.

Suitable inhibitors of SPI activity are compounds that interact directly with a SPI protein active site, thereby inhibiting that SPI's activity, usually by binding to or otherwise interacting with or otherwise modifying the SPI's active site. SPI inhibitors can also interact with other regions of the SPI protein to inhibit SPI activity, for example, by allosteric interaction. Inhibitors of SPIs are usually relatively small compounds and as such differ from anti-SPI antibodies. Preferably, a SPI inhibitor of the present invention is identified by its ability to bind to, or otherwise interact with, a flea SPI protein, thereby inhibiting the activity of the flea SPI.

Inhibitors of a SPI can be used directly as compounds in compositions of the present invention to treat animals as long as such compounds are not harmful to host animals being treated. Inhibitors of a SPI protein can also be used to identify preferred types of flea SPI proteins to target using compositions of the present invention, for example by affinity chromatography. Preferred inhibitors of a SPI of the present invention include, but are not limited to, flea SPI substrate analogs, and other molecules that bind to a flea SPI (e.g., to an allosteric site) in such a manner that SPI activity of the flea SPI is inhibited. A SPI substrate analog refers to a compound that interacts with (e.g., binds to, associates with, modifies) the active site of a SPI protein. A preferred SPI substrate analog inhibits SPI activity. SPI substrate analogs can be of any inorganic or organic composition, and, as such, can be, but are not limited to, peptides, nucleic acids, and peptidomimetic compounds. SPI substrate analogs can be, but need not be, structurally similar to a SPI protein's natural substrate as long as they can interact with the active site of that SPI protein. SPI substrate analogs can be designed using computer-generated structures of SPI proteins of the present invention or computer structures of SPI proteins' natural substrates. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a flea SPI or anti-flea serine protease antibody). A preferred SPI substrate analog is a peptidomimetic compound (i.e., a compound that is structurally and/or functionally similar to a natural substrate of a SPI of the present invention, particularly to the region of the substrate that interacts with the SPI active site, but that inhibits SPI activity upon interacting with the SPI active site).

SPI peptides, mimetopes and substrate analogs, as well as other protective compounds, can be used directly as compounds in compositions of the present invention to treat animals as long as such compounds are not harmful to the animals being treated.

The present invention also includes a therapeutic composition comprising at least one flea SPI-based compound of the present invention in combination with at least one additional compound protective against hematophagous ectoparasite infestation. Examples of such compounds are disclosed herein.

In one embodiment, a therapeutic composition of the present invention can be used to protect an animal from hematophagous ectoparasite infestation by administering such composition to a hematophagous ectoparasite, such as to a flea, in order to prevent infestation. Such administration could be orally or by developing transgenic vectors capable of producing at least one therapeutic composition of the present invention. In another embodiment, a hematophagous ectoparasite, such as a flea, can ingest therapeutic compositions, or products thereof, present in the blood of a host animal that has been administered a therapeutic composition of the present invention.

Compositions of the present invention can be administered to any animal susceptible to hematophagous ectoparasite infestation (i.e., a host animal), including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets and/or economic food animals, being more preferred. Particularly preferred animals to protect are cats and dogs.

In accordance with the present invention, a host animal (i.e., an animal that is or is capable of being infested with a hematophagous ectoparasite) is treated by administering to the animal a therapeutic composition of the present invention in such a manner that the composition itself (e.g., an inhibitor of a SPI protein, a SPI synthesis suppressor (i.e., a compound that decreases the production of SPI in the hematophagous ectoparasite), an SPI mimetope, or an anti-hematophagous ectoparasite SPI antibody) or a product generated by the animal in response to administration of the composition (e.g., antibodies produced in response to a flea SPI protein or nucleic acid molecule vaccine, or conversion of an inactive inhibitor "prodrug" to an active inhibitor of a SPI protein) ultimately enters the hematophagous ectoparasite. A host animal is preferably treated in such a way that the compound or product thereof enters the blood stream of the animal. Hematophagous ectoparasites are then exposed to the composition or product when they feed from the animal. For example, flea SPI protein inhibitors administered to an animal are administered in such a way that the inhibitors enter the blood stream of the animal, where they can be taken up by feeding fleas. In another embodiment, when a host animal is administered a flea SPI protein or nucleic acid molecule vaccine, the treated animal mounts an immune response resulting in the production of antibodies against the SPI protein (i.e., anti-flea SPI antibodies) which circulate in the animal's blood stream and are taken up by hematophagous ectoparasites upon feeding. Blood taken up by hematophagous ectoparasites enters the hematophagous ectoparasites where compounds of the present invention, or products thereof, such as anti-flea SPI antibodies, flea SPI protein inhibitors, flea mimetopes and/or SPI synthesis suppressors, interact with, and reduce SPI protein activity in the hematophagous ectoparasite.

The present invention also includes the ability to reduce larval hematophagous ectoparasite infestation in that when hematophagous ectoparasites feed from a host animal that has been administered a therapeutic composition of the present invention, at least a portion of compounds of the present invention, or products thereof, in the blood taken up by the hematophagous ectoparasite are excreted by the hematophagous ectoparasite in feces, which is subsequently ingested by hematophagous ectoparasite larvae. In particular, it is of note that flea larvae obtain most, if not all, of their nutrition from flea feces.

In accordance with the present invention, reducing SPI protein activity in a hematophagous ectoparasite can lead to a number of outcomes that reduce hematophagous ectoparasite burden on treated animals and their surrounding environments. Such outcomes include, but are not limited to, (a) reducing the viability of hematophagous ectoparasites that feed from the treated animal, (b) reducing the fecundity of female hematophagous ectoparasites that feed from the treated animal, (c) reducing the reproductive capacity of male hematophagous ectoparasites that feed from the treated animal, (d) reducing the viability of eggs laid by female hematophagous ectoparasites that feed from the treated animal, (e) altering the blood feeding behavior of hematophagous ectoparasites that feed from the treated animal (e.g., hematophagous ectoparasites take up less volume per feeding or feed less frequently), (f) reducing the viability of hematophagous ectoparasite larvae (e.g., by decreasing feeding behavior, inhibiting growth, inhibiting (e.g., slowing or blocking) molting, and/or otherwise inhibiting maturation to adults).

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal,—or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to protect an animal from hematophagous ectoparasite infestation. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a bicistronic recombinant molecule having, for example one or more internal ribosome entry sites. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccines ranges from about 1 nanogram (ng) to about 100 $\mu$g, depending on the route of administration and/or method of delivery, as can be determined by those skilled in the art. Suitable delivery methods include, for example, by injection, as drops, aerosolized and/or topically. Naked DNA of the present invention can be contained in an aqueous excipient (e.g., phosphate buffered saline) alone or a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines is disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from hematophagous ectoparasite infestation. For example, a recombinant virus vaccine comprising a flea SPI nucleic acid molecule of the present invention is administered according to a protocol that results in the animal producing a sufficient immune response to protect itself from hematophagous ectoparasite infestation. A preferred single dose of a recombinant virus vaccine of the present invention is from about $1 \times 10^4$ to about $1 \times 10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from hematophagous ectoparasite infestation can be tested in a variety of ways including, but not limited to, detection of anti-flea SPI antibodies (using, for example, proteins or mimetopes of the present invention), detection of cellular immunity within the treated animal, or challenge of the treated animal with hematophagous ectoparasites to determine whether, for example, the feeding, fecundity or viability of the hematophagous ectoparasites feeding from the treated animal is disrupted. Challenge studies can include attachment of chambers containing fleas onto the skin of the treated animal. In one embodiment, therapeutic compositions can be tested in animal models such as mice. Such techniques are known to those skilled in the art.

One preferred embodiment of the present invention is the use of flea SPI proteins, mimetopes, nucleic acid molecules, antibodies and inhibitory compounds of the present invention, to protect an animal from hematophagous ectoparasite infestation. Preferred protective compounds of the present invention include, but are not limited to, an isolated flea SPI protein or a mimetope thereof, an isolated SPI nucleic acid molecule that hybridizes under stringent hybridization conditions with a *Ctenocephalides felis* SPI gene, an isolated antibody that selectively binds to a flea SPI and/or an inhibitor of flea SPI activity (such as, but not limited to, an SPI substrate analog). Additional protection may be obtained by administering additional protective compounds, including other proteins, nucleic acid molecules, antibodies and inhibitory compounds, as disclosed herein.

An inhibitor of SPI activity can be identified using flea SPI proteins of the present invention. One embodiment of the present invention is a method to identify a compound capable of inhibiting SPI activity of a flea. Such a method includes the steps of (a) contacting (e.g., combining, mixing) an isolated flea SPI protein, preferably a *C. felis* SPI protein, with a putative inhibitory compound under conditions in which, in the absence of the compound, the protein has SPI activity, and (b) determining if the putative inhibitory compound inhibits the SPI activity. Putative inhibitory compounds to screen include small organic molecules, antibodies (including mimetopes thereof) and substrate analogs. Methods to determine SPI activity are known to those skilled in the art.

The present invention also includes a test kit to identify a compound capable of inhibiting SPI activity of a flea. Such a test kit includes an isolated flea SPI protein, preferably a *C. felis* SPI protein, having SPI activity and a means for determining the extent of inhibition of SPI activity in the presence of (i.e., effected by) a putative inhibitory compound. Such compounds are also screened to identify those that are substantially not toxic in host animals.

SPI inhibitors isolated by such a method, and/or test kit, can be used to inhibit any SPI protein that is susceptible to such an inhibitor. Preferred SPI enzymes proteins to inhibit are those produced by fleas. A particularly preferred inhibitor of a SPI protein of the present invention is capable of protecting an animal from flea infestation. Effective amounts and dosing regimens can be determined using techniques known to those skilled in the art.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., and related references.

Example 1

This example describes the isolation of a protein fraction from flea prepupal larvae that was obtained by monitoring for carboxylesterase activity, which surprisingly, also contained flea serine protease inhibitor molecule epitopes of the present invention, discovered as described in Examples 2, 3 and 4 below.

A prepupal larval protein pool enriched for carboxylesterase activity was isolated as follows. About 17,000 bovine blood-fed prepupal larvae were collected and the larvae were homogenized in gut dissection buffer (50 mM Tris pH 8.0, 100 mM $CaCl_2$) by sonication in a disposable 50 ml conical centrifuge tube. Sonication entailed 4 bursts of 20 seconds each at a setting of 4 with a probe sonicator using, for example, a model W-380 Sonicator (available from Heat Systems-Ultrasonics, Inc., Farmingdale, N.Y.). The sonicate was clarified by centrifugation at 4000 rpm for 30 min. in a swinging bucket centrifuge; the supernatant was collected and centrifuged at 18,000 rpm for 30 min in a Sorvall SS-34 rotor (available from DuPont, Wilmington, Del.). The supernatant was recovered, and NaCl was added to a final concentration of 400 mM.

Serine proteases were removed from the supernatant using the following method. The supernatant was loaded onto a 5-ml column comprising p-aminobenzamidine cross-linked to Sepharose beads (available from Sigma Chemical Company, St. Louis, Mo.), previously equilibrated in benzamidine column buffer (50 mM Tris 8.0, 100 mM $CaCl_2$, 400 mM NaCl) and incubated overnight at 4° C. Unbound protein was slowly washed off and collected from the column with benzamidine column buffer until no protein was detectable by a Bradford Assay (available from Bio-Rad Laboratories, Hercules, Calf.). A total of about 43 ml was collected. The proteins in this pool were fractionated by precipitation in increasing percent saturation levels of ammonium sulfate.

The ammonium sulfate-precipitated protein fractions, as well as all subsequent protein fractions described in this example, were assayed for carboxylesterase activity by the following method. Samples of about 5 $\mu$l of each fraction were added to separate wells of a flat-bottomed microtiter plate (available from Becton Dickinson, Lincoln Park, N.J.). A control well was prepared by adding about 5 $\mu$l of Tris buffer to an empty well of the plate. About 95 $\mu$l of 25 mM Tris-HCl (pH 8.0) was then added to each sample to increase the volume in each well to about 100 $\mu$l. About 100 $\mu$l of 0.25 mM $\alpha$-napthyl acetate (available from Sigma) dissolved in 25 mM Tris-HCl (pH 8.0) was then added to each well. The plate was then incubated for about 15 min. at 37° C. Following the incubation, about 40 $\mu$l of 0.3% Fast Blue salt BN (tetrazotized o-dianisidine; available from Sigma), dissolved in 3.3% SDS in water was added to each well, giving a colorimetric reaction. Absorbance levels were measured using a model 7500 Microplate Reader (available from Cambridge Technology, Inc., Watertown, Mass.) set to 590 nm. Following subtraction of background absorbance, the resulting values gave a relative measure of carboxylesterase activity. Carboxylesterase activity was found in two of the ammonium sulfate-precipitated fractions. The first, which precipitated between about 0 and 60% ammonium sulfate saturation, was kept as a pool, and the second, which precipitated between about 60 and 80% ammonium sulfate saturation, was kept separately as a pool. Since the latter pool appeared to have higher activity at this point, the pools were treated separately until just prior to the final HPLC step described below, but at that point they were combined.

The two ammonium sulfate-precipitated protein pools were then subjected to cation exchange chromatography, performed as follows. Each protein pool was dialyzed two times against about 500 ml of 20 mM 2-(N-morpholino) ethanesulfonic acid (MES) buffer, pH 6.0, containing 10 mM NaCl and was then applied to a 40-ml chromatography column containing 10 ml of S-Sepharose Fast Flow cation exchange resin (available from Pharmacia Biochemicals, Piscataway, N.J.), previously equilibrated with MES buffer. Each column was rocked overnight at 4° C. to facilitate protein binding, and was then drained and washed with more MES buffer to remove all unbound protein in about 40 ml total volume. Following elution of the bound proteins, the bound and unbound protein fractions were tested for carboxylesterase activity as described above. Activity was found to reside in the unbound protein fractions from each column, which were then concentrated to about 5 ml using Centriprep® 30 centrifugal concentrators (available from Amicon, Beverly, Mass.).

The two concentrated protein pools were then subjected to anion exchange chromatography, performed as follows. Each pool was adjusted to about pH 7 by the addition of a small amount of 500 mM Tris buffer, pH 8, and was then applied, in about 1 to 1.5 ml aliquots, to a 4.5 mm×50 mm Poros 10 HQ anion exchange chromatography column (available from PerSeptive Biosystems, Cambridge, Mass.) equilibrated in 25 mM Tris, pH 6.8 (loading buffer). For each aliquot, the column was washed with the loading buffer, and bound proteins were eluted with a linear gradient of 0 to 1 M NaCl in 25 mM Tris buffer, pH 6.8. All column fractions were tested for carboxylesterase activity as described above. For each aliquot run on the column, the activity peak eluted in fractions 31–34, and at this point in the isolation, the activity levels appeared to be equivalent in both of the original ammonium sulfate-fractionated pools. Therefore, all column fractions containing carboxylesterase activity were combined into one pool. This pool was concentrated and diafiltered into about 1 ml of Tris-buffered saline (TBS).

The pooled protein preparation was then loaded onto a C1 reverse phase HPLC column (available from TosoHaas, Montgomeryville, Pa.), previously equilibrated with 19% acetonitrile containing 0.05% trifluoroacetic acid (TFA). The column was washed with the equilibration buffer to remove unbound proteins, and bound proteins were eluted from the column by a linear gradient from 19% acetonitrile containing 0.05% TFA to 95% acetonitrile containing 0.05% TFA. The column fractions were tested for carboxylesterase activity as described above, and the activity peak eluted in fractions 27–32. These fractions were combined, concentrated to near dryness using a Speed-Vac™ concentrator (available from Savant Instruments, Molbrook, N.Y.), and resuspended in phosphate-buffered saline (PBS) to a concentration of about 0.2 mg/ml. This isolated protein fraction is referred to herein as flea prepupal carboxylesterase fraction-1. Upon analysis by SDS-polyacrylamide gel electrophoresis (SDS-PAGE) and silver staining, flea prepupal carboxylesterase fraction-1 appeared to contain, in addition to the recognized carboxylesterase bands migrating at about 60 kD, a strong protein band migrating at about 40 kD.

Example 2

This Example describes the generation of polyclonal rabbit antiserum to flea prepupal carboxylesterase fraction-1.

Antibodies against flea prepupal carboxylesterase fraction-1 (the preparation of which is described in Example 1) were generated as follows. A rabbit was initially immunized subcutaneously and intradermally at multiple sites with a total of approximately 50 µg of flea prepupal carboxylesterase fraction-1 emulsified in Complete Freund's Adjuvant. On days 16 and 37 after the initial immunization, the rabbit was boosted intramuscularly with a total of approximately 50 µg of flea prepupal carboxylesterase fraction-1emulsified in Incomplete Freund's Adjuvant. The rabbit was bled on days 9, 29 and 50 after the initial immunization. Sera from the latter two bleeds, putatively containing antibodies to flea prepupal carboxylesterases, were used separately for immunoscreening experiments, as described in Example 3 below.

Example 3

This example describes the isolation, by immunoscreening, of nucleic acid molecules encoding flea serine protease inhibitor proteins of the present invention.

Surprisingly, six flea serine protease inhibitor nucleic acid molecules were isolated by their ability to encode proteins that selectively bound to at least one component of the immune serum collected from a rabbit immunized with flea prepupal carboxylesterase fraction-1, using the following method. A flea prepupal cDNA library was produced as follows. Total RNA was extracted from approximately 3,653 prepupal larvae using an acid-guanidinium-phenol-chloroform method similar to that described by Chomczynski et al., 1987, *Anal. Biochem.* 162, 156–159. Poly A+ selected RNA was separated from the total RNA preparation by oligo-dT cellulose chromatography using Poly(A) Quick® mRNA isolation kits (available from Stratagene Cloning Systems, La Jolla, Calf.), according to the method recommended by the manufacturer. A prepupal cDNA expression library was constructed in lambda Uni-ZAP™XR vector (available from Stratagene), using Stratagene's ZAP-cDNA Synthesis Kit® protocol. About 6.72 µg of prepupal poly A+ RNA was used to produce the prepupal library. The resultant prepupal library was amplified to a titer of about $3.5 \times 10^{10}$ pfu/ml with about 97% recombinants.

Using a modification of the protocol described in the picoBlue immunoscreening kit (available from Stratagene), the pre-pupal cDNA expression library was screened with the flea prepupal carboxylesterase fraction-1 immune rabbit serum, generated as described in Example 2. The protocol was modified in that the secondary peroxidase-conjugated antibody was detected with a chromogen substrate consisting of DAB (3,3' diaminobenzidine) plus cobalt (Sigma Fast, available from Sigma) following the manufacturer's instructions, except that tablets were dissolved in water at one half the recommended final concentration. Plaque lift membranes were placed in the substrate solution for about 2 minutes, rinsed in water, and then dried at room temperature. Immunoscreening of duplicate plaque lifts of the cDNA library with the same immune rabbit serum identified six clones containing flea nucleic acid molecules $nfSPI1_{1584}$, $nfSPI2_{1358}$, $nfSPI3_{1838}$, $nfSPI4_{1414}$, $nfSPI5_{1492}$, and $nfSPI6_{1454}$, respectively. Plaque purified clones including the flea nucleic acid molecules were converted into double stranded recombinant molecules, herein denoted as pβgal-$nfSPI1_{1584}$, pβgal-$nfSPI2_{1358}$, pβgal-$nfSPI3_{1838}$, pβgal-$nfSPI4_{1414}$, pβgal-$nfSPI5_{1492}$, and pβgal-$nfSPI6_{1454}$, using ExAssist™ helper phage and SOLR™ *E. coli* according to the in vivo excision protocol described in the Zap-cDNA Synthesis Kit (available from Stratagene). Double-stranded plasmid DNA was prepared using an alkaline lysis protocol, such as that described in Sambrook et al., ibid.

Example 4

This example describes the sequencing of several flea serine protease inhibitor nucleic acid molecules of the present invention.

The plasmid containing flea $nfSPI1_{1584}$, $nfSPI2_{1358}$, $nfSPI3_{1838}$, $nfSPI4_{1414}$, $nfSPI5_{1492}$, and $nfSPI6_{1454}$ were sequenced by the Sanger dideoxy chain termination method, using the PRISM™ Ready Dye Terminator Cycle Sequencing Kit with AmpliTaq® DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following their standard protocol. Samples were resuspended according to ABI protocols and were and run on a Perkin-Elmer ABI PRISM™ 377 Automated DNA Sequencer. DNA sequence analyses, including the compilation of sequences and the determination of open reading frames, were performed using either the DNAsis™ program (available from Hitachi Software, San Bruno, Calif.) or the MacVector™ program (available from the Eastman Kodak Company, New Haven, Conn.). Protein sequence analyses, including the determination of molecular weights and isoelectric points (pI) were performed using the MacVector™ program.

A. An about 1584-nucleotide consensus sequence of the entire flea $nfSPI1_{1584}$ DNA fragment was determined; the sequences of the two complementary strands are presented as SEQ ID NO:1 (the coding strand) and SEQ ID NO:3 (the complementary strand). The flea $nfSPI1_{1584}$ sequence contains a full length coding region. The apparent start and stop codons span nucleotides from about 136 through about 138 and from about 1327 through about 1329, respectively, of SEQ ID NO:1. A putative polyadenylation signal (5' AATAAA 3') is located in a region spanning from about nucleotide 1533 through about 1538 of SEQ ID NO:1.

Translation of SEQ ID NO:1 yields a protein of about 397 amino acids, denoted $PfSPI1_{397}$, the amino acid sequence of which is presented in SEQ ID NO:2. The nucleic acid molecule consisting of the coding region encoding $PfSPI1_{397}$ is referred to herein as $nfSPI1_{1191}$, the nucleic acid sequence of which is represented in SEQ ID NO:4 (the coding strand) and SEQ ID NO:5 (the complementary strand). The amino acid sequence of flea $PfSPI1_{397}$ (i.e., SEQ ID NO:2) predicts that $PfSPI1_{397}$ has an estimated molecular weight of about 44.4 kD and an estimated pI of about 4.97. Analysis of SEQ ID NO:2 suggests the presence of a signal peptide encoded by a stretch of amino acids spanning from about amino acid 1 through about amino acid 21. The proposed mature protein, denoted herein as $PfSPI1_{376}$, contains about 376 amino acids which is represented herein as SEQ ID NO:6. The amino acid sequence of flea $PfSPI1_{376}$ (i.e. SEQ ID NO:6) predicts that $PfSPI1_{376}$ has an estimated molecular weight of about 42.1 kD, an estimated pI of about 4.90, and a predicted asparagine-linked glycosylation site extending from about amino acid 252 to about amino acid 254.

Homology searches of the non-redundant protein and nucleotide sequence databases were performed through the National Center for Biotechnology Information using the BLAST network. The protein database includes SwissProt+ PIR+SPUpdate+Genpept+GPUpdate. The nucleotide database includes GenBank+EMBL+DDBJ+PDB. The protein search was performed using SEQ ID NO:2, which showed significant homology to certain serpin proteins. The highest scoring match of the homology search at the amino acid level was GenBank accession number 1378131: *Manduca sexta*, which was about 36% identical with SEQ ID NO:2. At the nucleotide level, the search was performed using SEQ ID NO:4, which was most similar to accession number L20792, a putative serine proteinase inhibitor gene (serpin 1, exon 9 copy 2) of *Manduca sexta*, being about 55% identical.

B. An about 1358-nucleotide consensus sequence of the entire flea $nfSPI2_{1358}$ DNA fragment was determined; the sequences of the two complementary strands are presented as SEQ ID NO:7 (the coding strand) and SEQ ID NO:9 (the complementary strand). The flea $nfSPI2_{1358}$ sequence contains a partial coding region, which is truncated at the 5' end. The first in-frame codon spans nucleotides from about 2 through about 4 and the stop codon spans nucleotides from about 1199 through about 1201 of SEQ ID NO:7.

Translation of SEQ ID NO:7 yields a protein of about 399 amino acids, denoted $PfSPI2_{399}$, the amino acid sequence of which is presented in SEQ ID NO:8. The nucleic acid molecule consisting of the coding region encoding $PfSPI2_{399}$ is referred to herein as $nfSPI2_{1197}$, the nucleic acid sequence of which is represented in SEQ ID NO:10 (the coding strand) and SEQ ID NO:11 (the complementary strand). Analysis of SEQ ID NO:8 suggests the presence of a partial signal peptide encoded by a stretch of amino acids spanning from about amino acid 1 through about amino acid 23. The proposed mature protein, denoted herein as $PfSPI2_{376}$, contains about 376 amino acids which is represented herein as SEQ ID NO:12. The amino acid sequence of flea $PfSPI1_{376}$ (i.e. SEQ ID NO:12) predicts that $PfSPI2_{376}$ has an estimated molecular weight of about 42.1 kD, an estimated pI of about 4.87, and a predicted asparagine-linked glycosylation site extending from about amino acid 252 to about amino acid 254.

BLAST searches were performed as described in Section A. The protein search was performed using SEQ ID NO:8, which showed significant homology to certain serpin proteins. The highest scoring match of the homology search at the amino acid level was GenBank accession number 1345616: *Homo sapiens*, which was about 36% identical with SEQ ID NO:8. At the nucleotide level, the search was performed using SEQ ID NO:10, which was most similar to accession number L20790, a putative serine proteinase inhibitor gene (serpin 1, exon 9 copy 1) of *Manduca sexta*, being about 43% identical.

C. An about 1838-nucleotide consensus sequence of the entire flea $nfSPI3_{1838}$ DNA fragment was determined; the sequences of the two complementary strands are presented as SEQ ID NO:13 (the coding strand) and SEQ ID NO:15 (the complementary strand). The flea $nfSPI3_{1838}$ sequence contains a full-length coding region. The apparent start and stop codons span nucleotides from about 306 through about 308 and from about 1566 through about 1568, respectively, of SEQ ID NO:13. A putative polyadenylation signal (5' AATAAA 3') is located in a region spanning from about nucleotide 1803 through about 1808 of SEQ ID NO:13.

Translation of SEQ ID NO:13 yields a protein of about 420 amino acids, denoted $PfSPI3_{420}$, the amino acid sequence of which is presented in SEQ ID NO:14. The nucleic acid molecule consisting of the coding region encoding $PfSPI3_{420}$ is referred to herein as $nfSPI3_{1260}$, the nucleic acid sequence of which is represented in SEQ ID NO:16 (the coding strand) and SEQ ID NO:17 (the complementary strand). The amino acid sequence of flea $PfSPI3_{420}$ (i.e., SEQ ID NO:14) predicts that $PfSPI3_{420}$ has an estimated molecular weight of about 47.1 kD and an estimated pI of about 4.72. Analysis of SEQ ID NO:14 suggests the presence of a signal peptide encoded by a stretch of amino acids spanning from about amino acid 1 through about amino acid 30. The proposed mature protein, denoted herein as PfSPI3$_{390}$, contains about 390 amino acids which is represented herein as SEQ ID NO:18. The amino acid sequence of flea PfSPI3$_{390}$ (i.e. SEQ ID NO:18) predicts that PfSPI3$_{390}$ has an estimated molecular weight of about 43.7 kD, an estimated pI of about 4.63, and two predicted asparagine-linked glycosylation sites extending from about amino acid 252 to about amino acid 254 and from about amino acid 369 to about amino acid 371.

BLAST searches were performed as described in Section A. The protein search was performed using SEQ ID NO:14, which showed significant homology to certain serpin proteins. The highest scoring match of the homology search at the amino acid level was GenBank accession number 1345616: *Homo sapiens,* which was about 35% identical with SEQ ID NO:14. At the nucleotide level, the search was performed using SEQ ID NO:16, which was most similar to accession number L20792, a putative serine proteinase inhibitor gene (serpin 1, exon 9 copy 2) of *Manduca sexta,* being about 52% identical.

D. An about 1414-nucleotide consensus sequence of the entire flea nfSPI4$_{1414}$ DNA fragment was determined; the sequences of the two complementary strands are presented as SEQ ID NO:19 (the coding strand) and SEQ ID NO:21 (the complementary strand). The flea nfSPI4$_{1414}$ sequence contains a partial coding region, truncated at the 5' end. The first in-frame codon spans nucleotides from about 2 through about 4 and the stop codon spans nucleotides from about 1181 through about 1183 of SEQ ID NO:19. A putative polyadenylation signal (5' AATAAA 3') is located in a region spanning from about nucleotide 1179 through about 1184 of SEQ ID NO:19.

Translation of SEQ ID NO:19 yields a protein of about 393 amino acids, denoted PfSPI4$_{393}$, the amino acid sequence of which is presented in SEQ ID NO:20. The nucleic acid molecule consisting of the coding region encoding PfSPI4$_{393}$ is referred to herein as nfSPI4$_{1179}$, the nucleic acid sequence of which is represented in SEQ ID NO:22 (the coding strand) and SEQ ID NO:23 (the complementary strand). Analysis of SEQ ID NO:20 suggests the presence of a partial signal peptide encoded by a stretch of amino acids spanning from about amino acid 1 through about amino acid 17. The proposed mature protein, denoted herein as PfSPI4$_{376}$, contains about 376 amino acids which is represented herein as SEQ ID NO:24. The amino acid sequence of flea PfSPI4$_{376}$ (i.e. SEQ ID NO:24) predicts that PfSPI4$_{376}$ has an estimated molecular weight of about 42.2 kD, an estimated pI of about 5.31, and a predicted asparagine-linked glycosylation site extending from about amino acid 252 to about amino acid 254.

BLAST searches were performed as described in Section A. The protein search was performed using SEQ ID NO:20, which showed significant homology to certain serpin proteins. The highest scoring match of the homology search at the amino acid level was GenBank accession number 1345616: *Homo sapiens,* which was about 38% identical with SEQ ID NO:20. At the nucleotide level, the search was performed using SEQ ID NO:22, which was most similar to accession number L20793, a putative serine proteinase inhibitor gene (serpin 1, exon 9 unknown copy number) of *Manduca sexta,* being about 55% identical.

E. An about 1492-nucleotide consensus sequence of the entire flea nfSPI5$_{1492}$ DNA fragment was determined; the sequences of the two complementary strands are presented as SEQ ID NO:25 (the coding strand) and SEQ ID NO:27 (the complementary strand). The flea nfSPI5$_{1492}$ sequence contains a partial coding region, truncated at the 5' end. The first in-frame codon spans nucleotides from about 3 through about 5 and the stop codon spans nucleotides from about 1197 through about 1199 of SEQ ID NO:25. A putative polyadenylation signal (5' AATAAA 3') is located in a region spanning from about nucleotide 1416 through about 1421 of SEQ ID NO:25.

Translation of SEQ ID NO:25 yields a protein of about 398 amino acids, denoted PfSPI5$_{398}$, the amino acid sequence of which is presented in SEQ ID NO:26. The nucleic acid molecule consisting of the coding region encoding PfSPI5$_{398}$ is referred to herein as nfSPI5$_{1194}$, the nucleic acid sequence of which is represented in SEQ ID NO:28 (the coding strand) and SEQ ID NO:29 (the complementary strand). Analysis of SEQ ID NO:26 suggests the presence of a partial signal peptide encoded by a stretch of amino acids spanning from about amino acid 1 through about amino acid 22. The proposed mature protein, denoted herein as PfSPI5$_{376}$, contains about 376 amino acids which is represented herein as SEQ ID NO:30. The amino acid sequence of flea PfSPI5$_{376}$ (i.e. SEQ ID NO:30) predicts that PfSPI5$_{376}$ has an estimated molecular weight of about 42.3 kD, an estimated pI of about 5.31 and a predicted asparagine-linked glycosylation site extending from about amino acid 252 to about amino acid 254.

BLAST searches were performed as described in Section A. The protein search was performed using SEQ ID NO:26, which showed significant homology to certain serpin proteins. The highest scoring match of the homology search at the amino acid level was GenBank accession number 1345616: *Homo sapiens,* which was about 38% identical with SEQ ID NO:26. At the nucleotide level, the search was performed using SEQ ID NO:28, which was most similar to accession number L20790, a putative serine proteinase inhibitor gene (serpin 1, exon 9 copy 1) of *Manduca sexta,* being about 45% identical.

F. An about 1454-nucleotide consensus sequence of the entire flea nfSPI6$_{1454}$ DNA fragment was determined; the sequences of the two complementary strands are presented as SEQ ID NO:31 (the coding strand) and SEQ ID NO:33 (the complementary strand). The flea nfSPI6$_{1454}$ sequence contains a full length coding region. The apparent start and stop codons span nucleotides from about 20 through about 22 and from about 1211 through about 1213, respectively, of SEQ ID NO:31. A putative polyadenylation signal (5' AATAAA 3') is located in a region spanning from about nucleotide 1419 through about 1424 of SEQ ID NO:31.

Translation of SEQ ID NO:31 yields a protein of about 397 amino acids, denoted PfSPI6$_{397}$, the amino acid sequence of which is presented in SEQ ID NO:32. The nucleic acid molecule consisting of the coding region encoding PfSPI6$_{397}$ is referred to herein as nfSPI6$_{1191}$, the nucleic acid sequence of which is represented in SEQ ID NO:34 (the coding strand) and SEQ ID NO:35 (the complementary strand). The amino acid sequence of flea PfSPI6$_{397}$ (i.e., SEQ ID NO:32) predicts that PfSPI6$_{397}$ has an estimated molecular weight of about 44.4 kD and an estimated pI of about 4.90. Analysis of SEQ ID NO:32 suggests the presence of a signal peptide encoded by a stretch of amino acids spanning from about amino acid 1 through about amino acid 21. The proposed mature protein, denoted herein as PfSPI6$_{376}$, contains about 376 amino acids which is represented herein as SEQ ID NO:36. The amino acid sequence of flea PfSPI6$_{376}$ (i.e. SEQ ID NO:36) predicts that PfSPI6$_{376}$ has an estimated molecular weight of about 42.1 kD, an estimated pI of about 4.84, and a predicted asparagine-linked glycosylation site extending from about amino acid 252 to about amino acid 254.

BLAST searches were performed as described in Section A. The protein search was performed using SEQ ID NO:32, which showed significant homology to certain serpin proteins. The highest scoring match of the homology search at the amino acid level was GenBank accession number 1378131: *Manduca sexta,* which was about 36% identical with SEQ ID NO:32. At the nucleotide level, the search was performed using SEQ ID NO:34, which was most similar to accession number L20792, a putative serine proteinase inhibitor gene (serpin 1, exon 9 copy 2) of *Manduca sexta,* being about 55% identical.

Example 5

This example discloses the production of a several recombinant cells of the present invention.

A. Recombinant molecule pλP$_R$-nfSPI2$_{1139}$, containing a portion of a flea serine protease inhibitor molecule operatively linked to bacteriophage lambda transcription control sequences and to a fusion sequence encoding a polyhistidine segment comprising 6 histidines was produced as follows. An about 1185-nucleotide DNA fragment containing nucleotides spanning from about 26 through about 1202 of SEQ ID NO:7, denoted herein as nfSPI2$_{1185}$, was PCR amplified from nucleic acid molecule 12$_{1358}$, produced as described in Example 3, using sense primer JPI5, having the nucleic acid sequence 5' GTGTTTCTTTTTGTATCAGTG 3', denoted as SEQ ID NO:37, and antisense primer, JPI18, having the nucleic acid sequence 5' CGGAATTCTTTAAAGGGATTTAACAC 3' (EcoRI site in bold), denoted SEQ ID NO:38. The amplified gene sequence contained a natural BamHI site about 24 bp downstream of the 3' end of JPI5 that was used for subcloning into the expression vector. Recombinant molecule pλP$_R$-nfSPI2$_{1139}$ was produced by digesting nfSPI2$_{1185}$-containing PCR product with BamHI and EcoRI restriction endonucleases, column purifying the resulting fragment, and directionally subcloning the fragment into expression vector P$_R$/T$^2$ori/S10HIS-RSET-A9, the production of which is described in PCT Publication No. U.S. Ser. No. 95/02941, by Tripp et al., published Sep. 14, 1995, Example 7, which had been similarly cleaved with BamHI and EcoRI and gel purified.

Recombinant molecule pλP$_R$-nfSPI2$_{1139}$ was transformed into *E. coli* strain HB101 competent cells (available from Gibco/BRL, Gaithersburg, Md.) to form recombinant cell *E.coli*:pλP$_R$-nfSPI2$_{1139}$ using standard techniques as disclosed in Sambrook, et al., ibid.

B. Recombinant molecule pλP$_R$-nfSPI3$_{1179}$, containing a portion of a flea serine protease inhibitor molecule operatively linked to bacteriophage lambda transcription control sequences and to a fusion sequence encoding a polyhistidine segment comprising 6 histidines was produced as follows. An about 1225-nucleotide DNA fragment containing nucleotides spanning from about 351 through about 1570 of SEQ ID NO:13, denoted herein as nfSPI3$_{1225}$, was PCR amplified from nucleic acid molecule nfSPI3$_{1838}$, produced as described in Example 3, using sense primer JPI5, having the nucleic acid sequence 5' GTGTTTCTTTTTGTATCAGTG 3', denoted as SEQ ID NO:37, and antisense primer was JPI15, having the nucleic acid sequence 5' CGGAATTCTAATTGGTAAATCTC 3' (EcoRI site in bold), denoted SEQ ID NO:39. The amplified gene sequence contained a natural BamHI site about 24 bp downstream of the 3' end of JPI5 that was used for subcloning into the expression vector. Recombinant molecule pλP$_R$-nfSPI3$_{1179}$ was produced by digesting nfSPI3$_{1225}$-containing PCR product with BamHI and EcoRI restriction endonucleases, column purifying the resulting fragment, and directionally subcloning the fragment into expression vector P$_R$/T$^2$ori/S10HIS-RSET-A9, as described in Section A above, which had been similarly cleaved with BamHI and EcoRI and gel purified.

Recombinant molecule pλP$_R$-nfSPI3$_{1179}$ was transformed into *E. coli* strain HB101 competent cells (available from Gibco/BRL) to form recombinant cell *E.coli*:pλP$_R$-nfSPI3$_{1179}$ using standard techniques as disclosed in Sambrook, et al., ibid.

C. Recombinant molecule pλP$_R$-nfSPI4$_{1140}$, containing a portion of a flea serine protease inhibitor molecule operatively linked to bacteriophage lambda transcription control sequences and to a fusion sequence encoding a polyhistidine segment comprising 6 histidines was produced as follows. An about 1186-nucleotide DNA fragment containing nucleotides spanning from about 8 through about 1186 of SEQ ID NO:19, denoted herein as nfSPI4$_{1186}$, was PCR amplified from nucleic acid molecule nfSPI4$_{1414}$, produced as described in Example 3, using sense primer JPI5, having the nucleic acid sequence 5' GTGTTTCTTTTTGTATCAGTG 3', denoted as SEQ ID NO:37, and antisense primer was JPI17, having the nucleic acid sequence 5' CGGAATTCTTTTATTCAGTTGTTGG 3' (EcoRI site in bold), denoted SEQ ID NO:40. The amplified gene sequence contained a natural BamHI site about 24 bp downstream of the 3' end of JPI5 that was used for subcloning into the expression vector. Recombinant molecule pλP$_R$-nfSPI4$_{1140}$ was produced by digesting nfSPI4$_{1186}$-containing PCR product with BamHI and EcoRI restriction endonucleases, column purifying the resulting fragment, and directionally subcloning the fragment into expression vector P$_R$/T$^2$ori/S10HIS-RSET-A9, as described in Section A above, which had been similarly cleaved with BamHI and EcoRI and gel purified.

Recombinant molecule pλP$_R$-nfSPI4$_{1140}$ was transformed into *E. coli* strain HB101 competent cells (available from Gibco/BRL) to form recombinant cell *E.coli*:pλP$_R$-nfSPI4$_{1140}$ using standard techniques as disclosed in Sambrook, et al., ibid.

D. Recombinant molecule pλP$_R$-nfSPI5$_{1140}$, containing a portion of a flea serine protease inhibitor molecule operatively linked to bacteriophage lambda transcription control sequences and to a fusion sequence encoding a polyhistidine segment comprising 6 histidines was produced as follows. An about 1186-nucleotide DNA fragment containing nucleotides spanning from about 24 through about 1202 of SEQ ID NO:25, denoted herein as nfSPI5$_{1186}$, was PCR amplified from nucleic acid molecule nfSPI5$_{1492}$, produced as described in Example 3, using sense primer JPI5, having the nucleic acid sequence 5' GTGTTTCTTTTTGTATCAGTG 3', denoted as SEQ ID NO:37, and antisense primer was JPI17, having the nucleic acid sequence 5' CGGAATTCTTTTATTCAGTTGTTGG 3' (EcoRI site in bold), denoted SEQ ID NO:40. The amplified gene sequence contained a natural BamHI site about 24 bp downstream of the 3' end of JPI5 that was used for subcloning into the expression vector. Recombinant molecule pλP$_R$-nfSPI5$_{1140}$ was produced by digesting nfSPI5$_{1186}$-containing PCR product with BamHli and EcoRI restriction endonucleases, column purifying the resulting fragment, and directionally subcloning the fragment into expression vector P$_R$/T$^2$ori/S10HIS-RSET-A9, as described in Section A above, which had been similarly cleaved with BamHI and EcoRI and gel purified.

Recombinant molecule pλP$_R$-nfSPI5$_{1140}$ was transformed into E. coli strain HB101 competent cells (available from Gibco/BRL) to form recombinant cell E.coli:pλP$_R$-nfSPI5$_{1140}$ using standard techniques as disclosed in Sambrook, et al., ibid.

E. Recombinant molecule pλP$_R$-nfSPI6$_{1136}$, containing a portion of a flea serine protease inhibitor molecule operatively linked to bacteriophage lambda transcription control sequences and to a fusion sequence encoding a polyhistidine segment comprising 6 histidines was produced as follows. An about 1182-nucleotide DNA fragment containing nucleotides spanning from about 38 through about 1214 of SEQ ID NO:31, denoted herein as nfSPI6$_{1182}$, was PCR amplified from nucleic acid molecule nfSPI6$_{1454}$, produced as described in Example 3, using sense primer JPI5, having the nucleic acid sequence 5' GTGTTTCTTTTTGTAT-CAGTG 3', denoted as SEQ ID NO:37, and antisense primer was JPI16, having the nucleic acid sequence 5' CGGAAT-TCATAGAGTTTGAACTC 3' (EcoRI site in bold), denoted SEQ ID NO:41. The amplified gene sequence contained a natural BamHI site about 24 bp downstream of the 3' end of JPI5 that was used for subcloning into the expression vector. Recombinant molecule pλP$_R$-nfSPI6$_{1136}$ was produced by digesting nfSPI6$_{1182}$-containing PCR product with BamHI and EcoRI restriction endonucleases, column purifying the resulting fragment, and directionally subcloning the fragment into expression vector P$_R$/T$^2$ori/S10HIS-RSET-A9, as described in Section A above, which had been similarly cleaved with BamHI and EcoRI and gel purified.

Recombinant molecule pλP$_R$-nfSPI6$_{1136}$ was transformed into E. coli strain HB101 competent cells (available from BRL) to form recombinant cell E.coli:pλP$_R$-nfSPI6$_{1136}$ using standard techniques as disclosed in Sambrook, et al., ibid.

Example 6

This Example describes the production in bacteria of several flea serine protease inhibitor proteins of the present invention.

Recombinant cells E.Coli:pλP$_R$-nfSPI2$_{1139}$, E.coli:pλP$_R$-nfSPI3$_{1179}$, E.coli:pλP$_R$-nfSPI4$_{1140}$, and E.Coli:pλP$_R$-nfSPI6$_{1136}$, produced as described in Example 5, were cultured in shake flasks containing an enriched bacterial growth medium containing 0.1 mg/ml ampicillin and 0.1% glucose at about 32° C. When the cells reached an OD$_{600}$ of about 0.4 to about 0.5, expression of flea pλP$_R$-nfSPI2$_{1139}$, pλP$_R$-nfSPI3$_{1179}$, pλP$_R$-nfSPI4$_{1140}$, and pλP$_R$-nfSPI6$_{1136}$, was induced by elevating the temperature to 42° C., and culturing the cells for about 3 hours. Protein production was monitored by SDS-PAGE of recombinant cell lysates, followed by Coomassie Blue staining and immunoblot analyses using a T7 Tag monoclonal antibody (available from Novagen, Inc.). Recombinant cells E.Coli:pλP$_R$-nfSPI2$_{1139}$, E.Coli:pλP$_R$-nfSPI3$_{1179}$, E.Coli:pλP$_R$-nfSPI4$_{1140}$, and E.Coli:pλP$_R$-nfSPI6$_{1136}$ produced fusion proteins, denoted herein as PHis-PfSPI2$_{376}$, PHis-PfSPI3$_{390}$, PHis-PfSPI4$_{376}$, and PHis-PfSPI6$_{376}$, that migrated with an apparent molecular weights of about 45 to 50 kD as predicted.

Example 7

This example describes analysis of the variable and constant domains of the nucleic acid molecules of the present invention.

The sequences of each of the flea serine protease inhibitor cDNA molecules nfSPI1$_{1584}$, nfSPI2$_{1358}$, nfSPI3$_{1838}$, nfSPI4$_{1414}$, nfSPI5$_{1492}$, and nfSPI6$_{1454}$, presented in Example 4, were subdivided into three domains based on comparisons between the six sequences. The observed versions of the three domains are summarized in Table 1. Domain I, spanning from about nucleotide 1 to about nucleotide 142 in nfSPI1$_{1584}$, from about nucleotide 1 to about nucleotide 14 in nfSPI2$_{1358}$, from about nucleotide 1 to about nucleotide 339 in nfSPI3$_{1838}$, not present in nfSPI4$_{1441}$, from about nucleotide 1 to about nucleotide 12 in nfSPI5$_{1492}$, and from about nucleotide 1 to about nucleotide 26 in nfSPI6$_{1454}$, contains upstream untranslated sequences and the coding regions for the amino termini of the serine protease inhibitor proteins. Domain II, spanning from about nucleotide 143 to about nucleotide 1195 in nfSPI1$_{1584}$, from about nucleotide 15 to about nucleotide 1067 in nfSPI2$_{1358}$, from about nucleotide 340 to about nucleotide 1392 in nfSPI3$_{1838}$, from about nucleotide 1 to about nucleotide 1049 in nfSPI4$_{1414}$, from about nucleotide 13 to about nucleotide 1065 in nfSPI5$_{1492}$, and from about nucleotide 27 to about nucleotide 1079 in nfSPI6$_{1454}$, consists of the central core of the coding sequence and encodes 350 amino acids that are extremely highly conserved (i.e. less than approximately 2% variation) between the six serine protease inhibitor clones. The predicted mature N-terminus of the serine protease inhibitors is within Domain II; thus, the variability of Domain I should have no effect on the sequence of mature serine protease inhibitor polypeptides. Domain III sequences are highly variable, yet still related to one another; Domain III, spanning from about nucleotide 1196 to about nucleotide 1584 in nfSPI1$_{1584}$, from about nucleotide 1068 to about nucleotide 1358 in nfSPI2$_{1358}$, from about nucleotide 1393 to about nucleotide 1838 in nfSPI3$_{1838}$, from about nucleotide 1050 to about nucleotide 1414 in nfSPI4$_{1414}$, from about nucleotide 1066 to about nucleotide 1492 in nfSPI5$_{1492}$, and from about nucleotide 1080 to about nucleotide 1454 in nfSPI6$_{1454}$, encodes the C-termini of the serine protease inhibitor proteins.

While not being bound by theory, the most probable explanation for the mixing of the domain versions within the six clones sequenced is a mechanism of alternative mRNA splicing. Such a pattern was described previously by Jiang et al., 1994, J. Biol. Chem. 269, 55–58 for serpins in Manduca sexta. For this family of serpins, eight exons encode a 336-amino acid constant region, followed by a 40–45-amino acid variable region that is encoded by the ninth exon. At least twelve alternative forms of the ninth exon are tandemly arranged in the genome between exons 8 and 10. Thus, mutually exclusive exon use can account for the variability the authors observed in cDNA clones.

Based on analogy to the Manduca system, flea serine protease inhibitors probably exhibit a similar gene structure in that the C-terminal variable region (Domain III) is encoded by multiple exons that are used in a mutually exclusive splicing mechanism. The flea serine protease inhibitor molecules appear to differ from Manduca in that for the flea molecules there are at least two alternative exons at the 5' end of the gene (Domain I) as well, and there does not appear to be final constant exon (exon 10 in Manduca) at the 3' end. It is probable that other versions of Domain III are present in the flea genome that were not observed in the six cDNA sequences presented herein.

Table 1. Summary of sequence variations of the three domains of flea serine protease inhibitor cDNA clones. Letters represent widely divergent sequences (e.g., A vs. B); numbers denote minor variations (i.e., less than 2%) between lettered sequences (e.g., K1 vs. K2).

| Clone | Domain I | Domain II | Domain III |
|---|---|---|---|
| nfSe1$_{1584}$ | A | K1 | W1 |
| nfSe2$_{1358}$ | B | K2 | X |
| nfSe3$_{1838}$ | B | K2 | Y |
| nfSe4$_{1414}$ | missing | K2 | Z |
| nfSe5$_{1492}$ | B | K3 | Z |
| nfSe6$_{1454}$ | A | K2 | W2 |

Sequence Listing

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:41 submitted herewith are the same.

```
                              SEQUENCE LISTING (1) GENERAL INFORMATION:

(iii) NUMBER OF SEQUENCES:   41

(2) INFORMATION FOR SEQ ID NO:1:

(i) SEQUENCE CHARACTERISTICS:
         (A) LENGTH:  1584 nucleotides
         (B) TYPE:  nucleic acid
         (C) STRANDEDNESS:  single
         (D) TOPOLOGY:  linear (ii) MOLECULE TYPE:  cDNA (ix) FEATURE:
         (A) NAME/KEY:  CDS
         (B) LOCATION:  136..1326

(xi) SEQUENCE DESCRIPTION:  SEQ ID NO:1:

GCCTGGAAGG TGATAAGTAA ACGGGCACGG TAGTGTTTTG TTTTAGAAAA TAATTTTAAT        60

TCGTACGACG TACGTTTTTG TGATTTTAAT TTTTTAGTGT TTTTGTAGCT CTGAAAGAGC       120

CGAAATTTTA GCAAA ATG ATT AAC GCA CGA CTT GTG TTT CTT TTT GTA TCA       171
                Met Ile Asn Ala Arg Leu Val Phe Leu Phe Val Ser
                 1               5                  10

GTG TTA TTA CCA ATT TCA ACA ATG GCC GAT CCC CAG GAA TTG TCT ACA        219
Val Leu Leu Pro Ile Ser Thr Met Ala Asp Pro Gln Glu Leu Ser Thr
         15                  20                  25

AGT ATT AAC CAG TTT GCT GGA AGC CTG TAC AAT ACA GTT GCT TCT GGC        267
Ser Ile Asn Gln Phe Ala Gly Ser Leu Tyr Asn Thr Val Ala Ser Gly
     30                  35                  40

AAC AAA GAC AAT CTC ATC ATG TCC CCA TTG TCT GTA CAA ACT GTT CTA        315
Asn Lys Asp Asn Leu Ile Met Ser Pro Leu Ser Val Gln Thr Val Leu
 45                  50                  55                  60

TCC CTG GTG TCA ATG GGA GCT GGT GGC AAT ACT GCC ACA CAA ATA GCT        363
Ser Leu Val Ser Met Gly Ala Gly Gly Asn Thr Ala Thr Gln Ile Ala
         65                  70                  75

GCT GGT TTG CGT CAG CCT CAA TCA AAA GAA AAA ATT CAA GAT GAC TAC        411
Ala Gly Leu Arg Gln Pro Gln Ser Lys Glu Lys Ile Gln Asp Asp Tyr
     80                  85                  90

CAC GCA TTG ATG AAC ACT CTT AAT ACA CAA AAA GGT GTA ACT CTG GAA        459
His Ala Leu Met Asn Thr Leu Asn Thr Gln Lys Gly Val Thr Leu Glu
         95                 100                 105

ATT GCC AAT AAA GTT TAT GTT ATG GAA GGC TAT ACA TTA AAA CCC ACC        507
Ile Ala Asn Lys Val Tyr Val Met Glu Gly Tyr Thr Leu Lys Pro Thr
    110                 115                 120
```

-continued

```
TTC AAA GAA GTT GCC ACC AAC AAA TTC TTA GCT GGA GCA GAA AAC TTG    555
Phe Lys Glu Val Ala Thr Asn Lys Phe Leu Ala Gly Ala Glu Asn Leu
125                 130                 135                 140

AAC TTT GCC CAA AAT GCT GAA AGC GCT AAA GTT ATC AAC ACT TGG GTT    603
Asn Phe Ala Gln Asn Ala Glu Ser Ala Lys Val Ile Asn Thr Trp Val
        145                 150                 155

GAA GAA AAA ACT CAT GAC AAA ATT CAT GAT TTG ATC AAA GCC GGT GAT    651
Glu Glu Lys Thr His Asp Lys Ile His Asp Leu Ile Lys Ala Gly Asp
                160                 165                 170

CTA GAC CAG GAT TCA AGA ATG GTT CTT GTC AAT GCA TTG TAC TTC AAG    699
Leu Asp Gln Asp Ser Arg Met Val Leu Val Asn Ala Leu Tyr Phe Lys
                    175                 180                 185

GGT CTT TGG GAG AAA CAA TTC AAA AAG GAA AAT ACC CAA GAC AAA CCT    747
Gly Leu Trp Glu Lys Gln Phe Lys Lys Glu Asn Thr Gln Asp Lys Pro
                        190                 195                 200

TTC TAT GTT ACT GAA ACA GAG ACA AAG AAT GTA CGA ATG ATG CAC ATT    795
Phe Tyr Val Thr Glu Thr Glu Thr Lys Asn Val Arg Met Met His Ile
205                 210                 215                 220

AAG GAT AAA TTC CGT TAT GGA GAA TTT GAA GAA TTA GAT GCC AAG GCT    843
Lys Asp Lys Phe Arg Tyr Gly Glu Phe Glu Glu Leu Asp Ala Lys Ala
            225                 230                 235

GTA GAA TTG CCC TAC AGG AAC TCA GAT TTG GCC ATG TTA ATC ATT TTG    891
Val Glu Leu Pro Tyr Arg Asn Ser Asp Leu Ala Met Leu Ile Ile Leu
                240                 245                 250

CCA AAC AGC AAA ACT GGT CTC CCC GCT CTT GAA GAA AAA TTA CAA AAT    939
Pro Asn Ser Lys Thr Gly Leu Pro Ala Leu Glu Glu Lys Leu Gln Asn
                    255                 260                 265

GTT GAT TTG CAA AAC TTG ACT CAA CGC ATG TAC TCT GTT GAA GTT ATT    987
Val Asp Leu Gln Asn Leu Thr Gln Arg Met Tyr Ser Val Glu Val Ile
                        270                 275                 280

TTG GAT CTG CCT AAA TTC AAG ATT GAA TCT GAA ATT AAT TTG AAT GAT   1035
Leu Asp Leu Pro Lys Phe Lys Ile Glu Ser Glu Ile Asn Leu Asn Asp
285                 290                 295                 300

CCT CTG AAA AAG TTG GGT ATG TCT GAT ATG TTT GTT CCT GGA AAA GCT   1083
Pro Leu Lys Lys Leu Gly Met Ser Asp Met Phe Val Pro Gly Lys Ala
            305                 310                 315

GAT TTC AAA GGA TTG CTT GAA GGA TCT GAT GAG ATG TTA TAT ATT TCT   1131
Asp Phe Lys Gly Leu Leu Glu Gly Ser Asp Glu Met Leu Tyr Ile Ser
                320                 325                 330

AAA GTA ATT CAA AAA GCT TTC ATT GAA GTA AAT GAA GAA GGT GCT GAA   1179
Lys Val Ile Gln Lys Ala Phe Ile Glu Val Asn Glu Glu Gly Ala Glu
                    335                 340                 345

GCT GCA GCT GCC ACA GCT ACC TTT ATG GTT ACC TAT GAA CTG GAG GTT   1227
Ala Ala Ala Ala Thr Ala Thr Phe Met Val Thr Tyr Glu Leu Glu Val
                        350                 355                 360

TCC CTG GAT CTT CCC ACT GTT TTT AAA GTC GAT CAT CCA TTC AAT ATT   1275
Ser Leu Asp Leu Pro Thr Val Phe Lys Val Asp His Pro Phe Asn Ile
365                 370                 375                 380

GTT TTG AAG ACA GGT GAT ACT GTT ATT TTT AAT GGG CGA GTT CAA ACT   1323
Val Leu Lys Thr Gly Asp Thr Val Ile Phe Asn Gly Arg Val Gln Thr
            385                 390                 395

TTA TAA AATGGATAGT GTAAAAAGAA TACAAGATCT ATCTGAATCT CTGGATTAAT   1379
Leu

GAAGTAATTT TTCTACAATA TTTTTTAATA GTTATTAGGG CTAAAATAAG TTCATTTTTT   1439

AGTATGTGGT ATAAATCGTG TAGACGAAAA ATGTTTTGTT TTAGTTTTCA CTTTTTATGA   1499

ATGTAATCAC CTATATAATG TTGTAGTTTA TGTAATAAAA ATGTTAAATG TGAAAAAAAA   1559

AAAAAAAAAA AAAAAAAAAA AAAA                                        1584
```

(2) INFORMATION FOR SEQ ID NO:2:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ile Asn Ala Arg Leu Val Phe Leu Phe Val Ser Val Leu Leu Pro
 1               5                  10                  15

Ile Ser Thr Met Ala Asp Pro Gln Glu Leu Ser Thr Ser Ile Asn Gln
                20                  25                  30

Phe Ala Gly Ser Leu Tyr Asn Thr Val Ala Ser Gly Asn Lys Asp Asn
            35                  40                  45

Leu Ile Met Ser Pro Leu Ser Val Gln Thr Val Leu Ser Leu Val Ser
        50                  55                  60

Met Gly Ala Gly Gly Asn Thr Ala Thr Gln Ile Ala Ala Gly Leu Arg
65                  70                  75                  80

Gln Pro Gln Ser Lys Glu Lys Ile Gln Asp Asp Tyr His Ala Leu Met
                85                  90                  95

Asn Thr Leu Asn Thr Gln Lys Gly Val Thr Leu Glu Ile Ala Asn Lys
            100                 105                 110

Val Tyr Val Met Glu Gly Tyr Thr Leu Lys Pro Thr Phe Lys Glu Val
        115                 120                 125

Ala Thr Asn Lys Phe Leu Ala Gly Ala Glu Asn Leu Asn Phe Ala Gln
        130                 135                 140

Asn Ala Glu Ser Ala Lys Val Ile Asn Thr Trp Val Glu Glu Lys Thr
145                 150                 155                 160

His Asp Lys Ile His Asp Leu Ile Lys Ala Gly Asp Leu Asp Gln Asp
                165                 170                 175

Ser Arg Met Val Leu Val Asn Ala Leu Tyr Phe Lys Gly Leu Trp Glu
            180                 185                 190

Lys Gln Phe Lys Lys Glu Asn Thr Gln Asp Lys Pro Phe Tyr Val Thr
        195                 200                 205

Glu Thr Glu Thr Lys Asn Val Arg Met Met His Ile Lys Asp Lys Phe
        210                 215                 220

Arg Tyr Gly Glu Phe Glu Leu Asp Ala Lys Ala Val Glu Leu Pro
225                 230                 235                 240

Tyr Arg Asn Ser Asp Leu Ala Met Leu Ile Ile Leu Pro Asn Ser Lys
                245                 250                 255

Thr Gly Leu Pro Ala Leu Glu Glu Lys Leu Gln Asn Val Asp Leu Gln
            260                 265                 270

Asn Leu Thr Gln Arg Met Tyr Ser Val Glu Val Ile Leu Asp Leu Pro
        275                 280                 285

Lys Phe Lys Ile Glu Ser Glu Ile Asn Leu Asn Asp Pro Leu Lys Lys
        290                 295                 300

Leu Gly Met Ser Asp Met Phe Val Pro Gly Lys Ala Asp Phe Lys Gly
305                 310                 315                 320

Leu Leu Glu Gly Ser Asp Glu Met Leu Tyr Ile Ser Lys Val Ile Gln
                325                 330                 335

Lys Ala Phe Ile Glu Val Asn Glu Glu Gly Ala Glu Ala Ala Ala
            340                 345                 350

Thr Ala Thr Phe Met Val Thr Tyr Glu Leu Glu Val Ser Leu Asp Leu
```

```
                355                 360                 365
Pro Thr Val Phe Lys Val Asp His Pro Phe Asn Ile Val Leu Lys Thr
    370                 375                 380

Gly Asp Thr Val Ile Phe Asn Gly Arg Val Gln Thr Leu
385                 390                 395
```

(2) INFORMATION FOR SEQ ID NO:3:

(i) SEQUENCE CHARACTERISTICS:
        (A) LENGTH: 1584 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TTTTTTTTTT TTTTTTTTTT TTTTTTTTTT TTTCACATTT AACATTTTTA TTACATAAAC    60
TACAACATTA TATAGGTGAT TACATTCATA AAAAGTGAAA ACTAAAACAA AACATTTTTC   120
GTCTACACGA TTTATACCAC ATACTAAAAA ATGAACTTAT TTTAGACCTA ATAACTATTA   180
AAAAATATTG TAGAAAAATT ACTTCATTAA TCCAGAGATT CAGATAGATC TTGTATTCTT   240
TTTACACTAT CCATTTTATA AAGTTTGAAC TCGCCCATTA AAAATAACAG TATCACCTGT   300
CTTCAAAACA ATATTGAATG GATGATCGAC TTTAAAAACA GTGGGAAGAT CCAGGGAAAC   360
CTCCAGTTCA TAGGTAACCA TAAAGGTAGC TGTGGCAGCT GCAGCTTCAG CACCTTCTTC   420
ATTTACTTCA ATGAAAGCTT TTGAATTAC TTTAGAAATA TATAACATCT CATCAGATCC    480
TTCAAGCAAT CCTTTGAAAT CAGCTTTTCC AGGAACAAAC ATATCAGACA TACCCAACTT   540
TTTCAGAGGA TCATTCAAAT TAATTTCAGA TTCAATCTTG AATTTAGGCA GATCCAAAAT   600
AACTTCAACA GAGTACATGC GTTGAGTCAA GTTTTGCAAA TCAACATTTT GTAATTTTTC   660
TTCAAGAGCG GGGAGACCAG TTTTGCTGTT TGGCAAAATG ATTAACATGG CCAAATCTGA   720
GTTCCTGTAG GCAATTCTA CAGCCTTGGC ATCTAATTCT TCAAATTCTC CATAACGGAA    780
TTTATCCTTA ATGTGCATCA TTCGTACATT CTTTGTCTCT GTTTCAGTAA CATAGAAAGG   840
TTTGTCTTGG GTATTTTCCT TTTTGAATTG TTTCTCCCAA AGACCCTTGA AGTACAATGC   900
ATTGACAAGA ACCATTCTTG AATCCTGGTC TAGATCACCG GCTTTGATCA AATCATGAAT   960
TTTGTCATGA GTTTTTTCTT CAACCCAAGT GTTGATAACT TTAGCGCTTT CAGCATTTTG  1020
GGCAAAGTTC AAGTTTTCTG CTCCAGCTAA GAATTTGTTG GTGGCAACTT CTTTGAAGGT  1080
GGGTTTTAAT GTATAGCCTT CCATAACATA AACTTTATTG GCAATTTCCA GAGTTACACC  1140
TTTTTGTGTA TTAAGAGTGT TCATCAATGC GTGGTAGTCA TCTTGAATTT TTTCTTTTGA  1200
TTGAGGCTGA CGCAAACCAG CAGCTATTTG TGTGGCAGTA TTGCCACCAG CTCCCATTGA  1260
CACCAGGGAT AGAACAGTTT GTACAGACAA TGGGACATG ATGAGATTGT CTTTGTTGCC   1320
AGAAGCAACT GTATTGTACA GGCTTCCAGC AAACTGGTTA ATACTTGTAG ACAATTCCTG  1380
GGGATCGGCC ATTGTTGAAA TTGGTAATAA CACTGATACA AAAAGAAACA CAAGTCGTGC  1440
GTTAATCATT TTGCTAAAAT TTCGGCTCTT TCAGAGCTAC AAAAACACTA AAAATTAAA   1500
ATCACAAAAA CGTACGTCGT ACGAATTAAA ATTATTTTCT AAAACAAAAC ACTACCGTGC  1560
CCGTTTACTT ATCACCTTCC AGGC                                        1584
```

(2) INFORMATION FOR SEQ ID NO:4:

(i) SEQUENCE CHARACTERISTICS:

(A) LENGTH: 1191 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATGATTAACG CACGACTTGT GTTTCTTTTT GTATCAGTGT TATTACCAAT TTCAACAATG        60

GCCGATCCCC AGGAATTGTC TACAAGTATT AACCAGTTTG CTGGAAGCCT GTACAATACA       120

GTTGCTTCTG GCAACAAAGA CAATCTCATC ATGTCCCCAT TGTCTGTACA AACTGTTCTA       180

TCCCTGGTGT CAATGGGAGC TGGTGGCAAT ACTGCCACAC AAATAGCTGC TGGTTTGCGT       240

CAGCCTCAAT CAAAAGAAAA AATTCAAGAT GACTACCACG CATTGATGAA CACTCTTAAT       300

ACACAAAAAG GTGTAACTCT GGAAATTGCC AATAAAGTTT ATGTTATGGA AGGCTATACA       360

TTAAAACCCA CCTTCAAAGA AGTTGCCACC AACAAATTCT TAGCTGGAGC AGAAAACTTG       420

AACTTTGCCC AAAATGCTGA AGCGCTAAA GTTATCAACA CTTGGGTTGA AGAAAAAACT        480

CATGACAAAA TTCATGATTT GATCAAAGCC GGTGATCTAG ACCAGGATTC AAGAATGGTT       540

CTTGTCAATG CATTGTACTT CAAGGGTCTT TGGGAGAAAC AATTCAAAAA GGAAAATACC       600

CAAGACAAAC CTTTCTATGT TACTGAAACA GAGACAAAGA ATGTACGAAT GATGCACATT       660

AAGGATAAAT TCCGTTATGG AGAATTTGAA GAATTAGATG CCAAGGCTGT AGAATTGCCC       720

TACAGGAACT CAGATTTGGC CATGTTAATC ATTTTGCCAA ACAGCAAAAC TGGTCTCCCC       780

GCTCTTGAAG AAAAATTACA AAATGTTGAT TTGCAAAACT TGACTCAACG CATGTACTCT       840

GTTGAAGTTA TTTTGGATCT GCCTAAATTC AAGATTGAAT CTGAAATTAA TTTGAATGAT       900

CCTCTGAAAA AGTTGGGTAT GTCTGATATG TTTGTTCCTG GAAAAGCTGA TTTCAAAGGA       960

TTGCTTGAAG GATCTGATGA GATGTTATAT ATTTCTAAAG TAATTCAAAA AGCTTTCATT      1020

GAAGTAAATG AAGAAGGTGC TGAAGCTGCA GCTGCCACAG CTACCTTTAT GGTTACCTAT      1080

GAACTGGAGG TTTCCCTGGA TCTTCCCACT GTTTTTAAAG TCGATCATCC ATTCAATATT      1140

GTTTTGAAGA CAGGTGATAC TGTTATTTTT AATGGGCGAG TTCAAACTTT A               1191

(2) INFORMATION FOR SEQ ID NO:5:

(i) SEQUENCE CHARACTERISTICS:
        (A) LENGTH: 1191 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TAAAGTTTGA ACTCGCCCAT TAAAAATAAC AGTATCACCT GTCTTCAAAA CAATATTGAA        60

TGGATGATCG ACTTTAAAAA CAGTGGGAAG ATCCAGGGAA ACCTCCAGTT CATAGGTAAC       120

CATAAAGGTA GCTGTGGCAG CTGCAGCTTC AGCACCTTCT TCATTTACTT CAATGAAAGC       180

TTTTTGAATT ACTTTAGAAA TATATAACAT CTCATCAGAT CCTTCAAGCA ATCCTTTGAA       240

ATCAGCTTTT CCAGGAACAA ACATATCAGA CATACCCAAC TTTTTCAGAG GATCATTCAA       300

ATTAATTTCA GATTCAATCT TGAATTTAGG CAGATCCAAA ATAACTTCAA CAGAGTACAT       360

GCGTTGAGTC AAGTTTTGCA AATCAACATT TTGTAATTTT TCTTCAAGAG CGGGGAGACC       420

AGTTTTGCTG TTTGGCAAAA TGATTAACAT GGCCAAATCT GAGTTCCTGT AGGGCAATTC       480

TACAGCCTTG GCATCTAATT CTTCAAATTC TCCATAACGG AATTTATCCT TAATGTGCAT       540

```
CATTCGTACA TTCTTTGTCT CTGTTTCAGT AACATAGAAA GGTTTGTCTT GGGTATTTTC      600

CTTTTTGAAT TGTTTCTCCC AAAGACCCTT GAAGTACAAT GCATTGACAA GAACCATTCT      660

TGAATCCTGG TCTAGATCAC CGGCTTTGAT CAAATCATGA ATTTTGTCAT GAGTTTTTTC      720

TTCAACCCAA GTGTTGATAA CTTTAGCGCT TCAGCATTT TGGGCAAAGT TCAAGTTTTC       780

TGCTCCAGCT AAGAATTTGT TGGTGGCAAC TTCTTTGAAG GTGGGTTTTA ATGTATAGCC      840

TTCCATAACA TAAACTTTAT TGGCAATTTC CAGAGTTACA CCTTTTTGTG TATTAAGAGT      900

GTTCATCAAT GCGTGGTAGT CATCTTGAAT TTTTTCTTTT GATTGAGGCT GACGCAAACC      960

AGCAGCTATT TGTGTGGCAG TATTGCCACC AGCTCCCATT GACACCAGGG ATAGAACAGT     1020

TTGTACAGAC AATGGGGACA TGATGAGATT GTCTTTGTTG CCAGAAGCAA CTGTATTGTA     1080

CAGGCTTCCA GCAAACTGGT TAATACTTGT AGACAATTCC TGGGGATCGG CCATTGTTGA     1140

AATTGGTAAT AACACTGATA CAAAAAGAAA CACAAGTCGT GCGTTAATCA T             1191
```

(2) INFORMATION FOR SEQ ID NO:6:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:6:

```
Asp Pro Gln Glu Leu Ser Thr Ser Ile Asn Gln Phe Ala Gly Ser Leu
 1               5                  10                  15

Tyr Asn Thr Val Ala Ser Gly Asn Lys Asp Asn Leu Ile Met Ser Pro
            20                  25                  30

Leu Ser Val Gln Thr Val Leu Ser Leu Val Ser Met Gly Ala Gly Gly
        35                  40                  45

Asn Thr Ala Thr Gln Ile Ala Ala Gly Leu Arg Gln Pro Gln Ser Lys
 50                  55                  60

Glu Lys Ile Gln Asp Asp Tyr His Ala Leu Met Asn Thr Leu Asn Thr
65                  70                  75                  80

Gln Lys Gly Val Thr Leu Glu Ile Ala Asn Lys Val Tyr Val Met Glu
            85                  90                  95

Gly Tyr Thr Leu Lys Pro Thr Phe Lys Glu Val Ala Thr Asn Lys Phe
            100                 105                 110

Leu Ala Gly Ala Glu Asn Leu Asn Phe Ala Gln Asn Ala Glu Ser Ala
        115                 120                 125

Lys Val Ile Asn Thr Trp Val Glu Glu Lys Thr His Asp Lys Ile His
130                 135                 140

Asp Leu Ile Lys Ala Gly Asp Leu Asp Gln Asp Ser Arg Met Val Leu
145                 150                 155                 160

Val Asn Ala Leu Tyr Phe Lys Gly Leu Trp Glu Lys Gln Phe Lys Lys
            165                 170                 175

Glu Asn Thr Gln Asp Lys Pro Phe Tyr Val Thr Glu Thr Glu Thr Lys
            180                 185                 190

Asn Val Arg Met Met His Ile Lys Asp Lys Phe Arg Tyr Gly Glu Phe
            195                 200                 205

Glu Glu Leu Asp Ala Lys Ala Val Glu Leu Pro Tyr Arg Asn Ser Asp
        210                 215                 220

Leu Ala Met Leu Ile Ile Leu Pro Asn Ser Lys Thr Gly Leu Pro Ala
225                 230                 235                 240
```

```
Leu Glu Glu Lys Leu Gln Asn Val Asp Leu Gln Asn Leu Thr Gln Arg
            245                 250                 255

Met Tyr Ser Val Glu Val Ile Leu Asp Leu Pro Lys Phe Lys Ile Glu
            260                 265                 270

Ser Glu Ile Asn Leu Asn Asp Pro Leu Lys Lys Leu Gly Met Ser Asp
            275                 280                 285

Met Phe Val Pro Gly Lys Ala Asp Phe Lys Gly Leu Leu Glu Gly Ser
            290                 295                 300

Asp Glu Met Leu Tyr Ile Ser Lys Val Ile Gln Lys Ala Phe Ile Glu
305                 310                 315                 320

Val Asn Glu Glu Gly Ala Glu Ala Ala Ala Thr Ala Thr Phe Met
            325                 330                 335

Val Thr Tyr Glu Leu Glu Val Ser Leu Asp Leu Pro Thr Val Phe Lys
            340                 345                 350

Val Asp His Pro Phe Asn Ile Val Leu Lys Thr Gly Asp Thr Val Ile
            355                 360                 365

Phe Asn Gly Arg Val Gln Thr Leu
    370                 375

(2) INFORMATION FOR SEQ ID NO:7:

(i) SEQUENCE CHARACTERISTICS:
        (A) LENGTH: 1358 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..1198

(xi) SEQUENCE DESCRIPTION: SEQ ID NO:7:

C GCG ATA GTT CAA CAC GCA CGA CTT GTG TTT CTT TTT GTA TCA GTG          46
  Ala Ile Val Gln His Ala Arg Leu Val Phe Leu Phe Val Ser Val
  1               5                   10                  15

TTA ATA CCA ATT TCA ACA ATG GCG GAT CCC CAG GAA TTG TCT ACA AGT        94
Leu Ile Pro Ile Ser Thr Met Ala Asp Pro Gln Glu Leu Ser Thr Ser
                20                  25                  30

ATT AAC CAG TTT GCT GGA AGC CTG TAC AAT ACG GTT GCT TCT GGC AAC       142
Ile Asn Gln Phe Ala Gly Ser Leu Tyr Asn Thr Val Ala Ser Gly Asn
            35                  40                  45

AAA GAC AAT CTC ATC ATG TCC CCA TTG TCT GTA CAA ACT GTT CTA TCC       190
Lys Asp Asn Leu Ile Met Ser Pro Leu Ser Val Gln Thr Val Leu Ser
        50                  55                  60

CTG GTG TCA ATG GGA GCT GGT GGT AAT ACT GCC ACA CAA ATA GCT GCT       238
Leu Val Ser Met Gly Ala Gly Gly Asn Thr Ala Thr Gln Ile Ala Ala
    65                  70                  75

GGT TTA CGT CAG CCT CAA TCA AAA GAA AAA ATT CAA GAT GAC TAC CAT       286
Gly Leu Arg Gln Pro Gln Ser Lys Glu Lys Ile Gln Asp Asp Tyr His
80                  85                  90                  95

GCA TTG ATG AAC ACT CTT AAT ACA CAA AAA GGT GTA ACT CTG GAA ATT       334
Ala Leu Met Asn Thr Leu Asn Thr Gln Lys Gly Val Thr Leu Glu Ile
                100                 105                 110

GCC AAC AAA GTT TAC GTT ATG GAA GGC TAT ACA TTG AAA CCC ACC TTC       382
Ala Asn Lys Val Tyr Val Met Glu Gly Tyr Thr Leu Lys Pro Thr Phe
            115                 120                 125

AAA GAA GTT GCC ACC AAC AAA TTC TTA GCT GGA GCA GAA AAC TTG AAC       430
Lys Glu Val Ala Thr Asn Lys Phe Leu Ala Gly Ala Glu Asn Leu Asn
```

```
                130                     135                     140
TTT GCC CAA AAT GCT GAA AGC GCT AAA GTT ATC AAC ACT TGG GTT GAA     478
Phe Ala Gln Asn Ala Glu Ser Ala Lys Val Ile Asn Thr Trp Val Glu
        145                     150                     155

GAA AAA ACT CAT GAC AAA ATT CAT GAT TTG ATC AAA GCC GGT GAT CTA     526
Glu Lys Thr His Asp Lys Ile His Asp Leu Ile Lys Ala Gly Asp Leu
160                     165                     170                 175

GAC CAG GAT TCA AGA ATG GTT CTT GTC AAT GCA TTG TAC TTC AAG GGT     574
Asp Gln Asp Ser Arg Met Val Leu Val Asn Ala Leu Tyr Phe Lys Gly
                180                     185                     190

CTT TGG GAG AAA CAA TTC AAG AAG GAA AAC ACT CAA GAC AAA CCT TTC     622
Leu Trp Glu Lys Gln Phe Lys Lys Glu Asn Thr Gln Asp Lys Pro Phe
        195                     200                     205

TAT GTT ACT GAA ACA GAG ACA AAG AAT GTA CGA ATG ATG CAC ATT AAG     670
Tyr Val Thr Glu Thr Glu Thr Lys Asn Val Arg Met Met His Ile Lys
            210                     215                     220

GAT AAA TTC CGT TAT GGA GAA TTT GAA GAA TTA GAT GCC AAG GCT GTA     718
Asp Lys Phe Arg Tyr Gly Glu Phe Glu Glu Leu Asp Ala Lys Ala Val
        225                     230                     235

GAA TTG CCC TAC AGG AAC TCA GAT TTG GCC ATG TTA ATC ATT TTG CCA     766
Glu Leu Pro Tyr Arg Asn Ser Asp Leu Ala Met Leu Ile Ile Leu Pro
240                     245                     250                 255

AAC AGC AAA ACT GGT CTC CCC GCT CTT GAA GAA AAA TTA CAA AAT GTT     814
Asn Ser Lys Thr Gly Leu Pro Ala Leu Glu Glu Lys Leu Gln Asn Val
                260                     265                     270

GAC TTG CAA AAC TTG ACT CAA CGC ATG TAC TCT GTT GAA GTT ATT TTG     862
Asp Leu Gln Asn Leu Thr Gln Arg Met Tyr Ser Val Glu Val Ile Leu
        275                     280                     285

GAT CTG CCT AAA TTC AAG ATT GAA TCT GAA ATT AAT TTG AAT GAT CCT     910
Asp Leu Pro Lys Phe Lys Ile Glu Ser Glu Ile Asn Leu Asn Asp Pro
        290                     295                     300

CTG AAA AAG TTG GGT ATG TCT GAT ATG TTT GTT CCT GGA AAA GCT GAT     958
Leu Lys Lys Leu Gly Met Ser Asp Met Phe Val Pro Gly Lys Ala Asp
        305                     310                     315

TTC AAA GGA TTG CTT GAA GGA TCT GAT GAG ATG TTA TAT ATT TCT AAA    1006
Phe Lys Gly Leu Leu Glu Gly Ser Asp Glu Met Leu Tyr Ile Ser Lys
320                     325                     330                 335

GTA ATT CAA AAA GCT TTC ATT GAA GTA AAT GAA GAA GGT GCT GAA GCT    1054
Val Ile Gln Lys Ala Phe Ile Glu Val Asn Glu Glu Gly Ala Glu Ala
                340                     345                     350

GCA GCT GCC ACA GGC ATT GTC ATG CTT GGT TGC TGT ATG CCA ATG ATG    1102
Ala Ala Ala Thr Gly Ile Val Met Leu Gly Cys Cys Met Pro Met Met
            355                     360                     365

GAT CTT TCT CCA GTA GTT TTT AAT ATT GAT CAC CCA TTT TAT TAC TCA    1150
Asp Leu Ser Pro Val Val Phe Asn Ile Asp His Pro Phe Tyr Tyr Ser
        370                     375                     380

TTG ATG ACT TGG GAT ACT GTT TTG TTC AGT GGA TGT GTT AAA TCC CTT    1198
Leu Met Thr Trp Asp Thr Val Leu Phe Ser Gly Cys Val Lys Ser Leu
        385                     390                     395

TAA ATTCTTCTT AGAATGAAGG TATTTCAGTG TCTAATGGCA TTGATAGACC          1251

CAAAAATTTC AATTCTGACC ATGCTTTCTA CCTCATGATA ACGGCAGGGA AAACGATTTC  1311

AATTAGAGGT CGTTTCTATA ACTCCTAGTA TATGTTATAT GACTAGT              1358
```

(2) INFORMATION FOR SEQ ID NO:8:

(i) SEQUENCE CHARACTERISTICS:
        (A) LENGTH: 399 amino acids
        (B) TYPE: amino acid
        (D) TOPOLOGY: linear -continued (ii) MOLECULE TYPE:  protein (xi) SEQUENCE DESCRIPTION: SEQ ID NO:8:

Ala Ile Val Gln His Ala Arg Leu Val Phe Leu Phe Val Ser Val Leu
 1               5                  10                  15

Ile Pro Ile Ser Thr Met Ala Asp Pro Gln Glu Leu Ser Thr Ser Ile
                20                  25                  30

Asn Gln Phe Ala Gly Ser Leu Tyr Asn Thr Val Ala Ser Gly Asn Lys
            35                  40                  45

Asp Asn Leu Ile Met Ser Pro Leu Ser Val Gln Thr Val Leu Ser Leu
        50                  55                  60

Val Ser Met Gly Ala Gly Gly Asn Thr Ala Thr Gln Ile Ala Ala Gly
65                  70                  75                  80

Leu Arg Gln Pro Gln Ser Lys Glu Lys Ile Gln Asp Asp Tyr His Ala
                85                  90                  95

Leu Met Asn Thr Leu Asn Thr Gln Lys Gly Val Thr Leu Glu Ile Ala
            100                 105                 110

Asn Lys Val Tyr Val Met Glu Gly Tyr Thr Leu Lys Pro Thr Phe Lys
        115                 120                 125

Glu Val Ala Thr Asn Lys Phe Leu Ala Gly Ala Glu Asn Leu Asn Phe
    130                 135                 140

Ala Gln Asn Ala Glu Ser Ala Lys Val Ile Asn Thr Trp Val Glu Glu
145                 150                 155                 160

Lys Thr His Asp Lys Ile His Asp Leu Ile Lys Ala Gly Asp Leu Asp
                165                 170                 175

Gln Asp Ser Arg Met Val Leu Val Asn Ala Leu Tyr Phe Lys Gly Leu
            180                 185                 190

Trp Glu Lys Gln Phe Lys Lys Glu Asn Thr Gln Asp Lys Pro Phe Tyr
        195                 200                 205

Val Thr Glu Thr Glu Thr Lys Asn Val Arg Met Met His Ile Lys Asp
    210                 215                 220

Lys Phe Arg Tyr Gly Glu Phe Glu Glu Leu Asp Ala Lys Ala Val Glu
225                 230                 235                 240

Leu Pro Tyr Arg Asn Ser Asp Leu Ala Met Leu Ile Ile Leu Pro Asn
                245                 250                 255

Ser Lys Thr Gly Leu Pro Ala Leu Glu Glu Lys Leu Gln Asn Val Asp
            260                 265                 270

Leu Gln Asn Leu Thr Gln Arg Met Tyr Ser Val Glu Val Ile Leu Asp
        275                 280                 285

Leu Pro Lys Phe Lys Ile Glu Ser Glu Ile Asn Leu Asn Asp Pro Leu
    290                 295                 300

Lys Lys Leu Gly Met Ser Asp Met Phe Val Pro Gly Lys Ala Asp Phe
305                 310                 315                 320

Lys Gly Leu Leu Glu Gly Ser Asp Glu Met Leu Tyr Ile Ser Lys Val
                325                 330                 335

Ile Gln Lys Ala Phe Ile Glu Val Asn Glu Glu Gly Ala Glu Ala Ala
            340                 345                 350

Ala Ala Thr Gly Ile Val Met Leu Gly Cys Cys Met Pro Met Met Asp
        355                 360                 365

Leu Ser Pro Val Val Phe Asn Ile Asp His Pro Phe Tyr Tyr Ser Leu
    370                 375                 380

Met Thr Trp Asp Thr Val Leu Phe Ser Gly Cys Val Lys Ser Leu
385                 390                 395

(2) INFORMATION FOR SEQ ID NO:9:

(i) SEQUENCE CHARACTERISTICS:
        (A) LENGTH: 1358 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
ACTAGTCATA TAACATATAC TAGGAGTTAT AGAAACGACC TCTAATTGAA ATCGTTTTCC      60

CTGCCGTTAT CATGAGGTAG AAAGCATGGT CAGAATTGAA ATTTTTGGGT CTATCAATGC     120

CATTAGACAC TGAAATACCT TCATTCTAAG AAGAAATTTA AAGGGATTTA ACACATCCAC     180

TGAACAAAAC AGTATCCCAA GTCATCAATG AGTAATAAAA TGGGTGATCA ATATTAAAAA     240

CTACTGGAGA AAGATCCATC ATTGGCATAC AGCAACCAAG CATGACAATG CCTGTGGCAG     300

CTGCAGCTTC AGCACCTTCT TCATTTACTT CAATGAAAGC TTTTTGAATT ACTTTAGAAA     360

TATATAACAT CTCATCAGAT CCTTCAAGCA ATCCTTTGAA ATCAGCTTTT CCAGGAACAA     420

ACATATCAGA CATACCCAAC TTTTTCAGAG GATCATTCAA ATTAATTTCA GATTCAATCT     480

TGAATTTAGG CAGATCCAAA ATAACTTCAA CAGAGTACAT GCGTTGAGTC AAGTTTTGCA     540

AGTCAACATT TTGTAATTTT TCTTCAAGAG CGGGGAGACC AGTTTTGCTG TTTGGCAAAA     600

TGATTAACAT GGCCAAATCT GAGTTCCTGT AGGGCAATTC TACAGCCTTG GCATCTAATT     660

CTTCAAATTC TCCATAACGG AATTTATCCT TAATGTGCAT CATTCGTACA TTCTTTGTCT     720

CTGTTTCAGT AACATAGAAA GGTTTGTCTT GAGTGTTTTC CTTCTTGAAT TGTTTCTCCC     780

AAAGACCCTT GAAGTACAAT GCATTGACAA GAACCATTCT TGAATCCTGG TCTAGATCAC     840

CGGCTTTGAT CAAATCATGA ATTTTGTCAT GAGTTTTTTC TTCAACCCAA GTGTTGATAA     900

CTTTAGCGCT TTCAGCATTT TGGGCAAAGT TCAAGTTTTC TGCTCCAGCT AAGAATTTGT     960

TGGTGGCAAC TTCTTTGAAG GTGGGTTTCA ATGTATAGCC TTCCATAACG TAAACTTTGT    1020

TGGCAATTTC CAGAGTTACA CCTTTTTGTG TATTAAGAGT GTTCATCAAT GCATGGTAGT    1080

CATCTTGAAT TTTTTCTTTT GATTGAGGCT GACGTAAACC AGCAGCTATT TGTGTGGCAG    1140

TATTACCACC AGCTCCCATT GACACCAGGG ATAGAACAGT TTGTACAGAC AATGGGACA    1200

TGATGAGATT GTCTTTGTTG CCAGAAGCAA CCGTATTGTA CAGGCTTCCA GCAAACTGGT    1260

TAATACTTGT AGACAATTCC TGGGGATCCG CCATTGTTGA AATTGGTATT AACACTGATA    1320

CAAAAGAAA CACAAGTCGT GCGTGTTGAA CTATCGCG                             1358
```

(2) INFORMATION FOR SEQ ID NO:10:

(i) SEQUENCE CHARACTERISTICS:
        (A) LENGTH: 1197 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GCGATAGTTC AACACGCACG ACTTGTGTTT CTTTTTGTAT CAGTGTTAAT ACCAATTTCA      60

ACAATGGCGG ATCCCCAGGA ATTGTCTACA AGTATTAACC AGTTTGCTGG AAGCCTGTAC     120

AATACGGTTG CTTCTGGCAA CAAAGACAAT CTCATCATGT CCCCATTGTC TGTACAAACT     180
```

```
GTTCTATCCC TGGTGTCAAT GGGAGCTGGT GGTAATACTG CCACACAAAT AGCTGCTGGT    240

TTACGTCAGC CTCAATCAAA AGAAAAAATT CAAGATGACT ACCATGCATT GATGAACACT    300

CTTAATACAC AAAAAGGTGT AACTCTGGAA ATTGCCAACA AAGTTTACGT TATGGAAGGC    360

TATACATTGA AACCCACCTT CAAAGAAGTT GCCACCAACA AATTCTTAGC TGGAGCAGAA    420

AACTTGAACT TTGCCCAAAA TGCTGAAAGC GCTAAAGTTA TCAACACTTG GGTTGAAGAA    480

AAAACTCATG ACAAAATTCA TGATTTGATC AAAGCCGGTG ATCTAGACCA GGATTCAAGA    540

ATGGTTCTTG TCAATGCATT GTACTTCAAG GGTCTTTGGG AGAAACAATT CAAGAAGGAA    600

AACACTCAAG ACAAACCTTT CTATGTTACT GAAACAGAGA CAAAGAATGT ACGAATGATG    660

CACATTAAGG ATAAATTCCG TTATGGAGAA TTTGAAGAAT TAGATGCCAA GGCTGTAGAA    720

TTGCCCTACA GGAACTCAGA TTTGGCCATG TTAATCATTT TGCCAAACAG CAAAACTGGT    780

CTCCCCGCTC TTGAAGAAAA ATTACAAAAT GTTGACTTGC AAAACTTGAC TCAACGCATG    840

TACTCTGTTG AAGTTATTTT GGATCTGCCT AAATTCAAGA TTGAATCTGA AATTAATTTG    900

AATGATCCTC TGAAAAAGTT GGGTATGTCT GATATGTTTG TTCCTGGAAA AGCTGATTTC    960

AAAGGATTGC TTGAAGGATC TGATGAGATG TTATATATTT CTAAAGTAAT TCAAAAAGCT   1020

TTCATTGAAG TAAATGAAGA AGGTGCTGAA GCTGCAGCTG CCACAGGCAT TGTCATGCTT   1080

GGTTGCTGTA TGCCAATGAT GGATCTTTCT CCAGTAGTTT TAATATTGA TCACCCATTT    1140

TATTACTCAT TGATGACTTG GGATACTGTT TTGTTCAGTG GATGTGTTAA ATCCCTT      1197

(2) INFORMATION FOR SEQ ID NO:11:

(i) SEQUENCE CHARACTERISTICS:
        (A) LENGTH: 1197 nucleic acid
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

AAGGGATTTA ACACATCCAC TGAACAAAAC AGTATCCCAA GTCATCAATG AGTAATAAAA     60

TGGGTGATCA ATATTAAAAA CTACTGGAGA AAGATCCATC ATTGGCATAC AGCAACCAAG    120

CATGACAATG CCTGTGGCAG CTGCAGCTTC AGCACCTTCT TCATTTACTT CAATGAAAGC    180

TTTTTGAATT ACTTTAGAAA TATATAACAT CTCATCAGAT CCTTCAAGCA ATCCTTTGAA    240

ATCAGCTTTT CCAGGAACAA ACATATCAGA CATACCCAAC TTTTTCAGAG GATCATTCAA    300

ATTAATTTCA GATTCAATCT TGAATTTAGG CAGATCCAAA ATAACTTCAA CAGAGTACAT    360

GCGTTGAGTC AAGTTTTGCA AGTCAACATT TTGTAATTTT TCTTCAAGAG CGGGGAGACC    420

AGTTTTGCTG TTTGGCAAAA TGATTAACAT GGCCAAATCT GAGTTCCTGT AGGGCAATTC    480

TACAGCCTTG GCATCTAATT CTTCAAATTC TCCATAACGG AATTTATCCT TAATGTGCAT    540

CATTCGTACA TTCTTTGTCT CTGTTTCAGT AACATAGAAA GGTTTGTCTT GAGTGTTTTC    600

CTTCTTGAAT TGTTTCTCCC AAAGACCCTT GAAGTACAAT GCATTGACAA GAACCATTCT    660

TGAATCCTGG TCTAGATCAC CGGCTTTGAT CAAATCATGA ATTTTGTCAT GAGTTTTTTC    720

TTCAACCCAA GTGTTGATAA CTTTAGCGCT TTCAGCATTT TGGGCAAAGT TCAAGTTTTC    780

TGCTCCAGCT AAGAATTTGT TGGTGGCAAC TTCTTTGAAG GTGGGTTTCA ATGTATAGCC    840

TTCCATAACG TAAACTTTGT TGGCAATTTC CAGAGTTACA CCTTTTTGTG TATTAAGAGT    900

GTTCATCAAT GCATGGTAGT CATCTTGAAT TTTTTCTTTT GATTGAGGCT GACGTAAACC    960
```

```
AGCAGCTATT TGTGTGGCAG TATTACCACC AGCTCCCATT GACACCAGGG ATAGAACAGT    1020

TTGTACAGAC AATGGGGACA TGATGAGATT GTCTTTGTTG CCAGAAGCAA CCGTATTGTA    1080

CAGGCTTCCA GCAAACTGGT TAATACTTGT AGACAATTCC TGGGGATCCG CCATTGTTGA    1140

AATTGGTATT AACACTGATA CAAAAGAAA CACAAGTCGT GCGTGTTGAA CTATCGC       1197
```

(2) INFORMATION FOR SEQ ID NO:12:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Pro Gln Glu Leu Ser Thr Ser Ile Asn Gln Phe Ala Gly Ser Leu
 1               5                  10                  15

Tyr Asn Thr Val Ala Ser Gly Asn Lys Asp Asn Leu Ile Met Ser Pro
            20                  25                  30

Leu Ser Val Gln Thr Val Leu Ser Leu Val Ser Met Gly Ala Gly Gly
        35                  40                  45

Asn Thr Ala Thr Gln Ile Ala Ala Gly Leu Arg Gln Pro Gln Ser Lys
    50                  55                  60

Glu Lys Ile Gln Asp Asp Tyr His Ala Leu Met Asn Thr Leu Asn Thr
65                  70                  75                  80

Gln Lys Gly Val Thr Leu Glu Ile Ala Asn Lys Val Tyr Val Met Glu
                85                  90                  95

Gly Tyr Thr Leu Lys Pro Thr Phe Lys Glu Val Ala Thr Asn Lys Phe
            100                 105                 110

Leu Ala Gly Ala Glu Asn Leu Asn Phe Ala Gln Asn Ala Glu Ser Ala
        115                 120                 125

Lys Val Ile Asn Thr Trp Val Glu Glu Lys Thr His Asp Lys Ile His
    130                 135                 140

Asp Leu Ile Lys Ala Gly Asp Leu Asp Gln Asp Ser Arg Met Val Leu
145                 150                 155                 160

Val Asn Ala Leu Tyr Phe Lys Gly Leu Trp Glu Lys Gln Phe Lys Lys
                165                 170                 175

Glu Asn Thr Gln Asp Lys Pro Phe Tyr Val Thr Glu Thr Glu Thr Lys
            180                 185                 190

Asn Val Arg Met Met His Ile Lys Asp Lys Phe Arg Tyr Gly Glu Phe
        195                 200                 205

Glu Glu Leu Asp Ala Lys Ala Val Glu Leu Pro Tyr Arg Asn Ser Asp
    210                 215                 220

Leu Ala Met Leu Ile Ile Leu Pro Asn Ser Lys Thr Gly Leu Pro Ala
225                 230                 235                 240

Leu Glu Glu Lys Leu Gln Asn Val Asp Leu Gln Asn Leu Thr Gln Arg
                245                 250                 255

Met Tyr Ser Val Glu Val Ile Leu Asp Leu Pro Lys Phe Lys Ile Glu
            260                 265                 270

Ser Glu Ile Asn Leu Asn Asp Pro Leu Lys Leu Gly Met Ser Asp
        275                 280                 285

Met Phe Val Pro Gly Lys Ala Asp Phe Lys Gly Leu Leu Glu Gly Ser
    290                 295                 300

Asp Glu Met Leu Tyr Ile Ser Lys Val Ile Gln Lys Ala Phe Ile Glu
305                 310                 315                 320
```

Val Asn Glu Glu Gly Ala Glu Ala Ala Ala Thr Gly Ile Val Met
            325                 330                 335

Leu Gly Cys Cys Met Pro Met Met Asp Leu Ser Pro Val Val Phe Asn
            340                 345                 350

Ile Asp His Pro Phe Tyr Tyr Ser Leu Met Thr Trp Asp Thr Val Leu
        355                 360                 365

Phe Ser Gly Cys Val Lys Ser Leu
370                 375

(2) INFORMATION FOR SEQ ID NO:13:

(i) SEQUENCE CHARACTERISTICS:
        (A) LENGTH: 1838 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 306..1565

(xi) SEQUENCE DESCRIPTION: SEQ ID NO:13:

```
ATTGTGCAAA GTCAAATTAC GCATTTAGAA TATTAAAATC AGTATCTCCA AAAATACATA      60

CAAATCAATT CAATAACTAT CATTCAAATG ACATCATGTT CAAATAAAT TAAACACAAA     120

TATAAAAATG AAGCTAATTT TTGGAAACTG TGTGATTCCA AGGACGACAG AAATATAAAA    180

CAGATTCATG TGTGTTGTTC CGCGAAGCCA AATGTTTGAA TGTATATAGT GTGTTATTCA    240

AACATTCCTA GTATTTCTAT ATTATACAAT ATGACTCACA AACGATTCTA ATATCTAGAG    300
```

TTTTG ATG CCG CGT CCT CAG TTT GAC GCG ATA GTT CAA CAC GCA CGA CTT      350
     Met Pro Arg Pro Gln Phe Asp Ala Ile Val Gln His Ala Arg Leu
      1               5                  10                  15

GTG TTT CTT TTT GTA TCA GTG TTA ATA CCA ATT TCA ACA ATG GCG GAT       398
Val Phe Leu Phe Val Ser Val Leu Ile Pro Ile Ser Thr Met Ala Asp
                20                  25                  30

CCC CAG GAA TTG TCT ACA AGT ATT AAC CAG TTT GCT GGA AGC CTG TAC       446
Pro Gln Glu Leu Ser Thr Ser Ile Asn Gln Phe Ala Gly Ser Leu Tyr
            35                  40                  45

AAT ACG GTT GCT TCT GGC AAC AAA GAC AAT CTC ATC ATG TCC CCA TTG       494
Asn Thr Val Ala Ser Gly Asn Lys Asp Asn Leu Ile Met Ser Pro Leu
        50                  55                  60

TCT GTA CAA ACT GTT CTA TCC CTG GTG TCA ATG GGA GCT GGT GGT AAT       542
Ser Val Gln Thr Val Leu Ser Leu Val Ser Met Gly Ala Gly Gly Asn
65                  70                  75

ACT GCC ACA CAA ATA GCT GCT GGT TTA CGT CAG CCT CAA TCA AAA GAA       590
Thr Ala Thr Gln Ile Ala Ala Gly Leu Arg Gln Pro Gln Ser Lys Glu
80                  85                  90                  95

AAA ATT CAA GAT GAC TAC CAT GCA TTG ATG AAC ACT CTT AAT ACA CAA       638
Lys Ile Gln Asp Asp Tyr His Ala Leu Met Asn Thr Leu Asn Thr Gln
                100                 105                 110

AAA GGT GTA ACT CTG GAA ATT GCC AAC AAA GTT TAC GTT ATG GAA GGC       686
Lys Gly Val Thr Leu Glu Ile Ala Asn Lys Val Tyr Val Met Glu Gly
            115                 120                 125

TAT ACA TTG AAA CCC ACC TTC AAA GAA GTT GCC ACC AAC AAA TTC TTA       734
Tyr Thr Leu Lys Pro Thr Phe Lys Glu Val Ala Thr Asn Lys Phe Leu
        130                 135                 140

GCT GGA GCA GAA AAC TTG AAC TTT GCC CAA AAT GCT GAA AGC GCT AAA       782
Ala Gly Ala Glu Asn Leu Asn Phe Ala Gln Asn Ala Glu Ser Ala Lys
145                 150                 155

```
GTT ATC AAC ACT TGG GTT GAA GAA AAA ACT CAT GAC AAA ATT CAT GAT      830
Val Ile Asn Thr Trp Val Glu Glu Lys Thr His Asp Lys Ile His Asp
160                 165                 170                 175

TTG ATC AAA GCC GGT GAT CTA GAC CAG GAT TCA AGA ATG GTT CTT GTC      878
Leu Ile Lys Ala Gly Asp Leu Asp Gln Asp Ser Arg Met Val Leu Val
                180                 185                 190

AAT GCA TTG TAC TTC AAG GGT CTT TGG GAG AAA CAA TTC AAG AAG GAA      926
Asn Ala Leu Tyr Phe Lys Gly Leu Trp Glu Lys Gln Phe Lys Lys Glu
            195                 200                 205

AAC ACT CAA GAC AAA CCT TTC TAT GTT ACT GAA ACA GAG ACA AAG AAT      974
Asn Thr Gln Asp Lys Pro Phe Tyr Val Thr Glu Thr Glu Thr Lys Asn
        210                 215                 220

GTA CGA ATG ATG CAC ATT AAG GAT AAA TTC CGT TAT GGA GAA TTT GAA     1022
Val Arg Met Met His Ile Lys Asp Lys Phe Arg Tyr Gly Glu Phe Glu
    225                 230                 235

GAA TTA GAT GCC AAG GCT GTA GAA TTG CCC TAC AGG AAC TCA GAT TTG     1070
Glu Leu Asp Ala Lys Ala Val Glu Leu Pro Tyr Arg Asn Ser Asp Leu
240                 245                 250                 255

GCC ATG TTA ATC ATT TTG CCA AAC AGC AAA ACT GGT CTC CCC GCT CTT     1118
Ala Met Leu Ile Ile Leu Pro Asn Ser Lys Thr Gly Leu Pro Ala Leu
                260                 265                 270

GAA GAA AAA TTA CAA AAT GTT GAC TTG CAA AAC TTG ACT CAA CGC ATG     1166
Glu Glu Lys Leu Gln Asn Val Asp Leu Gln Asn Leu Thr Gln Arg Met
            275                 280                 285

TAC TCT GTT GAA GTT ATT TTG GAT CTG CCT AAA TTC AAG ATT GAA TCT     1214
Tyr Ser Val Glu Val Ile Leu Asp Leu Pro Lys Phe Lys Ile Glu Ser
        290                 295                 300

GAA ATT AAT TTG AAT GAT CCT CTG AAA AAG TTG GGT ATG TCT GAT ATG     1262
Glu Ile Asn Leu Asn Asp Pro Leu Lys Lys Leu Gly Met Ser Asp Met
    305                 310                 315

TTT GTT CCT GGA AAA GCT GAT TTC AAA GGA TTG CTT GAA GGA TCT GAT     1310
Phe Val Pro Gly Lys Ala Asp Phe Lys Gly Leu Leu Glu Gly Ser Asp
320                 325                 330                 335

GAG ATG TTA TAT ATT TCT AAA GTA ATT CAA AAA GCT TTC ATT GAA GTA     1358
Glu Met Leu Tyr Ile Ser Lys Val Ile Gln Lys Ala Phe Ile Glu Val
                340                 345                 350

AAT GAA GAA GGT GCT GAA GCT GCA GCT GCC ACA GCG GTG CTT TTA GTA     1406
Asn Glu Glu Gly Ala Glu Ala Ala Ala Ala Thr Ala Val Leu Leu Val
            355                 360                 365

ACG GAA TCT TAT GTA CCT GAG GAA GTA TTC GAA GCT AAT CAT CCC TTT     1454
Thr Glu Ser Tyr Val Pro Glu Glu Val Phe Glu Ala Asn His Pro Phe
        370                 375                 380

TAT TTT GCA CTC TAT AAA TCT GCA CAA AAT CCA GTA GAA TCT GAA AAT     1502
Tyr Phe Ala Leu Tyr Lys Ser Ala Gln Asn Pro Val Glu Ser Glu Asn
    385                 390                 395

GAA AGC TCT GAA AAT GAA AAC CCT GAA AAT GTT GAA GTA CTA TTC TCT     1550
Glu Ser Ser Glu Asn Glu Asn Pro Glu Asn Val Glu Val Leu Phe Ser
400                 405                 410                 415

GGG AGA TTT ACC AAT TAG AAAAATATGT GTTACTAGCC TTGTGATTAT            1598
Gly Arg Phe Thr Asn
                420

AAGCAGGACA AATTTCAAAA ATACAAGATC TATCTGAATC TCTGGATTAA TGAAGTAATT   1658

TTTCTACAAT ATTTTTTAAT AGTTATTAGG TCTAAAATAA GTTCATTTTT TAGTATGTGG   1718

TATAAATCGT GTAGACGAAA AATGTTTTGT TTTAGTTTTC ACTTTTTATG AATGTAATCA   1778

CCTATATAAT GTTGTAGTTT ATGTAATAAA AATGTTAAAT GTGAAAAAAA AAAAAAAAAA   1838
```

(2) INFORMATION FOR SEQ ID NO:14:

(i) SEQUENCE CHARACTERISTICS:
        (A) LENGTH: 420 amino acids
        (B) TYPE: amino acid
        (D) TOPOLOGY: linear (ii) MOLECULE TYPE: protein (xi) SEQUENCE DESCRIPTION: SEQ ID NO:14:

Met Pro Arg Pro Gln Phe Asp Ala Ile Val Gln His Ala Arg Leu Val
  1               5                  10                  15

Phe Leu Phe Val Ser Val Leu Ile Pro Ile Ser Thr Met Ala Asp Pro
                 20                  25                  30

Gln Glu Leu Ser Thr Ser Ile Asn Gln Phe Ala Gly Ser Leu Tyr Asn
             35                  40                  45

Thr Val Ala Ser Gly Asn Lys Asp Asn Leu Ile Met Ser Pro Leu Ser
         50                  55                  60

Val Gln Thr Val Leu Ser Leu Val Ser Met Gly Ala Gly Gly Asn Thr
 65                  70                  75                  80

Ala Thr Gln Ile Ala Ala Gly Leu Arg Gln Pro Gln Ser Lys Glu Lys
                 85                  90                  95

Ile Gln Asp Asp Tyr His Ala Leu Met Asn Thr Leu Asn Thr Gln Lys
                100                 105                 110

Gly Val Thr Leu Glu Ile Ala Asn Lys Val Tyr Val Met Glu Gly Tyr
            115                 120                 125

Thr Leu Lys Pro Thr Phe Lys Glu Val Ala Thr Asn Lys Phe Leu Ala
        130                 135                 140

Gly Ala Glu Asn Leu Asn Phe Ala Gln Asn Ala Glu Ser Ala Lys Val
145                 150                 155                 160

Ile Asn Thr Trp Val Glu Glu Lys Thr His Asp Lys Ile His Asp Leu
                165                 170                 175

Ile Lys Ala Gly Asp Leu Asp Gln Asp Ser Arg Met Val Leu Val Asn
                180                 185                 190

Ala Leu Tyr Phe Lys Gly Leu Trp Glu Lys Gln Phe Lys Lys Glu Asn
            195                 200                 205

Thr Gln Asp Lys Pro Phe Tyr Val Thr Glu Thr Glu Thr Lys Asn Val
        210                 215                 220

Arg Met Met His Ile Lys Asp Lys Phe Arg Tyr Gly Glu Phe Glu Glu
225                 230                 235                 240

Leu Asp Ala Lys Ala Val Glu Leu Pro Tyr Arg Asn Ser Asp Leu Ala
                245                 250                 255

Met Leu Ile Ile Leu Pro Asn Ser Lys Thr Gly Leu Pro Ala Leu Glu
                260                 265                 270

Glu Lys Leu Gln Asn Val Asp Leu Gln Asn Leu Thr Gln Arg Met Tyr
            275                 280                 285

Ser Val Glu Val Ile Leu Asp Leu Pro Lys Phe Lys Ile Glu Ser Glu
        290                 295                 300

Ile Asn Leu Asn Asp Pro Leu Lys Leu Gly Met Ser Asp Met Phe
305                 310                 315                 320

Val Pro Gly Lys Ala Asp Phe Lys Gly Leu Leu Glu Gly Ser Asp Glu
                325                 330                 335

Met Leu Tyr Ile Ser Lys Val Ile Gln Lys Ala Phe Ile Glu Val Asn
            340                 345                 350

Glu Glu Gly Ala Glu Ala Ala Ala Thr Ala Val Leu Leu Val Thr
        355                 360                 365

```
Glu Ser Tyr Val Pro Glu Val Phe Glu Ala Asn His Pro Phe Tyr
    370                 375                 380

Phe Ala Leu Tyr Lys Ser Ala Gln Asn Pro Val Glu Ser Glu Asn Glu
385                 390                 395                 400

Ser Ser Glu Asn Glu Asn Pro Glu Asn Val Glu Val Leu Phe Ser Gly
                405                 410                 415

Arg Phe Thr Asn
            420

(2) INFORMATION FOR SEQ ID NO:15:

(i) SEQUENCE CHARACTERISTICS:
        (A) LENGTH: 1838 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TTTTTTTTTT TTTTTTTCAC ATTTAACATT TTTATTACAT AAACTACAAC ATTATATAGG      60

TGATTACATT CATAAAAAGT GAAAACTAAA ACAAACATT TTTCGTCTAC ACGATTTATA     120

CCACATACTA AAAAATGAAC TTATTTTAGA CCTAATAACT ATTAAAAAAT ATTGTAGAAA     180

AATTACTTCA TTAATCCAGA GATTCAGATA GATCTTGTAT TTTTGAAATT TGTCCTGCTT     240

ATAATCACAA GGCTAGTAAC ACATATTTTT CTAATTGGTA AATCTCCCAG AGAATAGTAC     300

TTCAACATTT TCAGGGTTTT CATTTTCAGA GCTTTCATTT TCAGATTCTA CTGGATTTTG     360

TGCAGATTTA TAGAGTGCAA AATAAAAGGG ATGATTAGCT TCGAATACTT CCTCAGGTAC     420

ATAAGATTCC GTTACTAAAA GCACCGCTGT GGCAGCTGCA GCTTCAGCAC CTTCTTCATT     480

TACTTCAATG AAAGCTTTTT GAATTACTTT AGAAATATAT AACATCTCAT CAGATCCTTC     540

AAGCAATCCT TTGAAATCAG CTTTTCCAGG AACAAACATA TCAGACATAC CCAACTTTTT     600

CAGAGGATCA TTCAAATTAA TTTCAGATTC AATCTTGAAT TTAGGCAGAT CCAAAATAAC     660

TTCAACAGAG TACATGCGTT GAGTCAAGTT TGCAAGTCA ACATTTGTA ATTTTTCTTC      720

AAGAGCGGGG AGACCAGTTT TGCTGTTTGG CAAAATGATT AACATGGCCA AATCTGAGTT     780

CCTGTAGGGC AATTCTACAG CCTTGGCATC TAATTCTTCA AATTCTCCAT AACGGAATTT     840

ATCCTTAATG TGCATCATTC GTACATTCTT TGTCTCTGTT TCAGTAACAT AGAAAGGTTT     900

GTCTTGAGTG TTTTCCTTCT TGAATTGTTT CTCCCAAAGA CCCTTGAAGT ACAATGCATT     960

GACAAGAACC ATTCTTGAAT CCTGGTCTAG ATCACCGGCT TTGATCAAAT CATGAATTTT    1020

GTCATGAGTT TTTTCTTCAA CCCAAGTGTT GATAACTTTA GCGCTTTCAG CATTTTGGGC    1080

AAAGTTCAAG TTTTCTGCTC CAGCTAAGAA TTTGTTGGTG GCAACTTCTT TGAAGGTGGG    1140

TTTCAATGTA TAGCCTTCCA TAACGTAAAC TTTGTTGGCA ATTTCCAGAG TTACACCTTT    1200

TTGTGTATTA AGAGTGTTCA TCAATGCATG GTAGTCATCT TGAATTTTTT CTTTTGATTG    1260

AGGCTGACGT AAACCAGCAG CTATTTGTGT GGCAGTATTA CCACCAGCTC CCATTGACAC    1320

CAGGGATAGA ACAGTTTGTA CAGACAATGG GGACATGATG AGATTGTCTT TGTTGCCAGA    1380

AGCAACCGTA TTGTACAGGC TTCCAGCAAA CTGGTTAATA CTTGTAGACA ATTCCTGGGG    1440

ATCCGCCATT GTTGAAATTG GTATTAACAC TGATACAAAA AGAAACACAA GTCGTGCGTG    1500

TTGAACTATC GCGTCAAACT GAGGACGCGG CATCAAAACT CTAGATATTA GAATCGTTTG    1560

TGAGTCATAT TGTATAATAT AGAAATACTA GGAATGTTTG AATAACACAC TATATACATT    1620
```

```
CAAACATTTG GCTTCGCGGA ACAACACACA TGAATCTGTT TTATATTTCT GTCGTCCTTG      1680

GAATCACACA GTTTCCAAAA ATTAGCTTCA TTTTTATATT TGTGTTTAAT TTATTTTGAA      1740

CATGATGTCA TTTGAATGAT AGTTATTGAA TTGATTTGTA TGTATTTTTG GAGATACTGA      1800

TTTTAATATT CTAAATGCGT AATTTGACTT TGCACAAT                              1838

(2) INFORMATION FOR SEQ ID NO:16:

(i) SEQUENCE CHARACTERISTICS:
        (A) LENGTH:  1260 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:16:

ATGCCGCGTC CTCAGTTTGA CGCGATAGTT CAACACGCAC GACTTGTGTT TCTTTTTGTA       60

TCAGTGTTAA TACCAATTTC AACAATGGCG GATCCCCAGG AATTGTCTAC AAGTATTAAC      120

CAGTTTGCTG GAAGCCTGTA CAATACGGTT GCTTCTGGCA ACAAAGACAA TCTCATCATG      180

TCCCCATTGT CTGTACAAAC TGTTCTATCC CTGGTGTCAA TGGGAGCTGG TGGTAATACT      240

GCCACACAAA TAGCTGCTGG TTTACGTCAG CCTCAATCAA AAGAAAAAAT TCAAGATGAC      300

TACCATGCAT TGATGAACAC TCTTAATACA CAAAAAGGTG TAACTCTGGA AATTGCCAAC      360

AAAGTTTACG TTATGGAAGG CTATACATTG AAACCCACCT TCAAAGAAGT TGCCACCAAC      420

AAATTCTTAG CTGGAGCAGA AAACTTGAAC TTTGCCCAAA ATGCTGAAAG CGCTAAAGTT      480

ATCAACACTT GGGTTGAAGA AAAAACTCAT GACAAAATTC ATGATTTGAT CAAAGCCGGT      540

GATCTAGACC AGGATTCAAG AATGGTTCTT GTCAATGCAT TGTACTTCAA GGGTCTTTGG      600

GAGAAACAAT TCAAGAAGGA AAACACTCAA GACAAACCTT TCTATGTTAC TGAAACAGAG      660

ACAAAGAATG TACGAATGAT GCACATTAAG GATAAATTCC GTTATGGAGA ATTTGAAGAA      720

TTAGATGCCA AGGCTGTAGA ATTGCCCTAC AGGAACTCAG ATTTGGCCAT GTTAATCATT      780

TTGCCAAACA GCAAAACTGG TCTCCCCGCT CTTGAAGAAA AATTACAAAA TGTTGACTTG      840

CAAAACTTGA CTCAACGCAT GTACTCTGTT GAAGTTATTT TGGATCTGCC TAAATTCAAG      900

ATTGAATCTG AAATTAATTT GAATGATCCT CTGAAAAAGT TGGGTATGTC TGATATGTTT      960

GTTCCTGGAA AAGCTGATTT CAAAGGATTG CTTGAAGGAT CTGATGAGAT GTTATATATT     1020

TCTAAAGTAA TTCAAAAAGC TTTCATTGAA GTAAATGAAG AAGGTGCTGA AGCTGCAGCT     1080

GCCACAGCGG TGCTTTTAGT AACGGAATCT TATGTACCTG AGGAAGTATT CGAAGCTAAT     1140

CATCCCTTTT ATTTTGCACT CTATAAATCT GCACAAAATC CAGTAGAATC TGAAAATGAA     1200

AGCTCTGAAA ATGAAAACCC TGAAAATGTT GAAGTACTAT TCTCTGGGAG ATTTACCAAT     1260

(2) INFORMATION FOR SEQ ID NO:17:

(i) SEQUENCE CHARACTERISTICS:
        (A) LENGTH:  1260 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:17:

ATTGGTAAAT CTCCCAGAGA ATAGTACTTC AACATTTTCA GGGTTTTCAT TTTCAGAGCT       60

TTCATTTTCA GATTCTACTG GATTTTGTGC AGATTTATAG AGTGCAAAAT AAAAGGGATG      120
```

-continued

```
ATTAGCTTCG AATACTTCCT CAGGTACATA AGATTCCGTT ACTAAAAGCA CCGCTGTGGC    180

AGCTGCAGCT TCAGCACCTT CTTCATTTAC TTCAATGAAA GCTTTTTGAA TTACTTTAGA    240

AATATATAAC ATCTCATCAG ATCCTTCAAG CAATCCTTTG AAATCAGCTT TTCCAGGAAC    300

AAACATATCA GACATACCCA ACTTTTTCAG AGGATCATTC AAATTAATTT CAGATTCAAT    360

CTTGAATTTA GGCAGATCCA AATAACTTC AACAGAGTAC ATGCGTTGAG TCAAGTTTTG     420

CAAGTCAACA TTTTGTAATT TTTCTTCAAG AGCGGGGAGA CCAGTTTTGC TGTTTGGCAA    480

AATGATTAAC ATGGCCAAAT CTGAGTTCCT GTAGGGCAAT TCTACAGCCT TGGCATCTAA    540

TTCTTCAAAT TCTCCATAAC GGAATTTATC CTTAATGTGC ATCATTCGTA CATTCTTTGT    600

CTCTGTTTCA GTAACATAGA AAGGTTTGTC TTGAGTGTTT TCCTTCTTGA ATTGTTTCTC    660

CCAAAGACCC TTGAAGTACA ATGCATTGAC AAGAACCATT CTTGAATCCT GGTCTAGATC    720

ACCGGCTTTG ATCAAATCAT GAATTTTGTC ATGAGTTTTT TCTTCAACCC AAGTGTTGAT    780

AACTTTAGCG CTTTCAGCAT TTTGGGCAAA GTTCAAGTTT CTGCTCCAG CTAAGAATTT     840

GTTGGTGGCA ACTTCTTTGA AGGTGGGTTT CAATGTATAG CCTTCCATAA CGTAAACTTT    900

GTTGGCAATT TCCAGAGTTA CACCTTTTTG TGTATTAAGA GTGTTCATCA ATGCATGGTA    960

GTCATCTTGA ATTTTTTCTT TTGATTGAGG CTGACGTAAA CCAGCAGCTA TTTGTGTGGC   1020

AGTATTACCA CCAGCTCCCA TTGACACCAG GGATAGAACA GTTTGTACAG ACAATGGGGA   1080

CATGATGAGA TTGTCTTTGT TGCCAGAAGC AACCGTATTG TACAGGCTTC AGCAAACTG    1140

GTTAATACTT GTAGACAATT CCTGGGGATC CGCCATTGTT GAAATTGGTA TTAACACTGA   1200

TACAAAAAGA AACACAAGTC GTGCGTGTTG AACTATCGCG TCAAACTGAG GACGCGGCAT   1260
```

(2) INFORMATION FOR SEQ ID NO:18:

(i) SEQUENCE CHARACTERISTICS:
        (A) LENGTH: 390 amino acids
        (B) TYPE: amino acid
        (D) TOPOLOGY: linear (ii) MOLECULE TYPE: protein (xi) SEQUENCE DESCRIPTION: SEQ ID NO:18:

```
Asp Pro Gln Glu Leu Ser Thr Ser Ile Asn Gln Phe Ala Gly Ser Leu
 1               5                  10                  15

Tyr Asn Thr Val Ala Ser Gly Asn Lys Asp Asn Leu Ile Met Ser Pro
            20                  25                  30

Leu Ser Val Gln Thr Val Leu Ser Leu Val Ser Met Gly Ala Gly Gly
        35                  40                  45

Asn Thr Ala Thr Gln Ile Ala Ala Gly Leu Arg Gln Pro Gln Ser Lys
    50                  55                  60

Glu Lys Ile Gln Asp Asp Tyr His Ala Leu Met Asn Thr Leu Asn Thr
65                  70                  75                  80

Gln Lys Gly Val Thr Leu Glu Ile Ala Asn Lys Val Tyr Val Met Glu
            85                  90                  95

Gly Tyr Thr Leu Lys Pro Thr Phe Lys Glu Val Ala Thr Asn Lys Phe
           100                 105                 110

Leu Ala Gly Ala Glu Asn Leu Asn Phe Ala Gln Asn Ala Glu Ser Ala
        115                 120                 125

Lys Val Ile Asn Thr Trp Val Glu Glu Lys Thr His Asp Lys Ile His
    130                 135                 140

Asp Leu Ile Lys Ala Gly Asp Leu Asp Gln Asp Ser Arg Met Val Leu
```

```
                145                 150                 155                 160
Val Asn Ala Leu Tyr Phe Lys Gly Leu Trp Glu Lys Gln Phe Lys Lys
                    165                 170                 175
Glu Asn Thr Gln Asp Lys Pro Phe Tyr Val Thr Glu Thr Glu Thr Lys
                180                 185                 190
Asn Val Arg Met Met His Ile Lys Asp Lys Phe Arg Tyr Gly Glu Phe
            195                 200                 205
Glu Glu Leu Asp Ala Lys Ala Val Glu Leu Pro Tyr Arg Asn Ser Asp
        210                 215                 220
Leu Ala Met Leu Ile Ile Leu Pro Asn Ser Lys Thr Gly Leu Pro Ala
225                 230                 235                 240
Leu Glu Glu Lys Leu Gln Asn Val Asp Leu Gln Asn Leu Thr Gln Arg
                245                 250                 255
Met Tyr Ser Val Glu Val Ile Leu Asp Leu Pro Lys Phe Lys Ile Glu
                260                 265                 270
Ser Glu Ile Asn Leu Asn Asp Pro Leu Lys Lys Leu Gly Met Ser Asp
            275                 280                 285
Met Phe Val Pro Gly Lys Ala Asp Phe Lys Gly Leu Leu Glu Gly Ser
        290                 295                 300
Asp Glu Met Leu Tyr Ile Ser Lys Val Ile Gln Lys Ala Phe Ile Glu
305                 310                 315                 320
Val Asn Glu Glu Gly Ala Glu Ala Ala Ala Thr Ala Val Leu Leu
                325                 330                 335
Val Thr Glu Ser Tyr Val Pro Glu Glu Val Phe Glu Ala Asn His Pro
                340                 345                 350
Phe Tyr Phe Ala Leu Tyr Lys Ser Ala Gln Asn Pro Val Glu Ser Glu
                355                 360                 365
Asn Glu Ser Ser Glu Asn Glu Asn Pro Glu Asn Val Glu Val Leu Phe
            370                 375                 380
Ser Gly Arg Phe Thr Asn
385                 390

(2) INFORMATION FOR SEQ ID NO:19:

(i) SEQUENCE CHARACTERISTICS:
        (A) LENGTH: 1414 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..1180

(xi) SEQUENCE DESCRIPTION: SEQ ID NO:19:

A CGA CTT GTG TTT CTT TTT GTA TCA GTG TTA ATA CCA ATT TCA ACA          46
  Arg Leu Val Phe Leu Phe Val Ser Val Leu Ile Pro Ile Ser Thr
   1               5                  10                  15

ATG GCG GAT CCC CAG GAA TTG TCT ACA AGT ATT AAC CAG TTT GCT GGA        94
Met Ala Asp Pro Gln Glu Leu Ser Thr Ser Ile Asn Gln Phe Ala Gly
20                  25                  30

AGC CTG TAC AAT ACG GTT GCT TCT GGC AAC AAA GAC AAT CTC ATC ATG       142
Ser Leu Tyr Asn Thr Val Ala Ser Gly Asn Lys Asp Asn Leu Ile Met
35                  40                  45

TCC CCA TTG TCT GTA CAA ACT GTT CTA TCC CTG GTG TCA ATG GGA GCT       190
Ser Pro Leu Ser Val Gln Thr Val Leu Ser Leu Val Ser Met Gly Ala
50                  55                  60
```

```
GGT GGT AAT ACT GCC ACA CAA ATA GCT GCT GGT TTA CGT CAG CCT CAA    238
Gly Gly Asn Thr Ala Thr Gln Ile Ala Ala Gly Leu Arg Gln Pro Gln
 65                  70                  75

TCA AAA GAA AAA ATT CAA GAT GAC TAC CAT GCA TTG ATG AAC ACT CTT    286
Ser Lys Glu Lys Ile Gln Asp Asp Tyr His Ala Leu Met Asn Thr Leu
 80                  85                  90                  95

AAT ACA CAA AAA GGT GTA ACT CTG GAA ATT GCC AAC AAA GTT TAC GTT    334
Asn Thr Gln Lys Gly Val Thr Leu Glu Ile Ala Asn Lys Val Tyr Val
100                 105                 110

ATG GAA GGC TAT ACA TTG AAA CCC ACC TTC AAA GAA GTT GCC ACC AAC    382
Met Glu Gly Tyr Thr Leu Lys Pro Thr Phe Lys Glu Val Ala Thr Asn
115                 120                 125

AAA TTC TTA GCT GGA GCA GAA AAC TTG AAC TTT GCC CAA AAT GCT GAA    430
Lys Phe Leu Ala Gly Ala Glu Asn Leu Asn Phe Ala Gln Asn Ala Glu
130                 135                 140

AGC GCT AAA GTT ATC AAC ACT TGG GTT GAA GAA AAA ACT CAT GAC AAA    478
Ser Ala Lys Val Ile Asn Thr Trp Val Glu Glu Lys Thr His Asp Lys
145                 150                 155

ATT CAT GAT TTG ATC AAA GCC GGT GAT CTA GAC CAG GAT TCA AGA ATG    526
Ile His Asp Leu Ile Lys Ala Gly Asp Leu Asp Gln Asp Ser Arg Met
160                 165                 170                 175

GTT CTT GTC AAT GCA TTG TAC TTC AAG GGT CTT TGG GAG AAA CAA TTC    574
Val Leu Val Asn Ala Leu Tyr Phe Lys Gly Leu Trp Glu Lys Gln Phe
180                 185                 190

AAG AAG GAA AAC ACT CAA GAC AAA CCT TTC TAT GTT ACT GAA ACA GAG    622
Lys Lys Glu Asn Thr Gln Asp Lys Pro Phe Tyr Val Thr Glu Thr Glu
195                 200                 205

ACA AAG AAT GTA CGA ATG ATG CAC ATT AAG GAT AAA TTC CGT TAT GGA    670
Thr Lys Asn Val Arg Met Met His Ile Lys Asp Lys Phe Arg Tyr Gly
210                 215                 220

GAA TTT GAA GAA TTA GAT GCC AAG GCT GTA GAA TTG CCC TAC AGG AAC    718
Glu Phe Glu Glu Leu Asp Ala Lys Ala Val Glu Leu Pro Tyr Arg Asn
225                 230                 235

TCA GAT TTG GCC ATG TTA ATC ATT TTG CCA AAC AGC AAA ACT GGT CTC    766
Ser Asp Leu Ala Met Leu Ile Ile Leu Pro Asn Ser Lys Thr Gly Leu
240                 245                 250                 255

CCC GCT CTT GAA GAA AAA TTA CAA AAT GTT GAC TTG CAA AAC TTG ACT    814
Pro Ala Leu Glu Glu Lys Leu Gln Asn Val Asp Leu Gln Asn Leu Thr
260                 265                 270

CAA CGC ATG TAC TCT GTT GAA GTT ATT TTG GAT CTG CCT AAA TTC AAG    862
Gln Arg Met Tyr Ser Val Glu Val Ile Leu Asp Leu Pro Lys Phe Lys
275                 280                 285

ATT GAA TCT GAA ATT AAT TTG AAT GAT CCT CTG AAA AAG TTG GGT ATG    910
Ile Glu Ser Glu Ile Asn Leu Asn Asp Pro Leu Lys Lys Leu Gly Met
290                 295                 300

TCT GAT ATG TTT GTT CCT GGA AAA GCT GAT TTC AAA GGA TTG CTT GAA    958
Ser Asp Met Phe Val Pro Gly Lys Ala Asp Phe Lys Gly Leu Leu Glu
305                 310                 315

GGA TCT GAT GAG ATG TTA TAT ATT TCT AAA GTA ATT CAA AAA GCT TTC   1006
Gly Ser Asp Glu Met Leu Tyr Ile Ser Lys Val Ile Gln Lys Ala Phe
320                 325                 330                 335

ATT GAA GTA AAT GAA GAA GGT GCT GAA GCT GCA GCT GCC ACA GGC GTG   1054
Ile Glu Val Asn Glu Glu Gly Ala Glu Ala Ala Ala Ala Thr Gly Val
340                 345                 350

ATG TTA ATG ATG CGT TGT ATG CCA ATG ATG CCA ATG GCC TTC AAT GCT   1102
Met Leu Met Met Arg Cys Met Pro Met Met Pro Met Ala Phe Asn Ala
355                 360                 365

GAG CAT CCA TTC CTG TAC TTC TTA CAC AGC AAA AAT TCT GTT CTA TTC   1150
Glu His Pro Phe Leu Tyr Phe Leu His Ser Lys Asn Ser Val Leu Phe
```

```
                   370                375               380
AAT GGT CGT CTT GTT AAA CCA ACA ACT GAA TAA AAGCCAAATG CACTTCACTA    1203
Asn Gly Arg Leu Val Lys Pro Thr Thr Glu
385                 390

ATATTTTTTA ATTGCTTACT GAAACAGTGC CTGTAGAACA TTGTGTTCAA TTTATATTTG    1263

TCAGCTTTAA GTATTCAGTA TTTTTTATCA TCACTATTTC AGTGGTGGAT CTTAAGTACA    1323

AATTTATTGT TATGATATAT ATTTATTTTT TGTGAATATT TTTTAACAA ATTTTGATAA     1383

AAAACATAAG ACTAAAAAAA AAAAAAAAA A                                    1414

(2) INFORMATION FOR SEQ ID NO:20:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:20:

Arg Leu Val Phe Leu Phe Val Ser Val Leu Ile Pro Ile Ser Thr Met
 1               5                  10                  15

Ala Asp Pro Gln Glu Leu Ser Thr Ser Ile Asn Gln Phe Ala Gly Ser
                20                  25                  30

Leu Tyr Asn Thr Val Ala Ser Gly Asn Lys Asp Asn Leu Ile Met Ser
            35                  40                  45

Pro Leu Ser Val Gln Thr Val Leu Ser Leu Val Ser Met Gly Ala Gly
        50                  55                  60

Gly Asn Thr Ala Thr Gln Ile Ala Ala Gly Leu Arg Gln Pro Gln Ser
65                  70                  75                  80

Lys Glu Lys Ile Gln Asp Asp Tyr His Ala Leu Met Asn Thr Leu Asn
                85                  90                  95

Thr Gln Lys Gly Val Thr Leu Glu Ile Ala Asn Lys Val Tyr Val Met
            100                 105                 110

Glu Gly Tyr Thr Leu Lys Pro Thr Phe Lys Glu Val Ala Thr Asn Lys
        115                 120                 125

Phe Leu Ala Gly Ala Glu Asn Leu Asn Phe Ala Gln Asn Ala Glu Ser
130                 135                 140

Ala Lys Val Ile Asn Thr Trp Val Glu Glu Lys Thr His Asp Lys Ile
145                 150                 155                 160

His Asp Leu Ile Lys Ala Gly Asp Leu Asp Gln Asp Ser Arg Met Val
                165                 170                 175

Leu Val Asn Ala Leu Tyr Phe Lys Gly Leu Trp Glu Lys Gln Phe Lys
            180                 185                 190

Lys Glu Asn Thr Gln Asp Lys Pro Phe Tyr Val Thr Glu Thr Glu Thr
        195                 200                 205

Lys Asn Val Arg Met Met His Ile Lys Asp Lys Phe Arg Tyr Gly Glu
    210                 215                 220

Phe Glu Glu Leu Asp Ala Lys Ala Val Glu Leu Pro Tyr Arg Asn Ser
225                 230                 235                 240

Asp Leu Ala Met Leu Ile Ile Leu Pro Asn Ser Lys Thr Gly Leu Pro
                245                 250                 255

Ala Leu Glu Glu Lys Leu Gln Asn Val Asp Leu Gln Asn Leu Thr Gln
            260                 265                 270

Arg Met Tyr Ser Val Glu Val Ile Leu Asp Leu Pro Lys Phe Lys Ile
        275                 280                 285
```

Glu Ser Glu Ile Asn Leu Asn Asp Pro Leu Lys Lys Leu Gly Met Ser
290                 295                 300

Asp Met Phe Val Pro Gly Lys Ala Asp Phe Lys Gly Leu Leu Glu Gly
305                 310                 315                 320

Ser Asp Glu Met Leu Tyr Ile Ser Lys Val Ile Gln Lys Ala Phe Ile
                325                 330                 335

Glu Val Asn Glu Glu Gly Ala Glu Ala Ala Ala Thr Gly Val Met
                340                 345                 350

Leu Met Met Arg Cys Met Pro Met Met Pro Met Ala Phe Asn Ala Glu
            355                 360                 365

His Pro Phe Leu Tyr Phe Leu His Ser Lys Asn Ser Val Leu Phe Asn
        370                 375                 380

Gly Arg Leu Val Lys Pro Thr Thr Glu
385                 390

(2) INFORMATION FOR SEQ ID NO:21:

(i) SEQUENCE CHARACTERISTICS:
        (A) LENGTH: 1414 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TTTTTTTTTT TTTTTTTTAG TCTTATGTTT TTTATCAAAA TTTGTTAAAA AAATATTCAC      60

AAAAAATAAA TATATATCAT AACAATAAAT TTGTACTTAA GATCCACCAC TGAAATAGTG     120

ATGATAAAAA ATACTGAATA CTTAAAGCTG ACAAATATAA ATTGAACACA ATGTTCTACA     180

GGCACTGTTT CAGTAAGCAA TTAAAAAATA TTAGTGAAGT GCATTTGGCT TTTATTCAGT     240

TGTTGGTTTA ACAAGACGAC CATTGAATAG AACAGAATTT TTGCTGTGTA AGAAGTACAG     300

GAATGGATGC TCAGCATTGA AGGCCATTGG CATCATTGGC ATACAACGCA TCATTAACAT     360

CACGCCTGTG GCAGCTGCAG CTTCAGCACC TTCTTCATTT ACTTCAATGA AAGCTTTTTG     420

AATTACTTTA GAAATATATA ACATCTCATC AGATCCTTCA AGCAATCCTT TGAAATCAGC     480

TTTTCCAGGA ACAAACATAT CAGACATACC CAACTTTTTC AGAGGATCAT TCAAATTAAT     540

TTCAGATTCA ATCTTGAATT TAGGCAGATC CAAAATAACT TCAACAGAGT ACATGCGTTG     600

AGTCAAGTTT TGCAAGTCAA CATTTTGTAA TTTTTCTTCA AGAGCGGGGA GACCAGTTTT     660

GCTGTTTGGC AAAATGATTA ACATGGCCAA ATCTGAGTTC CTGTAGGGCA ATTCTACAGC     720

CTTGGCATCT AATTCTTCAA ATTCTCCATA ACGGAATTTA TCCTTAATGT GCATCATTCG     780

TACATTCTTT GTCTCTGTTT CAGTAACATA GAAAGGTTTG TCTTGAGTGT TTTCCTTCTT     840

GAATTGTTTC TCCCAAAGAC CCTTGAAGTA CAATGCATTG ACAAGAACCA TTCTTGAATC     900

CTGGTCTAGA TCACCGGCTT TGATCAAATC ATGAATTTTG TCATGAGTTT TTCTTCAAC     960

CCAAGTGTTG ATAACTTTAG CGCTTTCAGC ATTTTGGGCA AAGTTCAAGT TTTCTGCTCC    1020

AGCTAAGAAT TTGTTGGTGG CAACTTCTTT GAAGGTGGGT TTCAATGTAT AGCCTTCCAT    1080

AACGTAAACT TTGTTGGCAA TTTCCAGAGT TACACCTTTT TGTGTATTAA GAGTGTTCAT    1140

CAATGCATGG TAGTCATCTT GAATTTTTTC TTTTGATTGA GGCTGACGTA AACCAGCAGC    1200

TATTTGTGTG GCAGTATTAC CACCAGCTCC CATTGACACC AGGGATAGAA CAGTTTGTAC    1260

AGACAATGGG GACATGATGA GATTGTCTTT GTTGCCAGAA GCAACCGTAT TGTACAGGCT    1320

```
TCCAGCAAAC TGGTTAATAC TTGTAGACAA TTCCTGGGGA TCCGCCATTG TTGAAATTGG    1380

TATTAACACT GATACAAAAA GAAACACAAG TCGT                                1414

(2) INFORMATION FOR SEQ ID NO:22:

(i) SEQUENCE CHARACTERISTICS:
        (A) LENGTH: 1179 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CGACTTGTGT TTCTTTTTGT ATCAGTGTTA ATACCAATTT CAACAATGGC GGATCCCCAG      60

GAATTGTCTA CAAGTATTAA CCAGTTTGCT GGAAGCCTGT ACAATACGGT TGCTTCTGGC     120

AACAAAGACA ATCTCATCAT GTCCCCATTG TCTGTACAAA CTGTTCTATC CCTGGTGTCA     180

ATGGGAGCTG GTGGTAATAC TGCCACACAA ATAGCTGCTG GTTTACGTCA GCCTCAATCA     240

AAAGAAAAAA TTCAAGATGA CTACCATGCA TTGATGAACA CTCTTAATAC ACAAAAAGGT     300

GTAACTCTGG AAATTGCCAA CAAAGTTTAC GTTATGGAAG CTATACATT GAAACCCACC      360

TTCAAAGAAG TTGCCACCAA CAAATTCTTA GCTGGAGCGA AAAACTTGAA CTTTGCCCAA     420

AATGCTGAAA GCGCTAAAGT TATCAACACT TGGGTTGAAG AAAAAACTCA TGACAAAATT     480

CATGATTTGA TCAAAGCCGG TGATCTAGAC CAGGATTCAA GAATGGTTCT TGTCAATGCA     540

TTGTACTTCA AGGGTCTTTG GGAGAAACAA TTCAAGAAGG AAAACACTCA AGACAAACCT     600

TTCTATGTTA CTGAAACAGA GACAAAGAAT GTACGAATGA TGCACATTAA GGATAAATTC     660

CGTTATGGAG AATTTGAAGA ATTAGATGCC AAGGCTGTAG AATTGCCCTA CAGGAACTCA     720

GATTTGGCCA TGTTAATCAT TTTGCCAAAC AGCAAAACTG GTCTCCCCGC TCTTGAAGAA     780

AAATTACAAA ATGTTGACTT GCAAAACTTG ACTCAACGCA TGTACTCTGT TGAAGTTATT     840

TTGGATCTGC CTAAATTCAA GATTGAATCT GAAATTAATT TGAATGATCC TCTGAAAAAG     900

TTGGGTATGT CTGATATGTT TGTTCCTGGA AAAGCTGATT TCAAAGGATT GCTTGAAGGA     960

TCTGATGAGA TGTTATATAT TTCTAAAGTA ATTCAAAAAG CTTTCATTGA AGTAAATGAA    1020

GAAGGTGCTG AAGCTGCAGC TGCCACAGGC GTGATGTTAA TGATGCGTTG TATGCCAATG    1080

ATGCCAATGG CCTTCAATGC TGAGCATCCA TTCCTGTACT TCTTACACAG CAAAAATTCT    1140

GTTCTATTCA ATGGTCGTCT TGTTAAACCA ACAACTGAA                           1179

(2) INFORMATION FOR SEQ ID NO:23:

(i) SEQUENCE CHARACTERISTICS:
        (A) LENGTH: 1179 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

TTCAGTTGTT GGTTAACAA GACGACCATT GAATAGAACA GAATTTTTGC TGTGTAAGAA       60

GTACAGGAAT GGATGCTCAG CATTGAAGGC CATTGGCATC ATTGGCATAC AACGCATCAT     120

TAACATCACG CCTGTGGCAG CTGCAGCTTC AGCACCTTCT TCATTTACTT CAATGAAAGC     180

TTTTTGAATT ACTTTAGAAA TATATAACAT CTCATCAGAT CCTTCAAGCA ATCCTTTGAA     240

ATCAGCTTTT CCAGGAACAA ACATATCAGA CATACCCAAC TTTTTCAGAG GATCATTCAA     300
```

```
ATTAATTTCA GATTCAATCT TGAATTTAGG CAGATCCAAA ATAACTTCAA CAGAGTACAT    360
GCGTTGAGTC AAGTTTTGCA AGTCAACATT TTGTAATTTT TCTTCAAGAG CGGGGAGACC    420
AGTTTTGCTG TTTGGCAAAA TGATTAACAT GGCCAAATCT GAGTTCCTGT AGGGCAATTC    480
TACAGCCTTG GCATCTAATT CTTCAAATTC TCCATAACGG AATTTATCCT TAATGTGCAT    540
CATTCGTACA TTCTTTGTCT CTGTTTCAGT AACATAGAAA GGTTTGTCTT GAGTGTTTTC    600
CTTCTTGAAT TGTTTCTCCC AAAGACCCTT GAAGTACAAT GCATTGACAA GAACCATTCT    660
TGAATCCTGG TCTAGATCAC CGGCTTTGAT CAAATCATGA ATTTTGTCAT GAGTTTTTTC    720
TTCAACCCAA GTGTTGATAA CTTTAGCGCT TCAGCATTT TGGGCAAAGT TCAAGTTTTC     780
TGCTCCAGCT AAGAATTTGT TGGTGGCAAC TTCTTTGAAG GTGGGTTTCA ATGTATAGCC    840
TTCCATAACG TAAACTTTGT TGGCAATTTC CAGAGTTACA CCTTTTTGTG TATTAAGAGT    900
GTTCATCAAT GCATGGTAGT CATCTTGAAT TTTTTCTTTT GATTGAGGCT GACGTAAACC    960
AGCAGCTATT TGTGTGGCAG TATTACCACC AGCTCCCATT GACACCAGGG ATAGAACAGT   1020
TTGTACAGAC AATGGGGACA TGATGAGATT GTCTTTGTTG CCAGAAGCAA CCGTATTGTA   1080
CAGGCTTCCA GCAAACTGGT TAATACTTGT AGACAATTCC TGGGGATCCG CCATTGTTGA   1140
AATTGGTATT AACACTGATA CAAAAAGAAA CACAAGTCG                          1179
```

(2) INFORMATION FOR SEQ ID NO:24:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:24:

```
Asp Pro Gln Glu Leu Ser Thr Ser Ile Asn Gln Phe Ala Gly Ser Leu
 1               5                  10                  15

Tyr Asn Thr Val Ala Ser Gly Asn Lys Asp Asn Leu Ile Met Ser Pro
             20                  25                  30

Leu Ser Val Gln Thr Val Leu Ser Leu Val Ser Met Gly Ala Gly Gly
         35                  40                  45

Asn Thr Ala Thr Gln Ile Ala Ala Gly Leu Arg Gln Pro Gln Ser Lys
     50                  55                  60

Glu Lys Ile Gln Asp Asp Tyr His Ala Leu Met Asn Thr Leu Asn Thr
65                  70                  75                  80

Gln Lys Gly Val Thr Leu Glu Ile Ala Asn Lys Val Tyr Val Met Glu
                 85                  90                  95

Gly Tyr Thr Leu Lys Pro Thr Phe Lys Glu Val Ala Thr Asn Lys Phe
            100                 105                 110

Leu Ala Gly Ala Glu Asn Leu Asn Phe Ala Gln Asn Ala Glu Ser Ala
        115                 120                 125

Lys Val Ile Asn Thr Trp Val Glu Glu Lys Thr His Asp Lys Ile His
    130                 135                 140

Asp Leu Ile Lys Ala Gly Asp Leu Asp Gln Asp Ser Arg Met Val Leu
145                 150                 155                 160

Val Asn Ala Leu Tyr Phe Lys Gly Leu Trp Glu Lys Gln Phe Lys Lys
                165                 170                 175

Glu Asn Thr Gln Asp Lys Pro Phe Tyr Val Thr Glu Thr Glu Thr Lys
            180                 185                 190
```

```
Asn Val Arg Met Met His Ile Lys Asp Lys Phe Arg Tyr Gly Glu Phe
        195                 200                 205

Glu Glu Leu Asp Ala Lys Ala Val Glu Leu Pro Tyr Arg Asn Ser Asp
        210                 215                 220

Leu Ala Met Leu Ile Ile Leu Pro Asn Ser Lys Thr Gly Leu Pro Ala
225                 230                 235                 240

Leu Glu Glu Lys Leu Gln Asn Val Asp Leu Gln Asn Leu Thr Gln Arg
                245                 250                 255

Met Tyr Ser Val Glu Val Ile Leu Asp Leu Pro Lys Phe Lys Ile Glu
                260                 265                 270

Ser Glu Ile Asn Leu Asn Asp Pro Leu Lys Lys Leu Gly Met Ser Asp
            275                 280                 285

Met Phe Val Pro Gly Lys Ala Asp Phe Lys Gly Leu Leu Glu Gly Ser
        290                 295                 300

Asp Glu Met Leu Tyr Ile Ser Lys Val Ile Gln Lys Ala Phe Ile Glu
305                 310                 315                 320

Val Asn Glu Glu Gly Ala Glu Ala Ala Ala Thr Gly Val Met Leu
                325                 330                 335

Met Met Arg Cys Met Pro Met Met Pro Met Ala Phe Asn Ala Glu His
                340                 345                 350

Pro Phe Leu Tyr Phe Leu His Ser Lys Asn Ser Val Leu Phe Asn Gly
            355                 360                 365

Arg Leu Val Lys Pro Thr Thr Glu
        370                 375

(2) INFORMATION FOR SEQ ID NO:25:

(i) SEQUENCE CHARACTERISTICS:
        (A) LENGTH:  1492 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  3..1196

(xi) SEQUENCE DESCRIPTION:  SEQ ID NO:25:

CG ATA GTT CAA CAC GCA CGA CTT GTG TTT CTT TTT GTA TCA GTG TTA      47
   Ile Val Gln His Ala Arg Leu Val Phe Leu Phe Val Ser Val Leu
    1               5                  10                  15

ATA CCA ATT TCA ACA ATG GCG GAT CCC CAG GAA TTG TCT ACA AGT ATT     95
Ile Pro Ile Ser Thr Met Ala Asp Pro Gln Glu Leu Ser Thr Ser Ile
                20                  25                  30

AAC CAG TTT GCT GGA AGC CTG TAC AAT ACG GTT GCT TCT GGC AAC AAA    143
Asn Gln Phe Ala Gly Ser Leu Tyr Asn Thr Val Ala Ser Gly Asn Lys
            35                  40                  45

GAC AAT CTC ATC ATG TCC CCA TTG TCT GTA CAA ACT GTT CTA TCC CTG    191
Asp Asn Leu Ile Met Ser Pro Leu Ser Val Gln Thr Val Leu Ser Leu
        50                  55                  60

GTG TCA ATG GGA GCT GGT GGT AAT ACT GCC ACA CAA ATA GCT GCT GGT    239
Val Ser Met Gly Ala Gly Gly Asn Thr Ala Thr Gln Ile Ala Ala Gly
65                  70                  75

TTA CGT CAG CCT CAA TCA AAA GAA AAA ATT CAA GAT GAC TAC CAC GCA    287
Leu Arg Gln Pro Gln Ser Lys Glu Lys Ile Gln Asp Asp Tyr His Ala
80                  85                  90                  95

TTG ATG AAC ACT CTT AAT ACA CAA AAA GGT GTA ACT CTG GAA ATT GCC    335
Leu Met Asn Thr Leu Asn Thr Gln Lys Gly Val Thr Leu Glu Ile Ala
```

```
                    100              105                110
AAT AAA GTT TAT GTT ATG GAA GGC TAT ACA TTA AAA CCC ACC TTC AAA     383
Asn Lys Val Tyr Val Met Glu Gly Tyr Thr Leu Lys Pro Thr Phe Lys
            115             120             125

GAA GTT GCC ACC AAC AAA TTC TTA GCT GGA GCA GAA AAC TTG AAC TTT     431
Glu Val Ala Thr Asn Lys Phe Leu Ala Gly Ala Glu Asn Leu Asn Phe
            130             135             140

GCC CAA AAT GCT GAA AGC GCT AAA GTT ATC AAC ACT TGG GTT GAA GAA     479
Ala Gln Asn Ala Glu Ser Ala Lys Val Ile Asn Thr Trp Val Glu Glu
145             150             155

AAA ACT CAT GAC AAA ATT CAT GAT TTG ATC AAA GCC GGT GAT CTA GAC     527
Lys Thr His Asp Lys Ile His Asp Leu Ile Lys Ala Gly Asp Leu Asp
160             165             170             175

CAG GAT TCA AGA ATG GTT CTT GTC AAT GCA TTG TAC TTC AAG GGT CTT     575
Gln Asp Ser Arg Met Val Leu Val Asn Ala Leu Tyr Phe Lys Gly Leu
            180             185             190

TGG GAG AAA CAA TTC AAG AAG GAA AAC ACC CAA GAC AAA CCT TTC TAT     623
Trp Glu Lys Gln Phe Lys Lys Glu Asn Thr Gln Asp Lys Pro Phe Tyr
            195             200             205

GTT ACT GAA ACA GAG ACA AAG AAT GTA CGA ATG ATG CAC ATT AAG GAT     671
Val Thr Glu Thr Glu Thr Lys Asn Val Arg Met Met His Ile Lys Asp
            210             215             220

AAA TTC CGT TAT GGA GAA TTT GAA GAA TTA GAT GCC AAG GCT GTA GAA     719
Lys Phe Arg Tyr Gly Glu Phe Glu Glu Leu Asp Ala Lys Ala Val Glu
        225             230             235

TTG CCC TAC AGG AAC TCA GAT TTG GCC ATG TTA ATC ATT TTG CCA AAC     767
Leu Pro Tyr Arg Asn Ser Asp Leu Ala Met Leu Ile Ile Leu Pro Asn
240             245             250             255

AGC AAA ACT GGT CTC CCC ACT CTT GAA GAA AAA TTA CAA AAT GTT GAT     815
Ser Lys Thr Gly Leu Pro Thr Leu Glu Glu Lys Leu Gln Asn Val Asp
            260             265             270

TTG CAA AAC TTG ACT CAA CGC ATG TAC TCT GTT GAA GTT ATT TTG GAT     863
Leu Gln Asn Leu Thr Gln Arg Met Tyr Ser Val Glu Val Ile Leu Asp
            275             280             285

CTG CCT AAA TTC AAA ATT GAG TCT GAA ATT AAT TTG AAT GAT CCT CTG     911
Leu Pro Lys Phe Lys Ile Glu Ser Glu Ile Asn Leu Asn Asp Pro Leu
        290             295             300

AAA AAG TTG GGT ATG TCT GAT ATG TTC ATG CCT GGA AAA GCT GAT TTC     959
Lys Lys Leu Gly Met Ser Asp Met Phe Met Pro Gly Lys Ala Asp Phe
305             310             315

AAA GGA TTG CTT GAA GGA TCT GAT GAG ATG TTA TAT ATT TCT AAA GTA    1007
Lys Gly Leu Leu Glu Gly Ser Asp Glu Met Leu Tyr Ile Ser Lys Val
320             325             330             335

ATT CAA AAA GCT TTC ATT GAA GTA AAT GAA GAA GGT GCT GAA GCT GCA    1055
Ile Gln Lys Ala Phe Ile Glu Val Asn Glu Glu Gly Ala Glu Ala Ala
            340             345             350

GCT GCC ACA GGC GTG ATG TTA ATG ATG CGT TGT ATG CCA ATG ATG CCA    1103
Ala Ala Thr Gly Val Met Leu Met Met Arg Cys Met Pro Met Met Pro
            355             360             365

ATG GCC TTC AAT GCT GAG CAT CCA TTC CTG TAC TTC TTA CAC AGC AAA    1151
Met Ala Phe Asn Ala Glu His Pro Phe Leu Tyr Phe Leu His Ser Lys
            370             375             380

AAT TCT GTT CTA TTC AAT GGT CGT CTT GTT AAA CCA ACA ACT GAA TAA    1199
Asn Ser Val Leu Phe Asn Gly Arg Leu Val Lys Pro Thr Thr Glu
        385             390             395

AAGCCAAATG CACTTCACTA ATATTTTTTA ATTGCTTACT GAAACAGTGC CTGTAGAACA   1259

TTGTGTTCAA TTTATATTTG TCAGCTTTAA GTATTCAGTA TTTTTTATCA TCACTATTTC   1319

AGTGGTGGAT CTTAAGTACA AATTTATTGT TATGATATAT ATTTATTTTT TGTGAATATT   1379
```

TTTTTAACAA ATTTTGATAA AAAACATAAG ACTAAAAATA AAAGAAAAAT TAAAATTTAT    1439

GTATAATTGT TGTATACTAA ATTATATCTT TAAGAAAAAA AAAAAAAAAA AAA           1492

(2) INFORMATION FOR SEQ ID NO:26:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO:26:

```
Ile Val Gln His Ala Arg Leu Val Phe Leu Phe Val Ser Val Leu Ile
 1               5                  10                  15

Pro Ile Ser Thr Met Ala Asp Pro Gln Glu Leu Ser Thr Ser Ile Asn
            20                  25                  30

Gln Phe Ala Gly Ser Leu Tyr Asn Thr Val Ala Ser Gly Asn Lys Asp
        35                  40                  45

Asn Leu Ile Met Ser Pro Leu Ser Val Gln Thr Val Leu Ser Leu Val
    50                  55                  60

Ser Met Gly Ala Gly Gly Asn Thr Ala Thr Gln Ile Ala Ala Gly Leu
65                  70                  75                  80

Arg Gln Pro Gln Ser Lys Glu Lys Ile Gln Asp Asp Tyr His Ala Leu
                85                  90                  95

Met Asn Thr Leu Asn Thr Gln Lys Gly Val Thr Leu Glu Ile Ala Asn
            100                 105                 110

Lys Val Tyr Val Met Glu Gly Tyr Thr Leu Lys Pro Thr Phe Lys Glu
        115                 120                 125

Val Ala Thr Asn Lys Phe Leu Ala Gly Ala Glu Asn Leu Asn Phe Ala
    130                 135                 140

Gln Asn Ala Glu Ser Ala Lys Val Ile Asn Thr Trp Val Glu Glu Lys
145                 150                 155                 160

Thr His Asp Lys Ile His Asp Leu Ile Lys Ala Gly Asp Leu Asp Gln
                165                 170                 175

Asp Ser Arg Met Val Leu Val Asn Ala Leu Tyr Phe Lys Gly Leu Trp
            180                 185                 190

Glu Lys Gln Phe Lys Lys Glu Asn Thr Gln Asp Lys Pro Phe Tyr Val
        195                 200                 205

Thr Glu Thr Glu Thr Lys Asn Val Arg Met Met His Ile Lys Asp Lys
    210                 215                 220

Phe Arg Tyr Gly Glu Phe Glu Glu Leu Asp Ala Lys Ala Val Glu Leu
225                 230                 235                 240

Pro Tyr Arg Asn Ser Asp Leu Ala Met Leu Ile Ile Leu Pro Asn Ser
                245                 250                 255

Lys Thr Gly Leu Pro Thr Leu Glu Glu Lys Leu Gln Asn Val Asp Leu
            260                 265                 270

Gln Asn Leu Thr Gln Arg Met Tyr Ser Val Glu Val Ile Leu Asp Leu
        275                 280                 285

Pro Lys Phe Lys Ile Glu Ser Glu Ile Asn Leu Asn Asp Pro Leu Lys
    290                 295                 300

Lys Leu Gly Met Ser Asp Met Phe Met Pro Gly Lys Ala Asp Phe Lys
305                 310                 315                 320

Gly Leu Leu Glu Gly Ser Asp Glu Met Leu Tyr Ile Ser Lys Val Ile
                325                 330                 335
```

```
Gln Lys Ala Phe Ile Glu Val Asn Glu Glu Gly Ala Glu Ala Ala Ala
            340                 345                 350

Ala Thr Gly Val Met Leu Met Met Arg Cys Met Pro Met Met Pro Met
        355                 360                 365

Ala Phe Asn Ala Glu His Pro Phe Leu Tyr Phe Leu His Ser Lys Asn
    370                 375                 380

Ser Val Leu Phe Asn Gly Arg Leu Val Lys Pro Thr Thr Glu
385                 390                 395
```

(2) INFORMATION FOR SEQ ID NO:27:

(i) SEQUENCE CHARACTERISTICS:
        (A) LENGTH: 1492 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
TTTTTTTTTT TTTTTTTTTC TTAAAGATAT AATTTAGTAT ACAACAATTA TACATAAATT      60

TTAATTTTTC TTTTATTTTT AGTCTTATGT TTTTTATCAA AATTTGTTAA AAAAATATTC     120

ACAAAAAATA AATATATATC ATAACAATAA ATTTGTACTT AAGATCCACC ACTGAAATAG     180

TGATGATAAA AAATACTGAA TACTTAAAGC TGACAAATAT AAATTGAACA CAATGTTCTA     240

CAGGCACTGT TTCAGTAAGC AATTAAAAAA TATTAGTGAA GTGCATTTGG CTTTTATTCA     300

GTTGTTGGTT TAACAAGACG ACCATTGAAT AGAACAGAAT TTTTGCTGTG TAAGAAGTAC     360

AGGAATGGAT GCTCAGCATT GAAGGCCATT GGCATCATTG GCATACAACG CATCATTAAC     420

ATCACGCCTG TGGCAGCTGC AGCTTCAGCA CCTTCTTCAT TTACTTCAAT GAAAGCTTTT     480

TGAATTACTT TAGAAATATA TAACATCTCA TCAGATCCTT CAAGCAATCC TTTGAAATCA     540

GCTTTTCCAG GCATGAACAT ATCAGACATA CCCAACTTTT TCAGAGGATC ATTCAAATTA     600

ATTTCAGACT CAATTTTGAA TTTAGGCAGA TCCAAAATAA CTTCAACAGA GTACATGCGT     660

TGAGTCAAGT TTTGCAAATC AACATTTTGT AATTTTTCTT CAAGAGTGGG GAGACCAGTT     720

TTGCTGTTTG GCAAAATGAT TAACATGGCC AAATCTGAGT TCCTGTAGGG CAATTCTACA     780

GCCTTGGCAT CTAATTCTTC AAATTCTCCA TAACGGAATT TATCCTTAAT GTGCATCATT     840

CGTACATTCT TTGTCTCTGT TTCAGTAACA TAGAAAGGTT TGTCTTGGGT GTTTTCCTTC     900

TTGAATTGTT TCTCCCAAAG ACCCTTGAAG TACAATGCAT TGACAAGAAC CATTCTTGAA     960

TCCTGGTCTA GATCACCGGC TTTGATCAAA TCATGAATTT TGTCATGAGT TTTTTCTTCA    1020

ACCCAAGTGT TGATAACTTT AGCGCTTTCA GCATTTTGGG CAAAGTTCAA GTTTTCTGCT    1080

CCAGCTAAGA ATTTGTTGGT GGCAACTTCT TTGAAGGTGG GTTTTAATGT ATAGCCTTCC    1140

ATAACATAAA CTTTATTGGC AATTTCCAGA GTTACACCTT TTTGTGTATT AAGAGTGTTC    1200

ATCAATGCGT GGTAGTCATC TTGAATTTTT TCTTTTGATT GAGGCTGACG TAAACCAGCA    1260

GCTATTTGTG TGGCAGTATT ACCACCAGCT CCCATTGACA CCAGGGATAG AACAGTTTGT    1320

ACAGACAATG GGGACATGAT GAGATTGTCT TTGTTGCCAG AAGCAACCGT ATTGTACAGG    1380

CTTCCAGCAA ACTGGTTAAT ACTTGTAGAC AATTCCTGGG GATCCGCCAT TGTTGAAATT    1440

GGTATTAACA CTGATACAAA AAGAAACACA AGTCGTGCGT GTTGAACTAT CG            1492
```

(2) INFORMATION FOR SEQ ID NO:28:

(i) SEQUENCE CHARACTERISTICS:
    (A) LENGTH: 1194 nucleotides
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:28:

```
ATAGTTCAAC ACGCACGACT TGTGTTTCTT TTTGTATCAG TGTTAATACC AATTTCAACA      60

ATGGCGGATC CCCAGGAATT GTCTACAAGT ATTAACCAGT TGCTGGAAG  CCTGTACAAT     120

ACGGTTGCTT CTGGCAACAA AGACAATCTC ATCATGTCCC CATTGTCTGT ACAAACTGTT     180

CTATCCCTGG TGTCAATGGG AGCTGGTGGT AATACTGCCA CACAAATAGC TGCTGGTTTA     240

CGTCAGCCTC AATCAAAAGA AAAAATTCAA GATGACTACC ACGCATTGAT GAACACTCTT     300

AATACACAAA AAGGTGTAAC TCTGGAAATT GCCAATAAAG TTTATGTTAT GGAAGGCTAT     360

ACATTAAAAC CCACCTTCAA AGAAGTTGCC ACCAACAAAT TCTTAGCTGG AGCAGAAAAC     420

TTGAACTTTG CCCAAAATGC TGAAAGCGCT AAAGTTATCA ACACTTGGGT TGAAGAAAAA     480

ACTCATGACA AAATTCATGA TTTGATCAAA GCCGGTGATC TAGACCAGGA TTCAAGAATG     540

GTTCTTGTCA ATGCATTGTA CTTCAAGGGT CTTTGGGAGA ACAATTCAA  GAAGGAAAAC     600

ACCCAAGACA AACCTTTCTA TGTTACTGAA ACAGAGACAA AGAATGTACG AATGATGCAC     660

ATTAAGGATA AATTCCGTTA TGGAGAATTT GAAGAATTAG ATGCCAAGGC TGTAGAATTG     720

CCCTACAGGA ACTCAGATTT GGCCATGTTA ATCATTTTGC CAAACAGCAA AACTGGTCTC     780

CCCACTCTTG AAGAAAAATT ACAAAATGTT GATTTGCAAA ACTTGACTCA ACGCATGTAC     840

TCTGTTGAAG TTATTTTGGA TCTGCCTAAA TTCAAAATTG AGTCTGAAAT TAATTTGAAT     900

GATCCTCTGA AAAAGTTGGG TATGTCTGAT ATGTTCATGC CTGGAAAAGC TGATTTCAAA     960

GGATTGCTTG AAGGATCTGA TGAGATGTTA TATATTTCTA AAGTAATTCA AAAAGCTTTC    1020

ATTGAAGTAA ATGAAGAAGG TGCTGAAGCT GCAGCTGCCA CAGGCGTGAT GTTAATGATG    1080

CGTTGTATGC CAATGATGCC AATGGCCTTC AATGCTGAGC ATCCATTCCT GTACTTCTTA    1140

CACAGCAAAA ATTCTGTTCT ATTCAATGGT CGTCTTGTTA AACCAACAAC TGAA           1194
```

(2) INFORMATION FOR SEQ ID NO:29:

(i) SEQUENCE CHARACTERISTICS:
    (A) LENGTH: 1194 nucleotides
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:29:

```
TTCAGTTGTT GGTTTAACAA GACGACCATT GAATAGAACA GAATTTTTGC TGTGTAAGAA      60

GTACAGGAAT GGATGCTCAG CATTGAAGGC CATTGGCATC ATTGGCATAC AACGCATCAT     120

TAACATCACG CCTGTGGCAG CTGCAGCTTC AGCACCTTCT TCATTTACTT CAATGAAAGC     180

TTTTTGAATT ACTTTAGAAA TATATAACAT CTCATCAGAT CCTTCAAGCA ATCCTTTGAA     240

ATCAGCTTTT CCAGGCATGA ACATATCAGA CATACCCAAC TTTTTCAGAG GATCATTCAA     300

ATTAATTTCA GACTCAATTT TGAATTTAGG CAGATCCAAA ATAACTTCAA CAGAGTACAT     360

GCGTTGAGTC AAGTTTTGCA AATCAACATT TTGTAATTTT TCTTCAAGAG TGGGGAGACC     420

AGTTTTGCTG TTTGGCAAAA TGATTAACAT GGCCAAATCT GAGTTCCTGT AGGGCAATTC     480
```

-continued

```
TACAGCCTTG GCATCTAATT CTTCAAATTC TCCATAACGG AATTTATCCT TAATGTGCAT      540

CATTCGTACA TTCTTTGTCT CTGTTTCAGT AACATAGAAA GGTTTGTCTT GGGTGTTTTC      600

CTTCTTGAAT TGTTTCTCCC AAAGACCCTT GAAGTACAAT GCATTGACAA GAACCATTCT      660

TGAATCCTGG TCTAGATCAC CGGCTTTGAT CAAATCATGA ATTTTGTCAT GAGTTTTTC       720

TTCAACCCAA GTGTTGATAA CTTTAGCGCT TTCAGCATTT TGGGCAAAGT TCAAGTTTTC      780

TGCTCCAGCT AAGAATTTGT TGGTGGCAAC TTCTTTGAAG GTGGGTTTTA ATGTATAGCC      840

TTCCATAACA TAAACTTTAT TGGCAATTTC CAGAGTTACA CCTTTTTGTG TATTAAGAGT      900

GTTCATCAAT GCGTGGTAGT CATCTTGAAT TTTTTCTTTT GATTGAGGCT GACGTAAACC      960

AGCAGCTATT TGTGTGGCAG TATTACCACC AGCTCCCATT GACACCAGGG ATAGAACAGT     1020

TTGTACAGAC AATGGGGACA TGATGAGATT GTCTTTGTTG CCAGAAGCAA CCGTATTGTA     1080

CAGGCTTCCA GCAAACTGGT TAATACTTGT AGACAATTCC TGGGGATCCG CCATTGTTGA     1140

AATTGGTATT AACACTGATA CAAAAGAAA CACAAGTCGT GCGTGTTGAA CTAT            1194
```

(2) INFORMATION FOR SEQ ID NO:30:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:30:

```
Asp Pro Gln Glu Leu Ser Thr Ser Ile Asn Gln Phe Ala Gly Ser Leu
 1               5                  10                  15

Tyr Asn Thr Val Ala Ser Gly Asn Lys Asp Asn Leu Ile Met Ser Pro
            20                  25                  30

Leu Ser Val Gln Thr Val Leu Ser Leu Val Ser Met Gly Ala Gly Gly
        35                  40                  45

Asn Thr Ala Thr Gln Ile Ala Ala Gly Leu Arg Gln Pro Gln Ser Lys
    50                  55                  60

Glu Lys Ile Gln Asp Asp Tyr His Ala Leu Met Asn Thr Leu Asn Thr
65                  70                  75                  80

Gln Lys Gly Val Thr Leu Glu Ile Ala Asn Lys Val Tyr Val Met Glu
                85                  90                  95

Gly Tyr Thr Leu Lys Pro Thr Phe Lys Glu Val Ala Thr Asn Lys Phe
            100                 105                 110

Leu Ala Gly Ala Glu Asn Leu Asn Phe Ala Gln Asn Ala Glu Ser Ala
        115                 120                 125

Lys Val Ile Asn Thr Trp Val Glu Glu Lys Thr His Asp Lys Ile His
    130                 135                 140

Asp Leu Ile Lys Ala Gly Asp Leu Asp Gln Asp Ser Arg Met Val Leu
145                 150                 155                 160

Val Asn Ala Leu Tyr Phe Lys Gly Leu Trp Glu Lys Gln Phe Lys Lys
                165                 170                 175

Glu Asn Thr Gln Asp Lys Pro Phe Tyr Val Thr Glu Thr Glu Thr Lys
            180                 185                 190

Asn Val Arg Met Met His Ile Lys Asp Lys Phe Arg Tyr Gly Glu Phe
        195                 200                 205

Glu Glu Leu Asp Ala Lys Ala Val Glu Leu Pro Tyr Arg Asn Ser Asp
    210                 215                 220

Leu Ala Met Leu Ile Ile Leu Pro Asn Ser Lys Thr Gly Leu Pro Thr
```

```
225                 230                 235                 240
Leu Glu Glu Lys Leu Gln Asn Val Asp Leu Gln Asn Leu Thr Gln Arg
                245                 250                 255

Met Tyr Ser Val Glu Val Ile Leu Asp Leu Pro Lys Phe Lys Ile Glu
                260                 265                 270

Ser Glu Ile Asn Leu Asn Asp Pro Leu Lys Lys Leu Gly Met Ser Asp
                275                 280                 285

Met Phe Met Pro Gly Lys Ala Asp Phe Lys Gly Leu Leu Glu Gly Ser
                290                 295                 300

Asp Glu Met Leu Tyr Ile Ser Lys Val Ile Gln Lys Ala Phe Ile Glu
305                 310                 315                 320

Val Asn Glu Glu Gly Ala Glu Ala Ala Ala Thr Gly Val Met Leu
                325                 330                 335

Met Met Arg Cys Met Pro Met Met Pro Met Ala Phe Asn Ala Glu His
                340                 345                 350

Pro Phe Leu Tyr Phe Leu His Ser Lys Asn Ser Val Leu Phe Asn Gly
                355                 360                 365

Arg Leu Val Lys Pro Thr Thr Glu
        370                 375

(2) INFORMATION FOR SEQ ID NO:31:

(i) SEQUENCE CHARACTERISTICS:
        (A) LENGTH:  1454 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  20..1210

(xi) SEQUENCE DESCRIPTION:  SEQ ID NO:31:
```

| | |
|---|---|
| GAGCCGAAAT TTTAGCAAA ATG ATT AAC GCA CGA CTT GTG TTT CTT TTT GTA<br>                                  Met Ile Asn Ala Arg Leu Val Phe Leu Phe Val<br>                               1               5              10 | 52 |
| TCA GTG TTA ATA CCA ATT TCA ACA ATG GCG GAT CCC CAG GAA TTG TCT<br>Ser Val Leu Ile Pro Ile Ser Thr Met Ala Asp Pro Gln Glu Leu Ser<br>              15                20                 25 | 100 |
| ACA AGT ATT AAC CAG TTT GCT GGA AGC CTG TAC AAT ACG GTT GCT TCT<br>Thr Ser Ile Asn Gln Phe Ala Gly Ser Leu Tyr Asn Thr Val Ala Ser<br>         30                 35                 40 | 148 |
| GGC AAC AAA GAC AAT CTC ATC ATG TCC CCA TTG TCT GTA CAA ACT GTT<br>Gly Asn Lys Asp Asn Leu Ile Met Ser Pro Leu Ser Val Gln Thr Val<br> 45                 50                 55 | 196 |
| CTA TCC CTG GTG TCA ATG GGA GCT GGT GGT AAT ACT GCC ACA CAA ATA<br>Leu Ser Leu Val Ser Met Gly Ala Gly Gly Asn Thr Ala Thr Gln Ile<br>60                 65                 70                 75 | 244 |
| GCT GCT GGT TTA CGT CAG CCT CAA TCA AAA GAA AAA ATT CAA GAT GAC<br>Ala Ala Gly Leu Arg Gln Pro Gln Ser Lys Glu Lys Ile Gln Asp Asp<br>              80                85                 90 | 292 |
| TAC CAT GCA TTG ATG AAC ACT CTT AAT ACA CAA AAA GGT GTA ACT CTG<br>Tyr His Ala Leu Met Asn Thr Leu Asn Thr Gln Lys Gly Val Thr Leu<br>         95                 100               105 | 340 |
| GAA ATT GCC AAC AAA GTT TAC GTT ATG GAA GGC TAT ACA TTG AAA CCC<br>Glu Ile Ala Asn Lys Val Tyr Val Met Glu Gly Tyr Thr Leu Lys Pro<br>        110                115               120 | 388 |
| ACC TTC AAA GAA GTT GCC ACC AAC AAA TTC TTA GCT GGA GCA GAA AAC | 436 |

```
            Thr Phe Lys Glu Val Ala Thr Asn Lys Phe Leu Ala Gly Ala Glu Asn
                125                 130                 135

TTG AAC TTT GCC CAA AAT GCT GAA AGC GCT AAA GTT ATC AAC ACT TGG         484
Leu Asn Phe Ala Gln Asn Ala Glu Ser Ala Lys Val Ile Asn Thr Trp
140                 145                 150                 155

GTT GAA GAA AAA ACT CAT GAC AAA ATT CAT GAT TTG ATC AAA GCC GGT         532
Val Glu Glu Lys Thr His Asp Lys Ile His Asp Leu Ile Lys Ala Gly
                    160                 165                 170

GAT CTA GAC CAG GAT TCA AGA ATG GTT CTT GTC AAT GCA TTG TAC TTC         580
Asp Leu Asp Gln Asp Ser Arg Met Val Leu Val Asn Ala Leu Tyr Phe
                175                 180                 185

AAG GGT CTT TGG GAG AAA CAA TTC AAG AAG GAA AAC ACT CAA GAC AAA         628
Lys Gly Leu Trp Glu Lys Gln Phe Lys Lys Glu Asn Thr Gln Asp Lys
            190                 195                 200

CCT TTC TAT GTT ACT GAA ACA GAG ACA AAG AAT GTA CGA ATG ATG CAC         676
Pro Phe Tyr Val Thr Glu Thr Glu Thr Lys Asn Val Arg Met Met His
        205                 210                 215

ATT AAG GAT AAA TTC CGT TAT GGA GAA TTT GAA GAA TTA GAT GCC AAG         724
Ile Lys Asp Lys Phe Arg Tyr Gly Glu Phe Glu Glu Leu Asp Ala Lys
220                 225                 230                 235

GCT GTA GAA TTG CCC TAC AGG AAC TCA GAT TTG GCC ATG TTA ATC ATT         772
Ala Val Glu Leu Pro Tyr Arg Asn Ser Asp Leu Ala Met Leu Ile Ile
                    240                 245                 250

TTG CCA AAC AGC AAA ACT GGT CTC CCC GCT CTT GAA GAA AAA TTA CAA         820
Leu Pro Asn Ser Lys Thr Gly Leu Pro Ala Leu Glu Glu Lys Leu Gln
                255                 260                 265

AAT GTT GAC TTG CAA AAC TTG ACT CAA CGC ATG TAC TCT GTT GAA GTT         868
Asn Val Asp Leu Gln Asn Leu Thr Gln Arg Met Tyr Ser Val Glu Val
                270                 275                 280

ATT TTG GAT CTG CCT AAA TTC AAG ATT GAA TCT GAA ATT AAT TTG AAT         916
Ile Leu Asp Leu Pro Lys Phe Lys Ile Glu Ser Glu Ile Asn Leu Asn
285                 290                 295

GAT CCT CTG AAA AAG TTG GGT ATG TCT GAT ATG TTT GTT CCT GGA AAA         964
Asp Pro Leu Lys Lys Leu Gly Met Ser Asp Met Phe Val Pro Gly Lys
300                 305                 310                 315

GCT GAT TTC AAA GGA TTG CTT GAA GGA TCT GAT GAG ATG TTA TAT ATT         1012
Ala Asp Phe Lys Gly Leu Leu Glu Gly Ser Asp Glu Met Leu Tyr Ile
                320                 325                 330

TCT AAA GTA ATT CAA AAA GCT TTC ATT GAA GTA AAT GAA GAA GGT GCT         1060
Ser Lys Val Ile Gln Lys Ala Phe Ile Glu Val Asn Glu Glu Gly Ala
                335                 340                 345

GAA GCT GCA GCT GCC ACA GCT ACC TTT ATG GTT ACC TAT GAA CTG GAG         1108
Glu Ala Ala Ala Ala Thr Ala Thr Phe Met Val Thr Tyr Glu Leu Glu
            350                 355                 360

GTT TCC CTG GAT GAT CCA ACC GTT TTT AAA GTC GAT CAT CCA TTC AAT         1156
Val Ser Leu Asp Asp Pro Thr Val Phe Lys Val Asp His Pro Phe Asn
365                 370                 375

ATT GTT TTG AAG ACA GGT GAT ACT GTA ATT TTT AAT GGG CGA GTT CAA         1204
Ile Val Leu Lys Thr Gly Asp Thr Val Ile Phe Asn Gly Arg Val Gln
380                 385                 390                 395

ACT CTA TGA AATGGATAGT GTAAGAAAAG AATACAAGAT CTATCTGAAT CTCTGGATTA     1263
Thr Leu

ATGAAGTAAT TTTTCTACAA TATTTTTTAA TAGTTATTAG GTCTAAAATA AGTTCATTTT       1323

TTAGTATGTG GTATAAATCG TGTAGACGAA AAATGTTTTG TTTTAGTTTT CACTTTTTAT       1383

GAATGTAATC ACCTATATAA TGTTGTAGTT TATGTAATAA AAATGTTAAA TGTGAAAAAA       1443

AAAAAAAAAA A                                                           1454
```

(2) INFORMATION FOR SEQ ID NO:32:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO:32:

```
Met Ile Asn Ala Arg Leu Val Phe Leu Phe Val Ser Val Leu Ile Pro
  1               5                  10                  15

Ile Ser Thr Met Ala Asp Pro Gln Glu Leu Ser Thr Ser Ile Asn Gln
             20                  25                  30

Phe Ala Gly Ser Leu Tyr Asn Thr Val Ala Ser Gly Asn Lys Asp Asn
         35                  40                  45

Leu Ile Met Ser Pro Leu Ser Val Gln Thr Val Leu Ser Leu Val Ser
     50                  55                  60

Met Gly Ala Gly Gly Asn Thr Ala Thr Gln Ile Ala Ala Gly Leu Arg
 65                  70                  75                  80

Gln Pro Gln Ser Lys Glu Lys Ile Gln Asp Asp Tyr His Ala Leu Met
                 85                  90                  95

Asn Thr Leu Asn Thr Gln Lys Gly Val Thr Leu Glu Ile Ala Asn Lys
            100                 105                 110

Val Tyr Val Met Glu Gly Tyr Thr Leu Lys Pro Thr Phe Lys Glu Val
        115                 120                 125

Ala Thr Asn Lys Phe Leu Ala Gly Ala Glu Asn Leu Asn Phe Ala Gln
    130                 135                 140

Asn Ala Glu Ser Ala Lys Val Ile Asn Thr Trp Val Glu Glu Lys Thr
145                 150                 155                 160

His Asp Lys Ile His Asp Leu Ile Lys Ala Gly Asp Leu Asp Gln Asp
                165                 170                 175

Ser Arg Met Val Leu Val Asn Ala Leu Tyr Phe Lys Gly Leu Trp Glu
            180                 185                 190

Lys Gln Phe Lys Lys Glu Asn Thr Gln Asp Lys Pro Phe Tyr Val Thr
        195                 200                 205

Glu Thr Glu Thr Lys Asn Val Arg Met Met His Ile Lys Asp Lys Phe
    210                 215                 220

Arg Tyr Gly Glu Phe Glu Leu Asp Ala Lys Ala Val Glu Leu Pro
225                 230                 235                 240

Tyr Arg Asn Ser Asp Leu Ala Met Leu Ile Ile Leu Pro Asn Ser Lys
                245                 250                 255

Thr Gly Leu Pro Ala Leu Glu Glu Lys Leu Gln Asn Val Asp Leu Gln
            260                 265                 270

Asn Leu Thr Gln Arg Met Tyr Ser Val Glu Val Ile Leu Asp Leu Pro
        275                 280                 285

Lys Phe Lys Ile Glu Ser Glu Ile Asn Leu Asn Asp Pro Leu Lys Lys
    290                 295                 300

Leu Gly Met Ser Asp Met Phe Val Pro Gly Lys Ala Asp Phe Lys Gly
305                 310                 315                 320

Leu Leu Glu Gly Ser Asp Glu Met Leu Tyr Ile Ser Lys Val Ile Gln
                325                 330                 335

Lys Ala Phe Ile Glu Val Asn Glu Glu Gly Ala Glu Ala Ala Ala
        340                 345                 350

Thr Ala Thr Phe Met Val Thr Tyr Glu Leu Glu Val Ser Leu Asp Asp
```

```
                355                 360                 365
Pro Thr Val Phe Lys Val Asp His Pro Phe Asn Ile Val Leu Lys Thr
    370                 375                 380
Gly Asp Thr Val Ile Phe Asn Gly Arg Val Gln Thr Leu
385                 390                 395
```

(2) INFORMATION FOR SEQ ID NO:33:

(i) SEQUENCE CHARACTERISTICS:
        (A) LENGTH: 1454 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
TTTTTTTTTT TTTTTTTCAC ATTTAACATT TTTATTACAT AAACTACAAC ATTATATAGG    60
TGATTACATT CATAAAAAGT GAAAACTAAA ACAAACATT TTTCGTCTAC ACGATTTATA    120
CCACATACTA AAAAATGAAC TTATTTTAGA CCTAATAACT ATTAAAAAAT ATTGTAGAAA    180
AATTACTTCA TTAATCCAGA GATTCAGATA GATCTTGTAT TCTTTTCTTA CACTATCCAT    240
TTCATAGAGT TTGAACTCGC CCATTAAAAA TTACAGTATC ACCTGTCTTC AAAACAATAT    300
TGAATGGATG ATCGACTTTA AAAACGGTTG GATCATCCAG GGAAACCTCC AGTTCATAGG    360
TAACCATAAA GGTAGCTGTG GCAGCTGCAG CTTCAGCACC TTCTTCATTT ACTTCAATGA    420
AAGCTTTTTG AATTACTTTA GAAATATATA ACATCTCATC AGATCCTTCA AGCAATCCTT    480
TGAAATCAGC TTTTCCAGGA ACAAACATAT CAGACATACC CAACTTTTTC AGAGGATCAT    540
TCAAATTAAT TTCAGATTCA ATCTTGAATT TAGGCAGATC CAAAATAACT TCAACAGAGT    600
ACATGCGTTG AGTCAAGTTT TGCAAGTCAA CATTTTGTAA TTTTTCTTCA AGAGCGGGGA    660
GACCAGTTTT GCTGTTTGGC AAAATGATTA ACATGGCCAA ATCTGAGTTC CTGTAGGGCA    720
ATTCTACAGC CTTGGCATCT AATTCTTCAA ATTCTCCATA ACGGAATTTA TCCTTAATGT    780
GCATCATTCG TACATTCTTT GTCTCTGTTT CAGTAACATA GAAAGGTTTG TCTTGAGTGT    840
TTTCCTTCTT GAATTGTTTC TCCCAAAGAC CCTTGAAGTA CAATGCATTG ACAAGAACCA    900
TTCTTGAATC CTGGTCTAGA TCACCGGCTT TGATCAAATC ATGAATTTTG TCATGAGTTT    960
TTTCTTCAAC CCAAGTGTTG ATAACTTTAG CGCTTTCAGC ATTTTGGGCA AAGTTCAAGT   1020
TTTCTGCTCC AGCTAAGAAT TTGTTGGTGG CAACTTCTTT GAAGGTGGGT TTCAATGTAT   1080
AGCCTTCCAT AACGTAAACT TTGTTGGCAA TTTCCAGAGT TACACCTTTT TGTGTATTAA   1140
GAGTGTTCAT CAATGCATGG TAGTCATCTT GAATTTTTTC TTTTGATTGA GGCTGACGTA   1200
AACCAGCAGC TATTTGTGTG GCAGTATTAC CACCAGCTCC CATTGACACC AGGGATAGAA   1260
CAGTTTGTAC AGACAATGGG GACATGATGA GATTGTCTTT GTTGCCAGAA GCAACCGTAT   1320
TGTACAGGCT TCCAGCAAAC TGGTTAATAC TTGTAGACAA TTCCTGGGGA TCCGCCATTG   1380
TTGAAATTGG TATTAACACT GATACAAAAA GAAACACAAG TCGTGCGTTA ATCATTTTGC   1440
TAAAATTTCG GCTC                                                    1454
```

(2) INFORMATION FOR SEQ ID NO:34:

(i) SEQUENCE CHARACTERISTICS:
        (A) LENGTH: 1191 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
ATGATTAACG CACGACTTGT GTTTCTTTTT GTATCAGTGT TAATACCAAT TTCAACAATG      60

GCGGATCCCC AGGAATTGTC TACAAGTATT AACCAGTTTG CTGGAAGCCT GTACAATACG     120

GTTGCTTCTG GCAACAAAGA CAATCTCATC ATGTCCCCAT TGTCTGTACA AACTGTTCTA     180

TCCCTGGTGT CAATGGGAGC TGGTGGTAAT ACTGCCACAC AAATAGCTGC TGGTTTACGT     240

CAGCCTCAAT CAAAAGAAAA AATTCAAGAT GACTACCATG CATTGATGAA CACTCTTAAT     300

ACACAAAAAG GTGTAACTCT GGAAATTGCC AACAAAGTTT ACGTTATGGA AGGCTATACA     360

TTGAAACCCA CCTTCAAAGA AGTTGCCACC AACAAATTCT TAGCTGGAGC AGAAAACTTG     420

AACTTTGCCC AAAATGCTGA AGCGCTAAA GTTATCAACA CTTGGGTTGA AGAAAAAACT      480

CATGACAAAA TTCATGATTT GATCAAAGCC GGTGATCTAG ACCAGGATTC AAGAATGGTT     540

CTTGTCAATG CATTGTACTT CAAGGGTCTT TGGGAGAAAC AATTCAAGAA GGAAAACACT     600

CAAGACAAAC CTTTCTATGT TACTGAAACA GAGACAAAGA ATGTACGAAT GATGCACATT     660

AAGGATAAAT TCCGTTATGG AGAATTTGAA GAATTAGATG CCAAGGCTGT AGAATTGCCC     720

TACAGGAACT CAGATTTGGC CATGTTAATC ATTTTGCCAA ACAGCAAAAC TGGTCTCCCC     780

GCTCTTGAAG AAAAATTACA AAATGTTGAC TTGCAAAACT TGACTCAACG CATGTACTCT     840

GTTGAAGTTA TTTTGGATCT GCCTAAATTC AAGATTGAAT CTGAAATTAA TTTGAATGAT     900

CCTCTGAAAA AGTTGGGTAT GTCTGATATG TTTGTTCCTG AAAAGCTGA TTTCAAGGA      960

TTGCTTGAAG GATCTGATGA GATGTTATAT ATTTCTAAAG TAATTCAAAA AGCTTTCATT    1020

GAAGTAAATG AAGAAGGTGC TGAAGCTGCA GCTGCCACAG CTACCTTTAT GGTTACCTAT    1080

GAACTGGAGG TTTCCCTGGA TGATCCAACC GTTTTTAAAG TCGATCATCC ATTCAATATT    1140

GTTTTGAAGA CAGGTGATAC TGTAATTTTT AATGGGCGAG TTCAAACTCT A            1191
```

(2) INFORMATION FOR SEQ ID NO:35:

(i) SEQUENCE CHARACTERISTICS:
        (A) LENGTH: 1191 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

```
TAGAGTTTGA ACTCGCCCAT TAAAAATTAC AGTATCACCT GTCTTCAAAA CAATATTGAA      60

TGGATGATCG ACTTTAAAAA CGGTTGGATC ATCCAGGGAA ACCTCCAGTT CATAGGTAAC     120

CATAAAGGTA GCTGTGGCAG CTGCAGCTTC AGCACCTTCT TCATTTACTT CAATGAAAGC     180

TTTTTGAATT ACTTTAGAAA TATATAACAT CTCATCAGAT CCTTCAAGCA ATCCTTTGAA     240

ATCAGCTTTT CCAGGAACAA ACATATCAGA CATACCCAAC TTTTTCAGAG GATCATTCAA     300

ATTAATTTCA GATTCAATCT TGAATTTAGG CAGATCCAAA ATAACTTCAA CAGAGTACAT     360

GCGTTGAGTC AAGTTTTGCA AGTCAACATT TTGTAATTTT TCTTCAAGAG CGGGGAGACC     420

AGTTTTGCTG TTTGGCAAAA TGATTAACAT GGCCAAATCT GAGTTCCTGT AGGGCAATTC     480

TACAGCCTTG GCATCTAATT CTTCAAATTC TCCATAACGG AATTTATCCT TAATGTGCAT     540

CATTCGTACA TTCTTTGTCT CTGTTTCAGT AACATAGAAA GGTTTGTCTT GAGTGTTTTC     600

CTTCTTGAAT TGTTTCTCCC AAAGACCCTT GAAGTACAAT GCATTGACAA GAACCATTCT     660
```

-continued

```
TGAATCCTGG TCTAGATCAC CGGCTTTGAT CAAATCATGA ATTTTGTCAT GAGTTTTTTC      720

TTCAACCCAA GTGTTGATAA CTTTAGCGCT TTCAGCATTT TGGGCAAAGT TCAAGTTTTC      780

TGCTCCAGCT AAGAATTTGT TGGTGGCAAC TTCTTTGAAG GTGGGTTTCA ATGTATAGCC      840

TTCCATAACG TAAACTTTGT TGGCAATTTC CAGAGTTACA CCTTTTTGTG TATTAAGAGT      900

GTTCATCAAT GCATGGTAGT CATCTTGAAT TTTTTCTTTT GATTGAGGCT GACGTAAACC      960

AGCAGCTATT TGTGTGGCAG TATTACCACC AGCTCCCATT GACACCAGGG ATAGAACAGT     1020

TTGTACAGAC AATGGGGACA TGATGAGATT GTCTTTGTTG CCAGAAGCAA CCGTATTGTA     1080

CAGGCTTCCA GCAAACTGGT TAATACTTGT AGACAATTCC TGGGGATCCG CCATTGTTGA     1140

AATTGGTATT AACACTGATA CAAAAAGAAA CACAAGTCGT GCGTTAATCA T              1191
```

(2) INFORMATION FOR SEQ ID NO:36:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:36:

```
Asp Pro Gln Glu Leu Ser Thr Ser Ile Asn Gln Phe Ala Gly Ser Leu
 1               5                  10                  15

Tyr Asn Thr Val Ala Ser Gly Asn Lys Asp Asn Leu Ile Met Ser Pro
                20                  25                  30

Leu Ser Val Gln Thr Val Leu Ser Leu Val Ser Met Gly Ala Gly Gly
            35                  40                  45

Asn Thr Ala Thr Gln Ile Ala Ala Gly Leu Arg Gln Pro Gln Ser Lys
        50                  55                  60

Glu Lys Ile Gln Asp Asp Tyr His Ala Leu Met Asn Thr Leu Asn Thr
 65                 70                  75                  80

Gln Lys Gly Val Thr Leu Glu Ile Ala Asn Lys Val Tyr Val Met Glu
                85                  90                  95

Gly Tyr Thr Leu Lys Pro Thr Phe Lys Glu Val Ala Thr Asn Lys Phe
                100                 105                 110

Leu Ala Gly Ala Glu Asn Leu Asn Phe Ala Gln Asn Ala Glu Ser Ala
            115                 120                 125

Lys Val Ile Asn Thr Trp Val Glu Glu Lys Thr His Asp Lys Ile His
        130                 135                 140

Asp Leu Ile Lys Ala Gly Asp Leu Asp Gln Asp Ser Arg Met Val Leu
145                 150                 155                 160

Val Asn Ala Leu Tyr Phe Lys Gly Leu Trp Glu Lys Gln Phe Lys Lys
                165                 170                 175

Glu Asn Thr Gln Asp Lys Pro Phe Tyr Val Thr Glu Thr Glu Thr Lys
                180                 185                 190

Asn Val Arg Met Met His Ile Lys Asp Lys Phe Arg Tyr Gly Glu Phe
            195                 200                 205

Glu Glu Leu Asp Ala Lys Ala Val Glu Leu Pro Tyr Arg Asn Ser Asp
        210                 215                 220

Leu Ala Met Leu Ile Ile Leu Pro Asn Ser Lys Thr Gly Leu Pro Ala
225                 230                 235                 240

Leu Glu Glu Lys Leu Gln Asn Val Asp Leu Gln Asn Leu Thr Gln Arg
                245                 250                 255
```

```
Met Tyr Ser Val Glu Val Ile Leu Asp Leu Pro Lys Phe Lys Ile Glu
            260                 265                 270

Ser Glu Ile Asn Leu Asn Asp Pro Leu Lys Lys Leu Gly Met Ser Asp
            275                 280                 285

Met Phe Val Pro Gly Lys Ala Asp Phe Lys Gly Leu Leu Glu Gly Ser
            290                 295                 300

Asp Glu Met Leu Tyr Ile Ser Lys Val Ile Gln Lys Ala Phe Ile Glu
305                 310                 315                 320

Val Asn Glu Glu Gly Ala Glu Ala Ala Ala Thr Ala Thr Phe Met
                325                 330                 335

Val Thr Tyr Glu Leu Glu Val Ser Leu Asp Asp Pro Thr Val Phe Lys
            340                 345                 350

Val Asp His Pro Phe Asn Ile Val Leu Lys Thr Gly Asp Thr Val Ile
            355                 360                 365

Phe Asn Gly Arg Val Gln Thr Leu
            370                 375
```

(2) INFORMATION FOR SEQ ID NO:37:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:37:

GTGTTTCTTT TTGTATCAGT G                                                      21

(2) INFORMATION FOR SEQ ID NO:38:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:38:

CGGAATTCTT TAAAGGGATT TAACAC                                     26

(2) INFORMATION FOR SEQ ID NO:39:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:39:

CGGAATTCTA ATTGGTAAAT CTC                                          23

(2) INFORMATION FOR SEQ ID NO:40:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: primer -continued (xi) SEQUENCE DESCRIPTION: SEQ ID NO:40:

CGGAATTCTT TTATTCAGTT GTTGG                            25

(2) INFORMATION FOR SEQ ID NO:41:

(i) SEQUENCE CHARACTERISTICS:
        (A) LENGTH:  23 bases
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:41:

CGGAATTCAT AGAGTTTGAA CTC                              23

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated flea protein selected from the group consisting of: (a) a protein comprising an amino acid sequence selected from the group consisting of SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO:30, SEQ ID NO:32, SEQ ID NO:36; and (b) a protein encoded by a naturally occurring splice variant of a nucleic acid molecule that encodes a protein of (a), wherein said protein encoded by a naturally occurring splice variant has serine protease inhibitor activity.

2. The protein of claim 1, wherein said protein, when administered to an animal, elicits an immune response against a *Ctenocephalides felis* serine protease inhibitor protein.

3. The protein of claim 1, wherein said protein is encoded by a nucleic acid molecule having a nucleic acid sequence selected from the group consisting of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, and SEQ ID NO:34.

4. The protein of claim 1, wherein said protein comprises an amino acid sequence selected from the group consisting of SEQ ID NO:2, SEQ ID NO:6, SEQ ID NO:8, SEQ ID NO:12, SEQ ID NO:14, SEQ ID NO:18, SEQ ID NO:20, SEQ ID NO:24, SEQ ID NO:26, SEQ ID NO:30, SEQ ID NO:32, and SEQ ID NO:36.

* * * * *